US008299276B2

(12) United States Patent
Clark et al.

(10) Patent No.: US 8,299,276 B2
(45) Date of Patent: Oct. 30, 2012

(54) INTERLOCKED MOLECULES AND RELATED COMPONENTS, COMPOSITIONS, METHODS AND SYSTEMS

(75) Inventors: Paul G. Clark, Pasadena, CA (US); Robert H. Grubbs, South Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 12/711,247

(22) Filed: Feb. 23, 2010

(65) Prior Publication Data

US 2011/0065935 A1  Mar. 17, 2011

Related U.S. Application Data

(60) Provisional application No. 61/243,490, filed on Sep. 17, 2009.

(51) Int. Cl.
*C07D 331/00* (2006.01)
(52) U.S. Cl. ..................................................... 549/351
(58) Field of Classification Search ................... 549/351
See application file for complete search history.

(56) References Cited

OTHER PUBLICATIONS

Chiu et al. See. Chem. Commun., 2002, 2948-2949.*
Guidry et al. Journal of the American Chemical Society, 2007, 129, 8944-8945.*
Ashton et al. Tetrahedron Lett. 1999, 40, 3661-3664.*
Fielding, Lee. Tetrahedron 2000, 56, 6151-6170.*
Milknaic et al. Proc. Natl. Acad. Sci. USA 2007, 104, 12966-12970.*
Gribkova et al. Russian Chemical Reviews, 1993, 62(10), 963-979.*
Rescifina, A. et al., Recent Developments on Rotaxane-Based Shuttles, *Curr. Org. Chem.* 2009, vol. 13, pp. 448-481.
Meyer, C. D. et al., Template-directed synthesis employing reversible imine bond formation, *Chem. Soc. ReV.* 2007, vol. 36, pp. 1705-1723.
Haussmann, P. C. et al., Synthesizing Interlocked Molecules Dynamically, *Chem. Record* 2009, vol. 9, pp. 136-154.
Rowan, S. J. et al., Dynamic Covalent Chemistry, *Angew. Chem., Int. Ed.* 2002, vol. 41, pp. 898-952.
Bilig, T. et al., Polyrotaxane Networks Formed via Rotaxanation Utilizing Dynamic Covalent Chemistry of Disulfide, *Macromolecules* 2008, vol. 41, pp. 8496-8503.
Bügler, J. et al., Interconnective Host-Guest Complexation of β-Cyclodextrin-Calix[4]arene Couples, *J. Am. Chem. Soc.* 1999, vol. 121, pp. 28-33.
Hirotsu, K. et al. Polymeric Inclusion Compound Derived from β-Cyclodextrin, *J. Org. Chem.* 1982, vol. 47, pp. 1143-1144.
Liu, Y. et al., Supramolecular Aggregates Formed by Intermolecular Inclusion Complexation of Organo-Selenium Bridged Bis(cyclodextrin)s with Calix[4]arene Derivative, *Nano Lett.* 2002, vol. 2, pp. 257-261.

Liu, Y. et al., Molecular Interpenetration within the Columnar Structure of Crystalline Anilino-β-cyclodextrin, *Org. Lett.* 2000, vol. 2, pp. 2761-2763.
Wu, J. et al., Efficient production of [n]rotaxanes by using template-directed clipping reactions, *Proc. Natl. Acad. Sci. U.S.A.* 2007, vol. 104, pp. 17266-17271.
Cantrill, S. J. et al., Supramolecular Daisy Chains, *J. Org. Chem.* 2001, vol. 66, pp. 6857-6872.
Jiménez, M. C. et al., A Hermaphrodite Molecule: Quantitative Copper(I)-Directed Formation of a Doubly Threaded Assembly from a Ring Attached to a String, A. *Angew. Chem., Int. Ed.* 2000, vol. 39, No. 7, pp. 1295-1298.
Yamaguchi, N. et al., Self-Organization of a Heteroditopic Molecule to Linear Polymolecular Arrays in Solution, *Angew. Chem., Int. Ed.* 1998, vol. 37, No. 17, pp. 2361-2364.
Ashton, P.R. et al., Supramolecular Daisy Chains, *Angew. Chem., Int. Ed.* 1998, vol. 37, No. 9, pp. 1294-1297.
Coutrot, F. et al., A New pH-Switchable Dimannosyl[c2]Daisy Chain Molecular Machine, *Org. Lett.* 2008, vol. 10, No. 17, pp. 3741-3744.
Wu, J. et al., An Acid-Base-Controllable [c2]Daisy Chain, Angew. Chem., Int. Ed. 2008, vol. 47, pp. 7470-7474.
Jiménez, M. C. et al., Towards Synthetic Molecular Muscles: Contraction and Stretching of a Linear Rotaxane Dimer, Angew.Chem. 2000, vol. 39, No. 18, pp. 3284-3287.
Elizarov, A. M. et al., An Acid-Base Switchable [2]Rotaxane, J. Org. Chem. 2002, vol. 67, pp. 9175-9181.
Pease, A. R. et al., Switching Devices Based on Interlocked Molecules, Acc. Chem. Res. 2001, vol. 34, No. 6, pp. 433-444.
Fustin, C. A. et al., Mechanically Linked Poly(ethylene terephthalate), Macromolecules 2004, vol. 37, pp. 7884-7892.
Fustin, C.-A. et al., Solution and Solid-State Properties of Mechanically Linked Polycarbonates, *Macromolecules* 2004, vol. 37, pp. 66-70.
Fustin, C.-A. et al., Mechanically Linked Polycarbonate, *J. Am. Chem. Soc.* 2003, vol. 125, pp. 2200-2207.
Watanabe, N. et al., Communications to the Editor: Bridged Polycatenane, *Macromolecules* 2004, vol. 37, pp. 6663-6666.
Werts, M. P. L. et al., Mechanically Linked Polyrotaxanes: A Stepwise Approach, *Macromolecules* 2003, vol. 36, pp. 7004-7013.
Guidry, E. N. et al., Bifunctional [c2]Daisy-Chains and Their Incorporation into Mechanically Interlocked Polymers, *J. Am. Chem. Soc.* 2007, vol. 129, pp. 8944-8945.
Fang, L. et al., Acid-Base Actuation of [c2]Daisy Chains, *J. Am. Chem. Soc.* 2009, vol. 131, pp. 7126-7134.
Chiu, S.-H. et al., An hermaphroditic [c2]daisy chain, *Chem. Commun.* 2002, pp. 2948-2949.
Rowan, S. J. et al., Toward Daisy Chain Polymers: "Wittig Exchange" of Stoppers in [2]Rotaxane Monomers, *Org. Lett.* 2000, vol. 2, No. 6, pp. 759-762.
Ueng, S.-H. et al., Capturing a [c2]daisy chain using the threading-followed-by-swelling approach, *Chem. Commun.* 2008, pp. 817-819.
Hoshino, T. et al., Daisy Chain Necklace: Tri[2]rotaxane Containing Cyclodextrins, *J. Am. Chem. Soc.* 2000, vol. 122, pp. 9876-9877.
Trnka, T. M. et al., The Development of $L_2X_2Ru=CHR$ Olefin Metathesis Catalysts: An Organometallic Success Story, *Acc. Chem. Res.* 2001, vol. 34, No. 1, pp. 18-29.
Scholl, M. et al., Synthesis and Activity of a New Generation of Ruthenium-Based Olefin Metathesis Catalysts Coordinated with 1,3-Dimesityl-4,5-dihydroimidazol-2-ylidene Ligands, *Org. Lett.* 1999, vol. 1, No. 6, pp. 953-956.
Kidd, T. J. et al., Organic "Magic Rings": The Hydrogen Bond-Directed Assembly of Catenanes under Thermodynamic Control, *J. Am. Chem. Soc.* 1999, vol. 121, pp. 1599-1600.

(Continued)

Primary Examiner — Nizal Chandrakumar
(74) Attorney, Agent, or Firm — Steinfl & Bruno LLP

(57) ABSTRACT

[c2] daisy chain macromers, dimers and polymers and related compositions, materials, methods and systems are described.

18 Claims, 20 Drawing Sheets

OTHER PUBLICATIONS

Weck, M. et al., Synthesis of Catenane Structures via Ring-Closing Metathesis, *J. Org.Chem.* 1999, vol. 64, pp. 5463-5471.

Mobian, P. et al., A [2]Catenane Constructed around a Ru(Diimine)$_3^{2+}$ Complex Used as a Template, *J. Am. Chem. Soc.* 2003, vol. 125, pp. 2016-2017.

Sambrook, M. R. et al., Anion-Templated Assembly of a [2]Catenane, *J. Am. Chem. Soc.* 2004, vol. 126, pp. 15364-15365.

Guidry, E. N. et al., Magic Ring Catenation by Olefin Metathesis, *Org. Lett.* 2005, vol. 7, pp. 2129-2132.

Wisner, J. A. et al., Anion-Templated Rotaxane Formation, *J. Am. Chem. Soc.* 2002, vol. 124, pp. 12469-12476.

Kilbinger, A. F. M. et al., Magic Ring Rotaxanes by Olefin Metathesis, *Angew. Chem., Int. Ed.* 2003, vol. 42, pp. 3281-3285.

Hannam, J. S. et al., "Magic Rod" Rotaxanes: The Hydrogen Bond-Directed Synthesis of Molecular Shuttles under Thermodynamic Control, Org. Lett. 2003, vol. 5, pp. 1907-1910.

Coumans, R. G. E. et al., Synthesis of Porphyrin-Containing [3]Rotaxanes by Olefin Metathesis, *Angew. Chem., Int. Ed.* 2003, vol. 42, No. 6, pp. 650-654.

Badjić, J. D. et al., The Exclusivity of Multivalency in Dynamic Covalent Processes, *Angew. Chem., Int. Ed.* 2004, vol. 43, pp. 3273-3278.

Wang, L. et al., Multiple Catenanes Derived from Calix[4]arenes, *Science* 2004, vol. 304, pp. 1312-1314.

Zhu, X.-Z. et al., A Highly Efficient Approach to [4]Pseudocatenanes by Threefold Metathesis Reactions of a Triptycene-Based Tris[2]pseudorotaxane, *J. Am. Chem. Soc.* 2005, vol. 127, pp. 13158-13159.

Nielsen, M. B. et al., Self-Complexing Tetrathiafulvalene-Based Donor-Acceptor Macrocycles, *Eur. J. Org. Chem.* 1999, pp. 2807-2815.

Crystallographic data have been deposited at the CCDC: deposition No. 734570. See Supporting Information of Clark, P.G., et al., Switching and Extension of a [c2]Daisy-Chain Dimer Polymer, *J. Am. Chem. Soc.*, 2009, vol. 131 (38), pp. 13631-13633 for complete details.

Coates, G. W. et al., Phenyl-Perfluorophenyl Stacking Interactions: A New Strategy for Supermolecule Construction, *Angew. Chem., Int. Ed.* 1997, vol. 36, pp. 248-251.

Liu, Y. et al., Linear Artificial Molecular Muscles, *J. Am. Chem. Soc.* 2005, vol. 127, pp. 9745-9797.

Kolb, H. C. et al., Click Chemistry: Diverse Chemical Function from a Few Good Reactions, *Angew. Chem., Int. Ed.* 2001, vol. 40, pp. 2004-2021.

Lutz, J.-F. Copper-Free Azide-Alkyne Cycloadditions: New Insights and Perspectives, *Angew. Chem., Int. Ed.* 2008, vol. 47, pp. 2182-2184.

* cited by examiner

Cap Binding Site    Backbone    Recognition Moiety

Coordination                    Interlocking

↓ Vacuum

↓ Swelling

INTERLOCKED MOLECULES AND RELATED COMPONENTS, COMPOSITIONS, METHODS AND SYSTEMS

CROSS REFERENCE TO RELATED APPLICATIONS

This application claims priority to U.S. provisional application Ser. No. 61/243,490, filed on Sep. 17, 2009 entitled "Synthesis and Extension of a [c2] Daisy-Chain Dimer Polymer", incorporated herein by reference in its entirety.

CROSS REFERENCE TO RELATED PUBLICATIONS

The present application is also related to the paper entitled "Switching and Extension of a [c2]Daisy-Chain Dimer Polymer" published on Journal of American Chemical Society 2009, 131 (38), pp 13631-13633 and related supplementary and supporting information, herein also incorporated by reference in their entirety.

STATEMENT OF GOVERNMENT GRANT

The U.S. Government has certain rights in this invention pursuant to Grant No. CHE0809418 awarded by the National Science Foundation and pursuant to Grant No. N00014-0310792 awarded by the Office of Naval Research.

FIELD

The present disclosure relates to interlocked molecules and to related components, compositions, materials methods and systems.

BACKGROUND

Utilization of supramolecular chemistry to self-assemble complex molecular networks coupled with dynamic covalent chemistry has facilitated the synthesis of a variety of interlocked molecules whose conformation can be changed using switchable non covalent interactions.

Various classes of interlocked molecules have been investigated as artificial molecular actuators able to convert chemical, electrochemical or photochemical energy into mechanical motion. Possible uses for such molecular actuators include nanoelectromechanical systems and other applications where controlled conformational switches are desirable.

SUMMARY

Provided herein are interlocked molecules, that in several embodiments are able to assume extended and contracted conformations which are switchable in a controlled fashion, and related macromers, materials compositions, methods and system. In particular, provided herein are [c2] daisy-chain dimers that in several embodiments can switch from a stable extended state to a stable contracted state upon controlled removal and reinstatement of coordinating interactions within the dimers.

According to a first aspect, a [c2] daisy chain macromer is described. The [c2] daisy chain macromer comprises a binding site and a corresponding recognition moiety, the binding site presenting a secondary amine and the corresponding recognition moiety comprising a first polyether chain and a second polyether chain, the first polyether chain presenting a first olefin and the second polyether chain presenting a second olefin, with the first and second polyether chains configured to allow binding of the first olefin with the second\olefin through metathesis. In the [c2] daisy chain macromer, the binding site and the recognition moiety are configured to allow a coordinate binding of the recognition moiety to the binding site with an association constant ($K_a$) equal to or above, about 75 $M^{-1}$.

The macromer also comprises a backbone portion located between the binding site and the recognition moiety, wherein the backbone comprises structurally rigid functionalities configured to minimize intramolecular interactions between the recognition moiety and the binding site.

The macromer also comprises a cap portion adjacent to the binding site, the cap portion configured to constrain movements of a recognition moiety when coordinately bond to the binding site, with the cap portion and the recognition moiety located at opposite ends of the macromer.

In the macromer, the cap portion, the binding site, the backbone and the recognition moiety are attached together to form a linear [c2]daisy-chain macromer structure.

According to a second aspect a [c2] daisy chain dimer is described. The dimer comprises a first [c2] daisy chain macromer herein described comprising a first cap, a first binding site, a first backbone portion and a first recognition moiety wherein the first and second polyether chains of the first recognition moiety are linked one to another to form a first polyether crown. The [c2] daisy-chain dimer also comprises a second [c2] daisy chain macromer comprising a second cap, a second binding site, a second backbone portion and a second recognition moiety wherein the first and second polyether chains of the second recognition moiety are linked one to another to form a second polyether crown. In the [c2] daisy-chain dimer, the first [c2] daisy chain macromer and the second [c2] daisy chain macromer are interlocked.

The [c2] daisy-chain dimer herein described is capable of assuming an extended state and a contracted state. In the contracted state of the [c2] daisy-chain dimer, the first recognition moiety is coordinately bound to the second binding site and the second recognition moiety is coordinately bound to the first binding site. In the extended state of the [c2] daisy-chain dimer coordinated interactions between the first recognition moiety and the second binding site and between the second recognition moiety and the first binding site are minimized. In the [c2] daisy-chain dimer, switching between the extended state and contracted state is controllable upon removal or reinstatement, respectively of coordinating interactions between the binding sites and the recognition moieties.

According to a third aspect, a [c2] daisy-chain polymer is described. The polymer comprises two or more [c2] daisy-chain dimers herein described covalently linked one to the other to form a linear [c2] daisy chain polymer.

According to a fourth aspect, a composition is described that comprises at least one of the [c2] daisy-chain macromer, [c2] daisy-chain dimers and [c2] daisy-chain polymer herein described together with a suitable vehicle.

According to a fifth aspect, a material is described that comprises a [c2] daisy chain polymer herein described.

According to a sixth aspect, a method to provide a [c2] daisy-chain macromer is described. The method comprises: providing a linear backbone fragment comprising structurally rigid functionalities and having a first end and a second end; providing a binding site/cap fragment comprising a binding site portion and a cap portion; and providing a recognition fragment configured to provide a recognition moiety interlocked to the binding site.

The method further comprises: attaching the first end of the backbone fragment to the binding site portion of the binding site/cap fragment; and attaching the second end of the backbone fragment to the recognition fragment, to provide a [c2] daisy-chain macromer.

According to a seventh aspect, a method to actuate a [c2] daisy-chain dimer or polymer is described. The method comprises: providing a [c2] daisy-chain dimer or polymer herein described, the [c2] daisy-chain dimer or polymer capable to assume an extended state and a contracted state and controlling the state of the [c2] daisy-chain dimer or polymer by coordinating interactions between binding sites and recognition moieties within the [c2] daisy-chain dimer or polymer.

The macromers, dimers and polymers, herein described and related compositions, materials, methods, and systems allow in some embodiments to provide a stronger binding interactions between binding site and recognition moiety compared to other systems of the art that results in a particularly stable contracted state of the [c2] daisy chain dimers herein described.

The macromers, dimers and polymers, herein described and related compositions, materials, methods, and systems allow in several embodiments to provide a [c2] daisy chain dimer contracted state that can be used in connection with applications where a stable contracted The macromers, dimers and polymers, herein described and related compositions, materials, methods, and systems can be used in several embodiments in connection with applications wherein controlled switchable topology of a macromolecule is desirable, including but not limited to bioengineering with reference to applications such as artificial molecular muscles, extendible/contractible materials, expandable/shrinkable materials and self-healing materials. Additional applications comprise electronic applications (such as switches) and other nanosystems functions (such as nanovalves or nano bungee cords).

The details of one or more embodiments of the disclosure are set forth in the accompanying drawings and the detailed description and examples below. Other features, objects, and advantages will be apparent from the detailed description, examples and drawings, and from the appended claims

BRIEF DESCRIPTION OF THE DRAWINGS

The accompanying drawings, which are incorporated into and constitute a part of this specification, illustrate one or more embodiments of the present disclosure and, together with the detailed description and the examples, serve to explain the principles and implementations of the disclosure.

FIG. 11A and FIG. 11B show a reaction scheme for the production of a cap, production of a crown and production of a methyl ester recognition backbone fragment. FIG. 11C shows a reaction scheme for the production of an aldehyde recognition backbone fragment. FIG. 11D shows a reaction scheme for the production of a self complimentary Macromer (1-HPF6).

DETAILED DESCRIPTION OF PREFERRED EMBODIMENTS

Provided herein are interlocked molecules, and related macromers, materials compositions, methods and systems.

The term "interlocked" or "interlock" as used herein indicates a mechanical connection between molecules performed as a consequence of the molecules' topology. Typically, interlocked molecules consist of two or more separate molecular components, mechanically connected to form a spatial arrangement that prevents dissociation between the molecular components without breaking one or more chemical bonds (e.g. covalent bond) within the components. Molecules connected mechanically are analogous to links in chain. The individual links are not directly connected, but no one link can be separated from the others without breaking at least one link. On the molecular level the interlocked molecules cannot be separated without breaking of one or more covalent bonds in at least one the interlocked molecules. Examples of mechanically-interlocked molecular architectures include catenanes, rotaxanes, molecular knots, and molecular Borromean rings.

In particular, interlocked molecules provided herein are [c2]daisy-chain dimers and related polymers, comprising [c2]daisy-chain macromers that are configured to interlock following formation of covalent linkages within each macromer. In particular, interlocking between [c2]daisy chain macromers herein described is performed through formation of controllable coordinating bonds between predetermined moieties within each macromer, herein also indicated as binding site and recognition moiety.

The term "[c2]daisy chain dimer" or "DCD" as used herein indicates a structure comprised of two [c2]daisy chain macromers interlocked in such a fashion that a binding site of the first macromer is encircled by a recognition moiety of the second macromer, and, a binding site of the second macromer is encircled by a recognition moiety of the first macromer.

The term "[c2] daisy chain macromer" as used herein indicates a molecule containing a recognition moiety and a binding site covalently attached within a same molecule. In some embodiments, the binding site and the recognition moiety of one macromer can engage in coordinating interactions one with the other. In the macromers herein described the recognition moiety and the binding site of one macromer are capable to engage in cording interactions with the recognition moiety and binding site of another macromer respectively to form an interlocked DCD.

The term "attach" as used herein refers to connecting or uniting by a bond, link, force or tie in order to keep two or more components together, which encompasses either direct or indirect attachment where, for example, a first molecule is directly bound to a second molecule or material, or one or more intermediate molecules are disposed between the first molecule and the second molecule or material.

Figure 1:
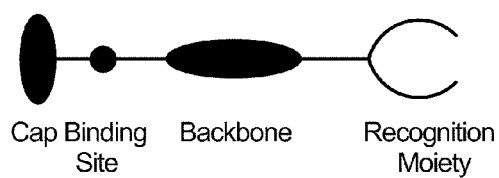
FIG. 1 shows a schematic representation of the structure of a macromer according to some embodiments of the present disclosure.

A [c2] daisy chain macromer herein described comprises a binding site, a recognition moiety, a backbone portion located between the recognition moiety and the binding site, and a cap portion located adjacent to the binding site and distant from the recognition moiety and the backbone In some embodiments to [c2] daisy chain macromer herein described comprises a binding site, a recognition moiety, a backbone portion and a cap portion attached one to the other according to the structural organization schematically illustrated in FIG. 1.

In the schematic illustration of FIG. 1, the binding site is located between the backbone and the cap, while the backbone is incorporated between the binding site and the recognition moiety. Furthermore, as schematically illustrated in FIG. 1, in [c2] daisy chain macromer herein described, the cap and recognition moiety are located on opposite ends of the macromer structure. In particular, in the macromer, the cap portion, the binding site, the backbone and the recognition moiety are attached together to form a linear [c2]daisychain macromer structure.

The term "binding" site as used herein indicates a moiety that is capable of engaging in controllable coordinated interactions with a corresponding recognition moiety. In [c2] daisy-chain macromers herein described the binding site is formed by a secondary amine covalently attached to the backbone portion and to the cap portion.

In some embodiments, the attachment between the binding site and the backbone portion and/or the cap portion of the macromer can be performed through direct covalent linkage between the amine of the binding site and a functional group of the backbone portion or the cap portion.

The term "functional group" as used herein indicates specific groups of atoms within a molecular structure that are responsible for the characteristic chemical interactions or reactions of that structure. Exemplary functional groups include hydrocarbons, groups containing halogen, groups containing oxygen, groups containing nitrogen and groups containing phosphorus and sulfur all identifiable by a skilled person. In particular, exemplary functional groups in the sense of the present disclosure comprise alkoxy or alkyl groups, olefins, polyether chains, secondary amines, and benzyl groups. Additional functional groups can be identified by a skilled person upon reading of the present disclosure. As used herein, the term "corresponding functional group" refers to a functional group that can interact with another functional group. Thus, functional groups that can interact with each other can be referred to as corresponding functional groups.

In some embodiments, the secondary amine comprises alkyl and/or aryl moieties and attachment of the secondary amine can be performed through binding of the alkyl and/or aryl moieties to the backbone portion or the cap portion. In particular in some embodiments attachment of the secondary amine to the backbone portion and/or cap portion can be independently performed through an optionally substituted alkyl, alkaryl, aralkyl aralkyloxy or alkaryloxy moiety covalently bound to a corresponding functional group on the backbone portion and/or cap portion.

In particular in some embodiments, the secondary amine comprises a linear alkyl moiety having 1 to 3 carbon atoms covalently bound to the cap portion or backbone portion.

In some embodiments, the secondary amine comprises a single ring aryl moiety binding the amine and the backbone portion or the cap portion in meta or para positions, with the single ring aryl moiety optionally substituted with an alkyl, aryl or alkoxy group. In some embodiments, the single ring aryl moiety is a benzyl moiety optionally meta substituted with an alkyl, aryl or an alkoxy group. In some of those embodiments, the benzyl group can contain a heteroatom at the meta or para position.

In some embodiments, the secondary amine comprises a double ring aryl moiety binding the amine with the backbone portion or the cap portion at positions that minimize the interactions between the secondary amine and the corresponding recognition moiety in the [c2]daisy chain macromer. In particular in some embodiments, the secondary amine comprises a double ring aryl moiety binding the amine with the backbone portion or the cap portion at distal positions of the double ring aryl moiety.

In some embodiments, possible counterions for the ammonium functionality of the secondary amine of a [c2] daisy chain macromer herein described comprise trifluoroacetate, chloride, bromide, iodide, hexafluorophosphate, triflate, and tetrakis[3,5-bis(trifluoromethyl)phenyl]borate and additional counterions identifiable by a skilled person.

In [c2] daisy chain macromer herein described the binding site formed by the secondary amine is capable of engaging in coordinating interactions with a corresponding recognition moiety.

The term "recognition moiety" as used herein generally indicates any moiety that is capable of engaging in coordinated interactions with a corresponding binding site. In particular, in a [c2]daisy chain macromer herein described, the recognition moiety can engage in electrostatic interactions with the secondary amine forming the binding site of a second macromer to properly orient the two macromers for the subsequent interlocking intramacromer covalent bond-forming reaction.

In [c2]daisy-chain macromer herein described the recognition moiety comprise two polyether chains including two to four oxygen atoms and presenting a terminal or internal olefin configured to allow metathesis between the two polyether chains of a same macromer.

The term "present" as used herein with reference to a compound or functional group indicates attachment performed to maintain the chemical reactivity of the compound or functional group as attached. Accordingly, a functional group presented on a moiety, is able to perform under the appropriate conditions the one or more chemical reactions that chemically characterize the functional group. In particular, an olefin presented on one polyether chain is able to perform under the appropriate conditions the metathesis reaction, typically ring-closing metathesis, that allow binding of the olefin with an olefin presented on the other polyether chain of the same macromer.

In the recognition moiety, each of the polyether chains includes corresponding terminal or internal olefin presented on the polyether chain and capable to bind to each other to form a polyether crown thus interlocking the recognition moiety and the binding site.

In some embodiments, in a recognition moiety of a [c2] daisy chain macromer the two polyether chains can have a same or different chemical structure.

In some embodiments, the polyether chains independently include 1 to 3 carbons between adjacent oxygens in the chain. In particular, in some embodiments, at least one, and possibly both polyether chains, comprise 2 carbons between at least one of the pairs of adjacent oxygens in the chain.

In [c2] daisy chain macromers herein described the recognition moiety typically includes a linking moiety formed by an optionally substituted aryl or alkyl group linking the recognition moiety to the backbone portion of the macromer.

In particular, in some embodiments, attachment of the recognition moiety to the backbone portion is performed through a oxygen or sulfur heteroatom linkage, or via an alkyl chain having 1 to 4 carbon atoms. In some embodiments, attachment of the recognition moiety to the backbone portion is performed through an alkoxy group or a heteroatom containing alkyl or aryl group, with the total length of the chain between the backbone and the recognition moiety not to exceed 6 covalent bonds.

In some embodiments, the recognition moiety is an aryl polyether fragment, which comprises an aryl moiety attaching two polyether chains at adjacent carbons of an aryl ring (ortho positions). In particular, in some embodiments, the aryl moiety is formed by a single aromatic ring comprising six carbon atoms.

In some embodiments the terminal olefins are located no less than three carbons from the last oxygen of the polyether chain.

In some embodiments, the olefins presented in the polyether chains of the recognition moiety are terminal olefins. The term "terminal" as used herein indicates an olefin or other functional group located at the termini of a chain or other group.

In some embodiments, the olefins presented in the polyether chains of the recognition moiety are internal 1,2-disubstituted olefins configured to enable metathesis reaction of the internal olefin of one chain with the internal or terminal olefin of the other chain of a same macromer.

In [c2] daisy chain macromer herein described, the binding site and recognition moiety are selected so that the association constant ($K_a$) governing interactions between the recognition moiety and the binding site is equal to or more than about 75 $M^{-1}$. The association constant can be measured using various techniques identifiable by a skilled person upon reading of the present disclosure including for example the techniques and procedures described in: Fielding, Lee. *Tetrahedron* 2000, 56, 6151-6170 herein incorporated by reference in its entirety as well as other procedures identifiable by a skilled person.

In [c2] daisy chain macromers herein described the recognition moiety is attached to the binding site through a backbone portion.

The term "backbone" as used herein indicates a rigid structure covalently attaching the binding site with the recognition moiety. In particular, in several embodiments the [c2] daisy chain macromer herein described comprises a backbone portion located between the binding site and the recognition moiety, wherein the backbone comprises structurally rigid functionalities configured to minimize intramolecular interactions between the recognition moiety and the binding site.

The term "structurally rigid functionality" as used herein indicates an inability of a functional group or structure to bend. Exemplary structurally rigid functionalities include structures with $sp^2$-hybridized carbons throughout the length of the structure. In some embodiments, the structurally rigid functionalities can be formed by substituted or unsubstituted aryl moieties. In particular, in some embodiments, suitable functionalities include functionalized biphenyl structures, such as terminally functionalized naphthalene, anthracene, or naphthacene, and additional aromatic structures identifiable by a skilled person upon reading of the present disclosure, linking the recognition moiety and the binding site in distal positions of the structure.

In some embodiments, the structurally rigid functionality is selected to promote dimer preassembly via macromer-macromer π-π slipped-stacking interactions, and enhance the linearity of the dimer, aiding elongation via slippage of the rod-like backbone through the closed crown ether-type rings.

In some embodiments, linking of the backbone structure to the binding site and the recognition moiety can be achieved through heteroatom linkages, alkyl and/or alkoxy chain. In particular in some embodiment, heteroatom linkages are provided by oxygen or sulfur linkages, the alkyl chains include 1 to 6 carbon atoms, and the alkoxy chain includes 1 to 3 (—O—C—) moieties.

The [c2] daisy chain macromer herein described also comprises a cap portion adjacent to the binding site.

The term "cap portion" as used herein indicates a structure that prevents two interlocked [c2] daisy chain macromers herein described, by sterically blocking an encircling recognition moieties from unthreading off of the encircled backbone/binding site.

In some embodiments, the cap is a substituted cyclic alkyl ring comprising 6 to 10 carbons: Exemplary cap structures include a 3,5 substituted 6-membered alkyl ring, a 2,5 or 3,4 substituted 7-membered alkyl ring, a 2,5 or 4,6 substituted 8-membered alkyl ring, a 9-, 10-, 11-, 12-, 13-, or 14-membered alkyl ring substituted in any position. In some embodiments, the substituents can be an aryl, alkyl or alkoxy group, and in particular can be formed by a linear or branched alkyl chains having 1 to 10 carbons. In some embodiments, the cap portion can be formed by an aryl moiety possibly substituted with one or more alkyl and/or an aryl groups, wherein the aryl moiety is configured to constrain movements of a recognition moiety interlocked to the binding site.

In some embodiments, the aryl moiety is formed by a substituted benzyl ring attaching in a 1,4 substitution (para) pattern a first and second functional groups. The first functional group can be formed by a heteroatom (e.g. oxygen or nitrogen or sulfur), or by a linear alkyl chain of variable length from 1 to 10 carbon atoms, with terminal functionality derived from oxygen, including alcohol, ether, or ester functional groups, or those derived from nitrogen, such as amine, amide, or imine functional groups. The second functional group can be formed by a heteroatom (e.g. oxygen or nitrogen or sulfur), or linear alkyl chain of variable length from 1 to 10 carbons with terminal functionality derived from oxygen, including alcohol, ether, or ester functional groups.

In some of those embodiments, the substituted benzyl ring of the cap portion can attach two additional functionalities either in the 2,6- or 3,5-substitution pattern formed by a number of different functional classes. Viable alkyl substituents include ethyl, isopropyl, butyl (and all isomers), pentyl (and all isomers), adamantly, or thexyl. Viable aryl substituents include phenyl or mesityl. Viable alkoxy substitutents include methoxy, ethoxy, propoxy (and all isomers), butoxy (and all isomers), pentoxy (and all isomers), and phenoxy.

In some embodiments the [c2] daisy chain macromer herein described further comprises a stopper moiety wherein the stopper moiety or protecting group in a first [c2]daisy chain macromer indicates a moiety selected and located on the first [c2]daisy chain macromer to minimize movements of a recognition moiety of a second [c2]daisy chain macromer encircling the backbone portion of the first [c2]daisy chain macromer when the first [c2]daisy chain macromer and the second [c2]daisy chain macromer are interlocked to form a [c2]daisy chain dimer herein described.

In some embodiments, the stopper moiety is a moiety attached to the nitrogen of the binding site of a macromer, and can be comprised, for example, of an acyl functionality, tert-butyl carbamate functionality, or other protecting group as identifiable by a skilled person upon reading of this disclosure. In some embodiments, the stopper moiety can be selected to sterically prevent passage of the encircling crown ether recognition moiety when the [c2]daisy chain dimer is in an extended state as described in the present disclosure.

In some embodiments the [c2] daisy chain macromer structure is a molecule of formula (I)

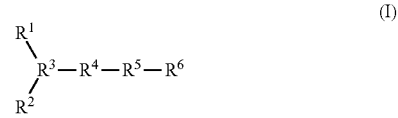

wherein R1, R2, R3, R4, R5 and R6 are independently defined as follows.

In the [c2] daisy chain macromer of formula (I), R1 and R2 are independently a polyether chain of formula (II)

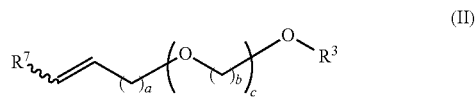

wherein
R7 is a hydrogen or a linear carbon chain having 1 to 3 carbon atoms,
a is 2 to 5
b is independently 1 to 3 for each iteration of the carbon oxygen moiety
c is 1 to 3.

In the [c2] daisy chain macromer of formula (I), $R^3$ is a linking moiety covalently attached to moieties $R^1$ and $R^2$, as well as the backbone moiety $R^4$, which the linking moiety $R^3$ can have formula (III), (IV) (V), (VI), (VII), (VIII) or (IX)

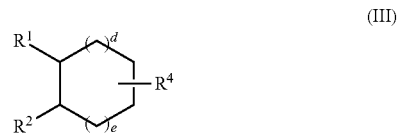

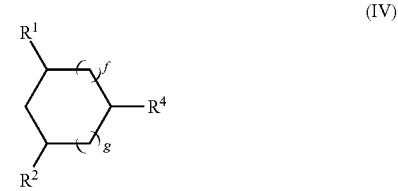

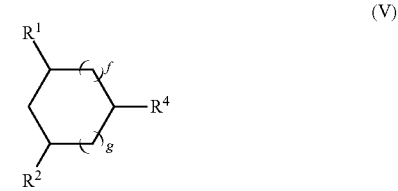

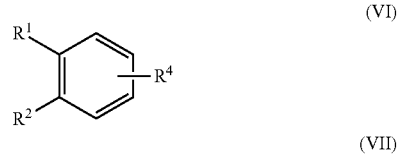

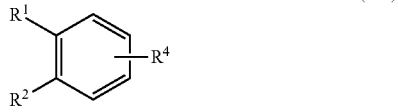

-continued

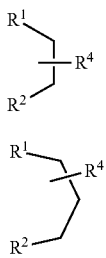
(VIII)

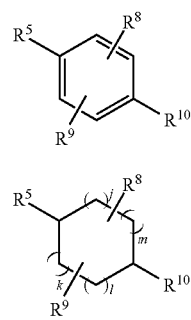
(XIII)

(IX)

(XIV)

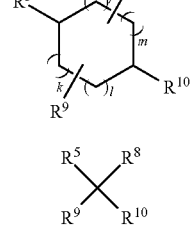

(XV)

wherein
  d is 1 to 3,
  e is 1 to 3,
  f is 1 to 3, and
  g is 1 to 3.

In the [c2] daisy chain macromer of formula (I), $R^4$ is a backbone fragment which is covalently attached to the linking fragment $R^3$ and to the binding site $R^5$, which $R^4$ fragment having formula (X) or (XI)

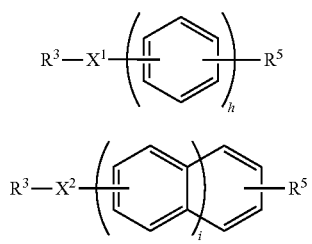
(X)

(XI)

wherein
  $X^1$ and $X^2$ are a linear or branched, optionally heteroatom containing, alkyl chain having 1 to 4 carbons, wherein the heteroatom is oxygen or sulfur
  h is to 1-3 and
  i is 1 to 3.

In the [c2] daisy chain macromer of formula (I), $R^5$ is a binding site that is covalently attached to the backbone fragment R4 and the cap fragment $R^6$, which binding site $R^5$ is a compound of formula (XII)

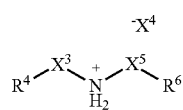
(XII)

$X^3$ and $X^5$ are independently a linear alkyl chain having 1 to 3 carbons, a single ring aryl moiety linking N and $R^4$ in meta or para positions, an aryloxy or an aralkoxy group, and $X^4$ is a negative charged species that can engage in attractive ionic interactions with the positively charged ammonium binding site, such as trifloroacetate, Chloride, Bromide, Iodide, Hexafluorophosphate, Triflate, tetrakis[3,5-bis(trifluoromethyl)phenyl]-borate or any additional counterions identifiable by a skilled person.

In the [c2] daisy chain macromer of formula (I), $R^6$ is a cap fragment that is covalently attached to the binding site $R^5$, which $R^6$ cap fragment has formula (XIII), (XIV) or (XV)

wherein
  $R^8$ and $R^9$ are independently an alkyl, alkoxy, or an aryl group,
  $R^8$ can be covalently attached to any carbon of the j alkyl chain or the m alkyl chain
  $R^9$ can be covalently attached to any carbon of the k alkyl chain or the l alkyl chain
  $R^{10}$ is an H, or a linear or branched alkyl chain having 1 to 20 carbon atoms having a terminal functional group, e.g. amine, alcohol, thiol, or carboxylic acid
  j is 0 to 3,
  k is 0 to 3,
  l is 0 to 3, and
  m is 0 to 3.

In some embodiments, in a [c2] daisy chain macromer herein described of formula (I) at least one of $R^1$ and $R^2$ is a compound of formula (II) wherein b is 2 and is the same for each iteration of the carbon oxygen chain. In some of those embodiments, c is 2.

In some embodiments, in a [c2] daisy chain macromer herein described of formula (I) $R^1$, $R^2$ and $R^3$ form together a compound of formula (XVI)

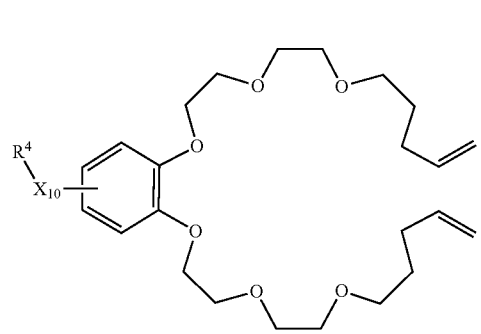
(XVI)

wherein
  X10= is —O—, an alkyl chain (—CH2-)q, or S, and
  q is 1 to 3.

In some embodiments, in a [c2] daisy chain macromer herein described of formula (I) $R^4$ is a compound of formula (XVII) or (XVIII)

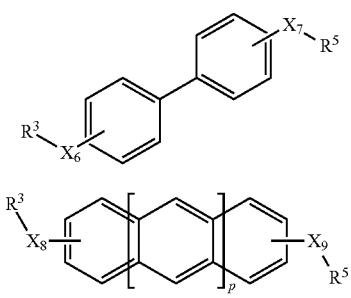

(XVII)

(XVIII)

wherein $X^6$, $X^7$, $X^8$, and $X^9$ are independently —O—, —CH2-, or —S— and p is 0 to 3.

In some embodiments, in a [c2] daisy chain macromer herein described of formula (I) $R^4$ is a compound of formula (XVII) or (XVIII) wherein $X^6$, $X^7$, $X^8$ and $X^9$ are $CH_2$ and P is 0 or 1.

In some embodiments, in a [c2] daisy chain macromer herein described of formula (I) $R^5$ is a compound of Formula (XII) wherein $X^3$ and $X^4$ are independently an optionally substituted aryl moiety, —$CH_2$—, —O—, or —S—, n is 1 to 10, and $X^4$ is Trifloroacetate, Chloride, Bromide, iodide, Hexafluorophosphate, Triflate, tetrakis[3,5-bis(trifluoromethyl)phenyl]-borate, or other counterions identifiable by a skilled person.

In some embodiments, in a [c2] daisy chain macromer herein described of formula (I) $R^5$ is a compound of Formula (XII) wherein $X^3$ and $X^4$ are independently a benzyl moiety optionally meta substituted with an alkyl group, an aryl group and/or an alkoxy group.

In some embodiments, in a [c2] daisy chain macromer herein described of formula (I) $R^6$ is a compound of formula (XIX)

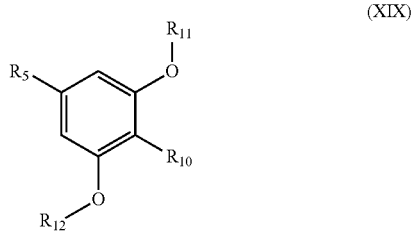

(XIX)

wherein $R^{11}$ is an alkyl, group, and in particular a linear or branched alkyl group having 1 to 10 carbon atoms, and $R^{12}$ is an aryl group and in particular an optionally substituted single ring aryl moiety.

In some embodiments, the binding site $R^5$ is a compound of formula (XX)

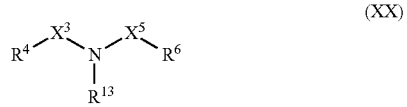

(XX)

wherein $X^3$ and $X^5$ have the same meaning of Formula (XII), and $R^{13}$ can be an alkyl group of no less than 3 carbons, a carbamate containing alkyl or aryl substituents or a combination thereof, an acyl group, or other amine protecting group identifiable by a skilled person (for other examples, see e.g. Protective Groups in Organic Synthesis, T. W. Greene and P. G. M. Wuts, 3rd Edition, pp. 494-653).

In some embodiments, the macromer is formed by structurally rigid $R^4$ between the binding site $R^5$ and the recognition moiety formed by $R^1$, $R^2$ and $R^3$ moieties, wherein the structurally rigid $R^4$ is incorporated to minimize the formation of self-complexed monomer, promote dimer preassembly via macromer-macromer π-π slipped-stacking interactions, and enhance the linearity of the dimer, aiding elongation via slippage of the rod-like backbone through the closed crown ether-type rings. An exemplary macromer having the above features is 1-H.PF6 synthesized as further described in the examples section. Treatment of self-complementary macromer 1-H.PF6 with olefin metathesis catalyst (H2IMes)(PCy3)(Cl)2RudCHPh (2) furnished the desired interlocked DCD 3-H2·2PF6 in 71% isolated yield.

[c2] daisy chain macromer here described can be mechanically linked together to form a [c2] daisy chain dimer. The term "[c2] daisy chain dimer" as used herein indicates a structure comprised of two interlocked daisy chain macromers herein described wherein the two polyether chain within each macromer covalently bound to form a polyether crown encircling the binding site or backbone portion of the other macromer.

For example, in some embodiments, the dimer can be formed by a first macromer of formula (I) comprising R1'R2'R3'R4'R5'R6' moieties, and a second macromer of formula (I) comprising R1"R2"R3"R4"R5"R6" moieties wherein R1' and R1" have independently the same meaning of R1, R2' and R2" have independently the same meaning of R2, R3' and R3" have independently the same meaning of R3, R4' and R4" have independently the same meaning of R4, R5' and R5" have independently the same meaning of R5, R6' and R6" have independently the same meaning of R6. In those embodiments, the first and second macromer can be interlocked together in such a way that the backbone portion (R4') or binding site (R5') of the first macromer is encircled by the recognition moiety (R1", R2", R3") of the second macromer where the polyether chains R1" and R2" are linked to form a polyether crown and the backbone portion (R4") or binding site (R5") of the second macromer is encircled by the recognition moiety (R1', R2', R3') of the first macromer where the polyether chains R1' and R2' are linked to form a polyether crown.

In some embodiments, the structurally rigid functionality is selected to promote dimer preassembly via macromer-macromer π-π slipped-stacking interactions, and enhance the linearity of the dimer, aiding elongation via slippage of the rod-like backbone through the closed crown ether-type rings.

In some embodiments, two [c2] daisy chain macromers can be interlocked to form a [c2] daisy chain dimer herein described via formation of a covalent bond between the two terminal or internal olefins on each recognition moiety after the two macromers have assembled in solution as directed by the electrostatic interactions between the recognition moieties and binding sites of the partnered macromers.

Figure 2:
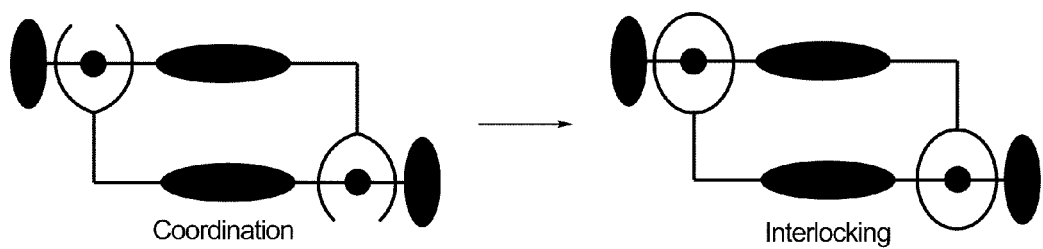
FIG. 2 shows a schematic representation of coordination and interlocking of a macromer to form dimmer according to some embodiments of the present disclosure.

A schematic illustration of a suitable process for formation of a bond between the binding site and the recognition moiety as schematically shown in the illustration of FIG. 2.

The illustration of FIG. 2, schematically shows the synthesis of a [c2] daisy-chain dimer involves the coordinating and interlocking of two self-complementary macromers. The wording "self-complementary macromers" as used herein indicates a first and second macromers wherein the binding site and recognition moiety of a first macromer are capable to form under appropriate conditions coordinating interactions respectively with the recognition moiety and binding site of the second macromers. In particular, self-complementary macromers comprise first and second macromers having the same chemical structure, and first and second macromers having a different chemical structure.

In particular, in the illustration of FIG. 2, contacting of two self complementary macromers performed results in coordination of the two self complementary macromers as directed by electrostatic interactions between the recognition moieties and binding sites of the two macromers and, following a suitable reaction between the two polyether chains of each self complementary macromers, in interlocking of the two self-complementary macromers.

In some embodiments, two [c2] daisy chain macromers can be interlocked to form a [c2] daisy chain dimer herein described via formation of a covalent bond between the two terminal or internal olefins on each recognition moiety after the two macromers have assembled in solution as directed by the electrostatic interactions between the recognition moieties and binding sites of the partnered macromers, in presence of a suitable metathesis catalyst.

Figure 3A:
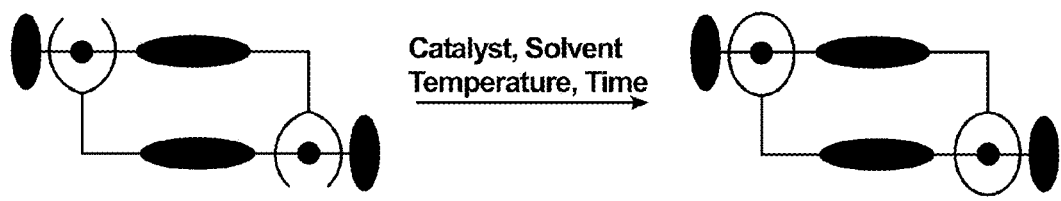
FIG. 3 shows a schematic representation of a general macromer dimerization reaction according to some embodiment herein described. In particular, FIG. 3A schematically illustrates the coordinating and interlocking of self-complementary macromers according to some embodiments herein described.
FIG. 3B schematically illustrates interlocking performed according to some embodiments herein described.
Figure 3B:
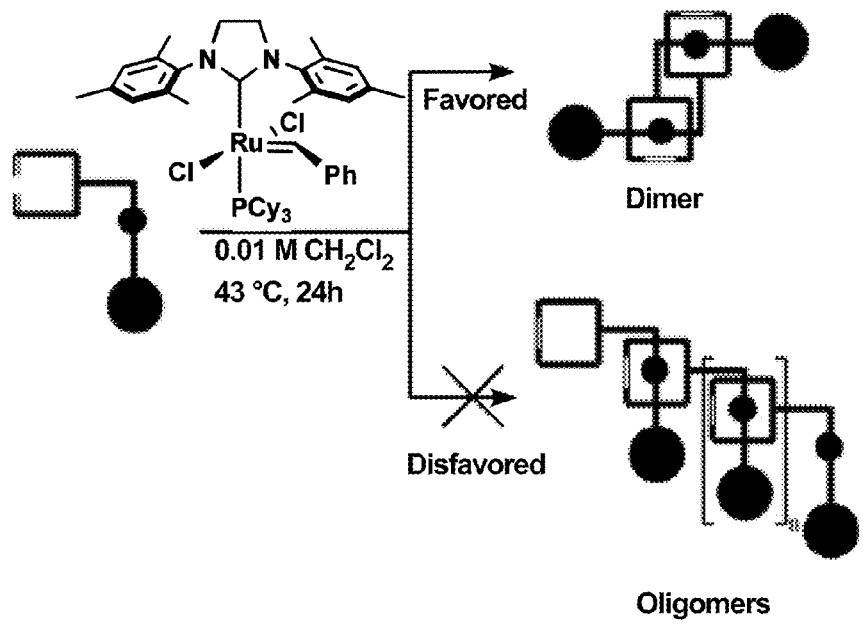

In some embodiments, illustrated in the schematic representation of FIG. 3A, contacting performed in presence of a suitable metathesis catalyst, results in interlocking of the two self complementary macromers following metathesis reactions between the olefins of the two polyether chains within each of the first and second macromer. In particular, in several embodiments, use of suitable metathesis catalysts typically results in favoring interlocking of two self-complementary macromers in a [c2]daisy chain dimer herein described, as schematically shown in the illustration of FIG. 3B, wherein one exemplary suitable catalyst is shown.

Figure 4:
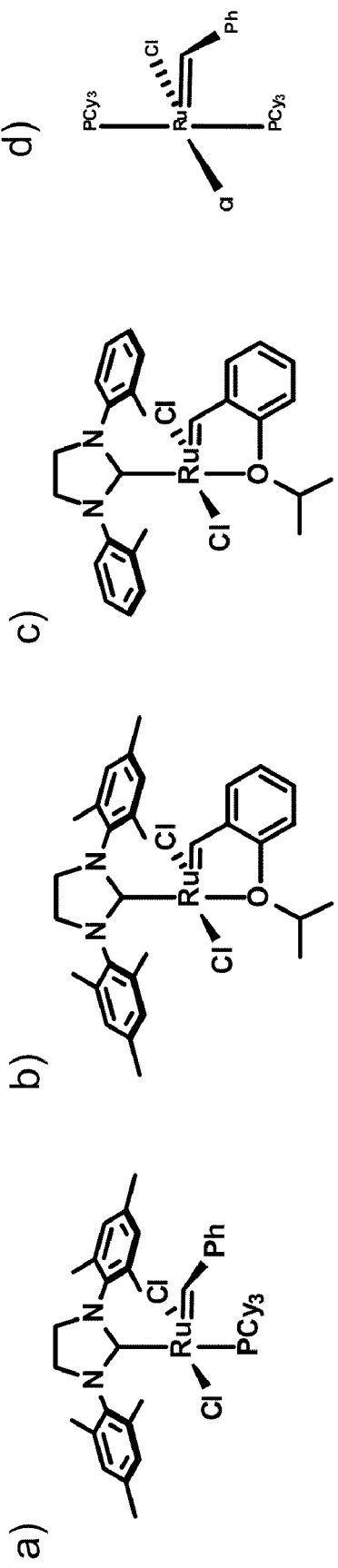
FIG. 4 shows exemplary suitable catalysts for ring-closing olefin metathesis interlocking reaction according to some embodiments of the present disclosure.

Additional, suitable catalysts comprise $(H_2IMes)(PCy_3)(Cl)_2Ru=CHPh$ (a), $(H_2IMes)(Cl)_2RuCH(o-OiPrC_6H_4)$ (b), and (c), and d) $(PCy_3)_2(Cl)_2Ru=CHPh$ as seen in FIG. 4. Further suitable catalysts include metathesis catalysts described in the following literature papers (see Vougioukalakis, G. C.; Grubbs, R. H. Chem. Rev. ASAP, Dec. 14, 2009) each incorporated herein by reference in its entirety.

Exemplary suitable solvents comprise dichloromethane (see Examples section), toluene, chloroform, dichloroethane, tetrahydrofuran, ethyl ether, toluene, benzene, dimethyl carbonate, and tent-butyl methyl ether and mixes of these solvents capable to solubilize the specific macromer that is dimerized. Additional suitable solvents are identifiable by a skilled person upon reading of the present disclosure including (see Vougioukalakis, G. C.; Grubbs, R. H. Chem. Rev. ASAP, Dec. 14, 2009; Kuhn, K. M.; Champagne, T. M.; Hong, S. H.; Wei, W.-H.; Nickel, A.; Lee, C. W.; Virgil, S. C.; Grubbs, R. H.; Pederson, R. L Org. Lett. ASAP, Feb. 8, 2010; Kuhn, K. M; Bourg, J.-B.; Chung, C. K.; Virgil, S. C.; Grubbs, R. H. J. Am. Chem. Soc. 2009, 131, 5313) each incorporated herein by reference in its entirety.

In some embodiments, dimerization of [c2] daisy chain macromer herein described can be performed using reaction conditions that allow controlling performance of ring closing metathesis reaction through use of suitable macromer concentrations of 0.001M to, possibly, neat if the monomer is liquid (for suitable concentrations, see the previous reference Kuhn, K. M.; Champagne, T. M.; Hong, S. H.; Wei, W.-H.; Nickel, A.; Lee, C. W.; Virgil, S. C.; Grubbs, R. H.; Pederson, R. L Org. Lett. ASAP, Feb. 8, 2010) as will be understood by a skilled person in view of the features of the ring closing metathesis. Exemplary concentrations would be 0.005 to 0.02 M. Additional concentrations and/or reactions conditions that are suitable for performing ring closing metathesis for [c2] daisy chain macromers of the present disclosure are described, for example, in Vougioukalakis, G. C.; Grubbs, R. H. Chem. Rev. ASAP, Dec. 14, 2009; Kuhn, K. M.; Champagne, T. M.; Hong, S. H.; Wei, W.-H.; Nickel, A.; Lee, C. W.; Virgil, S. C.; Grubbs, R. H.; Pederson, R. L Org. Lett. ASAP, Feb. 8, 2010; Kuhn, K. M; Bourg, J.-B.; Chung, C. K.; Virgil, S. C.; Grubbs, R. H. J. Am. Chem. Soc. 2009, 131, 5313 and in additional references identifiable by a skilled person.

For example, in some embodiments, the reaction can be run with from about 0.05M to about 0.001M, and in particular 0.01 M of macromer per liter of suitable solvent. In some embodiments, the temperature of the reaction can be comprised between about 60° C. and about 0° C. In some embodiments, the reaction can be run for a time comprised between about 12 h and about 24 h. In several embodiments the catalyst loading can vary from about 1 mol % (relative to macromer) to about 10 mol %, or other loadings as identified in references (see e.g. Kuhn, K. M; Bourg, J.-B.; Chung, C. K.; Virgil, S. C.; Grubbs, R. H. J. Am. Chem. Soc. 2009, 131, 5313.) Quenching of the catalyst can be performed using excess ethyl vinyl ether or additional reagents identifiable by a skilled person.

In some embodiments, a [c2] daisy chain dimer herein described can be synthesized by threading an ammonium-containing fragment of a first macromer through the dibenzo-24-crown-8 ether or other recognition moiety of a second self-complementary macromer followed by a capping reaction, wherein a cap portion is attached to the threaded ammonium containing fragment of the first macromer to prevent dethreading of the resulting dimer. In some of those embodiment, [c2] daisy-chain dimers are produced in good yield. In some embodiments, a second binding site, typically able to form weaker (lower Ka) coordinating interactions with the recognition moiety of the self-complementary macromer can be introduced in the ammonium containing fragment of the first macromer before capping.

Figure 5:
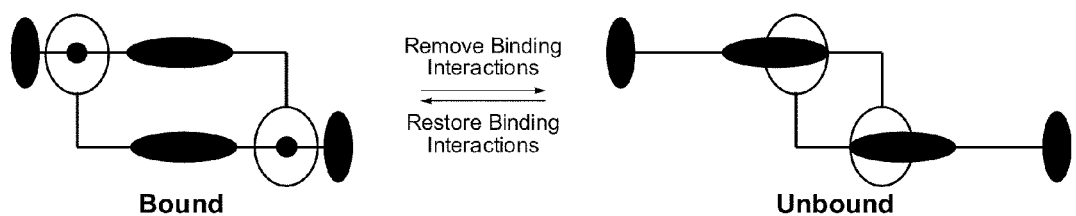
FIG. 5 shows a schematic representation of the "switching" of dimer between "bound" and "unbound" conformations upon introduction of an appropriate trigger according to some embodiments of the present disclosure.

The [c2] daisy-chain dimer herein described is able to assume an extended state and a contracted state as schematically illustrated in FIG. 5.

In particular, as shown in the schematic illustration of FIG. 5, in the [c2] daisy-chain dimer, switching between the extended state and contracted state is controllable upon removal or reinstatement of coordinating interactions between the binding sites and the recognition moieties. In particular, suitable reactions are reactions that render the first and second binding sites incapable of binding to the second or first recognition moieties, respectively, so that the dimer structure switches from the contracted state to the extended states due to sliding of the first and second backbones through the second and first recognition moieties, respectively.

In some embodiments, controllable switching between contracted to extended state can be performed by deprotonating the ammonium of the macromer binding site using suitable deprotonating reactions. Exemplary procedures that allow deprotonation of the ammonium of the macromer's binding site, comprise dissolving the dimer (or polymer comprising dimeric units) in a suitable solvent (e.g. dichloromethane, methanol, acetonitrile, nitromethane, or toluene) at from about 5.0 M to about 0.01 M concentration and contacting the dimer with at least three equivalents of a suitable base per dimer unit. Suitable bases can be identified by a skilled person based on the structure of the binding site and comprises aqueous solutions of potassium hydroxide, sodium hydroxide, or potassium carbonate, organic-soluble base such as phosphazene bases, 1,8-Diazabicyclo[5.4.0]undec-7-ene, or imidazole, or suspended solid bases such as sodium hydride or sodium amide, and additional bases identifiable by a skilled person.

In some embodiments, controllable switching between extended to contracted state can be performed by reprotonating the ammonium of the macromer binding site using suitable reprotonating reactions. Exemplary suitable reprotonation reactions for the amines of the dimer or dimeric units in the polymer can be achieved by addition of acid to a solution of deprotonated dimer or dimer-containing polymer in suitable solvents identifiable by a skilled person upon reading of the present disclosure. Exemplary suitable acids able to effect the reprotonation comprise: hydrochloric acid, trifluoroacetic acid, and hydrogen hexafluorophosphate.

Figure 6:
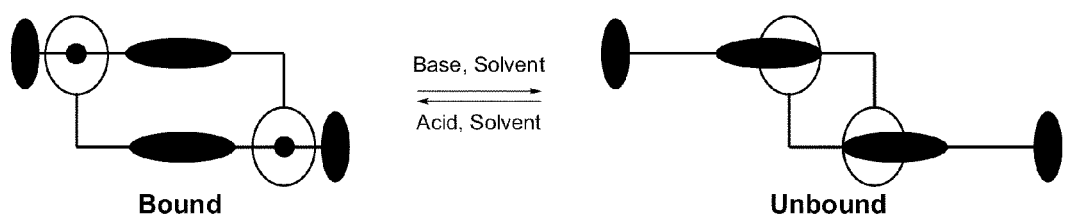
FIG. 6 shows a schematic representation of the switching of dimer from bound to unbound confirmations and subsequent rebinding upon addition of appropriate triggers according to some embodiments herein described.

All deprotonation/reprotonation switching reactions can be run at a temperature from about 0° C. to about 60° C. In some embodiments reaction times do not exceed 1 h, but usually can occur instantaneously. Additional conditions are identifiable to a skilled person upon reading of the present disclosure (see schematic illustration of FIG. 6).

In some embodiments, the switching can be performed by way of protection and deprotection of the amine of a macromer binding site with a stopper moiety or protecting group (e.g. an acyl group). In particular, in an exemplary embodiment, a protecting group can be introduced on a binding site of a dimer in an extended state to suitably block the recognition moiety from sliding from the backbone portion toward the binding site thus blocking the switching to a contracted state. In some of those embodiments, removal of the protecting group can be performed to allow switching from the extended state to a contracted state under appropriate conditions reinstating the coordinating interactions between binding site and recognition moiety. In embodiments wherein a protecting group is introduced on a [c2]daisy chain macromer to prevent switching from a state to another when the macromer is comprised in a dimer herein described, introduction of the protecting group and related switching prevention, can be reversible or irreversible.

Exemplary suitable protecting groups and suitable procedure for reversibly or irreversible introducing protecting groups on [c2]daisy chain macromers are described in Protective Groups in Organic Synthesis, T. W. Greene and P. G. M. Wuts, 3rd Edition, pp. 494-653 herein incorporated by reference in its entirety. Additional groups and procedures are identifiable by a skilled person upon reading of the present disclosure.

Figure 7:
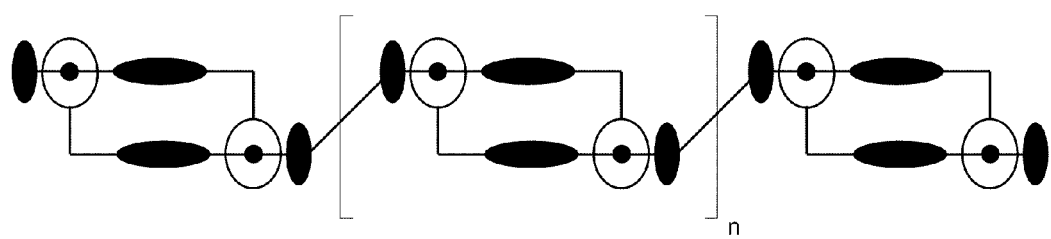
FIG. 7 shows a schematic representation of a linear polymer with [n+2] dimeric units incorporated in a main-chain fashion according to some embodiments of the present disclosure.

In some embodiments, the DCD dimers are covalently joined to form a [c2] daisy-chain polymer as schematically illustrated in FIG. 7.

The term "[c2] daisy chain polymer" as used herein indicates a polymer that contains the interlocked daisy-chain dimer units wherein the dimer units within a same polymer have the same or different chemical structure. In some embodiments, the DCD are linked in line of the polymer backbone (main-chain DCD polymer). In some embodiments, DCD are attached in a perpendicular fashion off of the backbone (side-chain DCD polymer). In embodiments wherein DCDs are polymerized in a main-chain fashion, the length of the polymer chain is dependent on the extended or contracted conformation of the contained DCD structures (FIG. 7).

Figure 8:
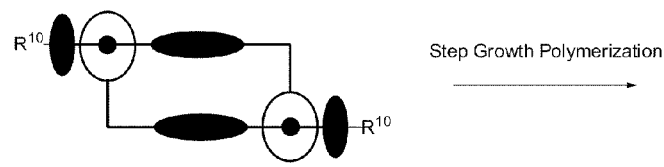
FIG. 8 shows a reaction scheme for a general dimer polymerization performed according to some embodiments herein described.
Figure 8:
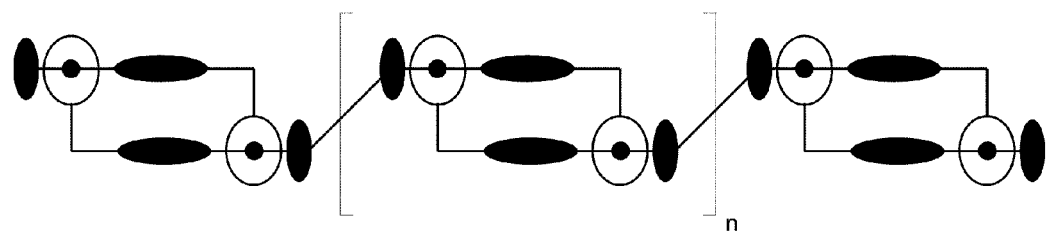
Figure 9:
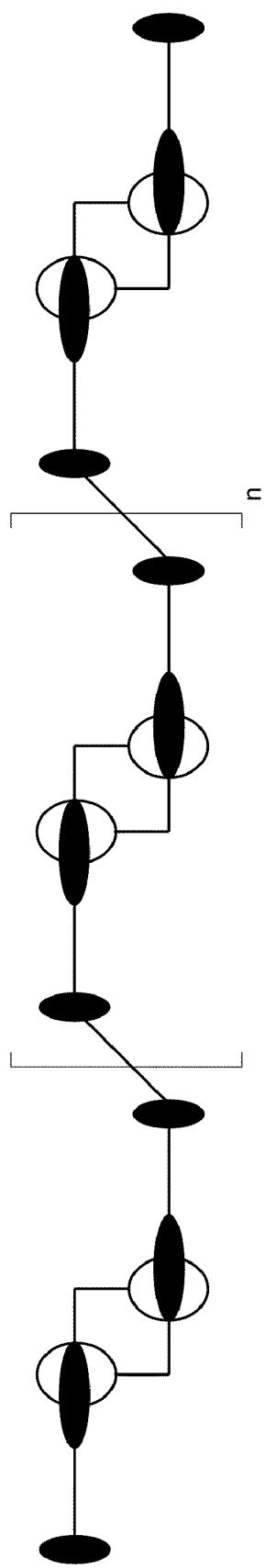
FIG. 9 shows an extension of dimer units within the polymer, increasing the polymer dimensions according to some embodiments herein described.
Figure 10:
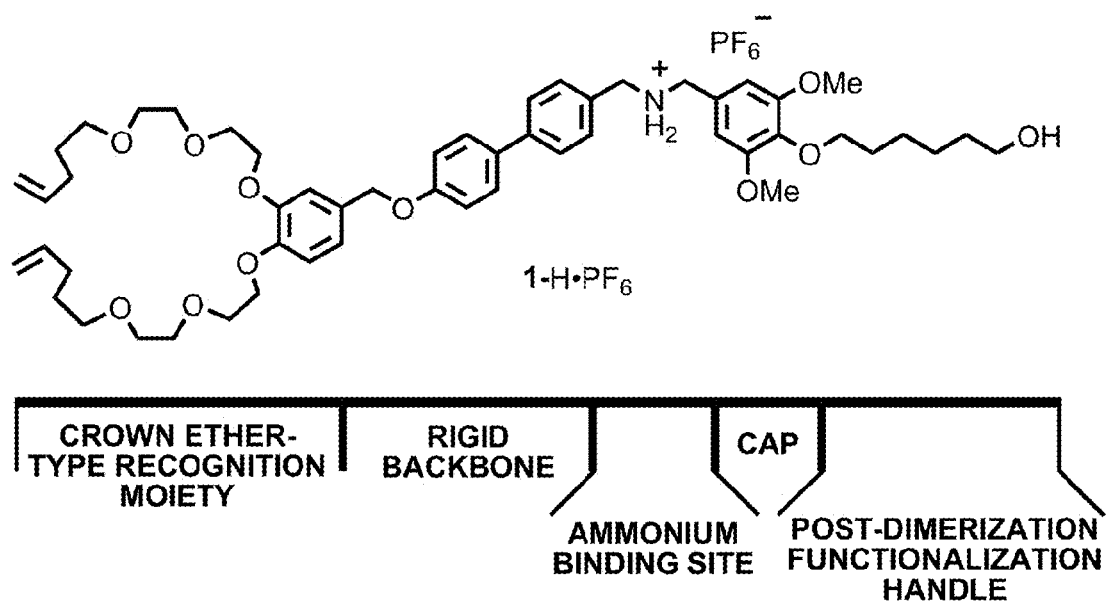
FIG. 10 shows the formula of a macromer according to an embodiment of the present disclosure shown together with a schematic representation of the key features and overall structural design of the macromer.
Figure 11A:
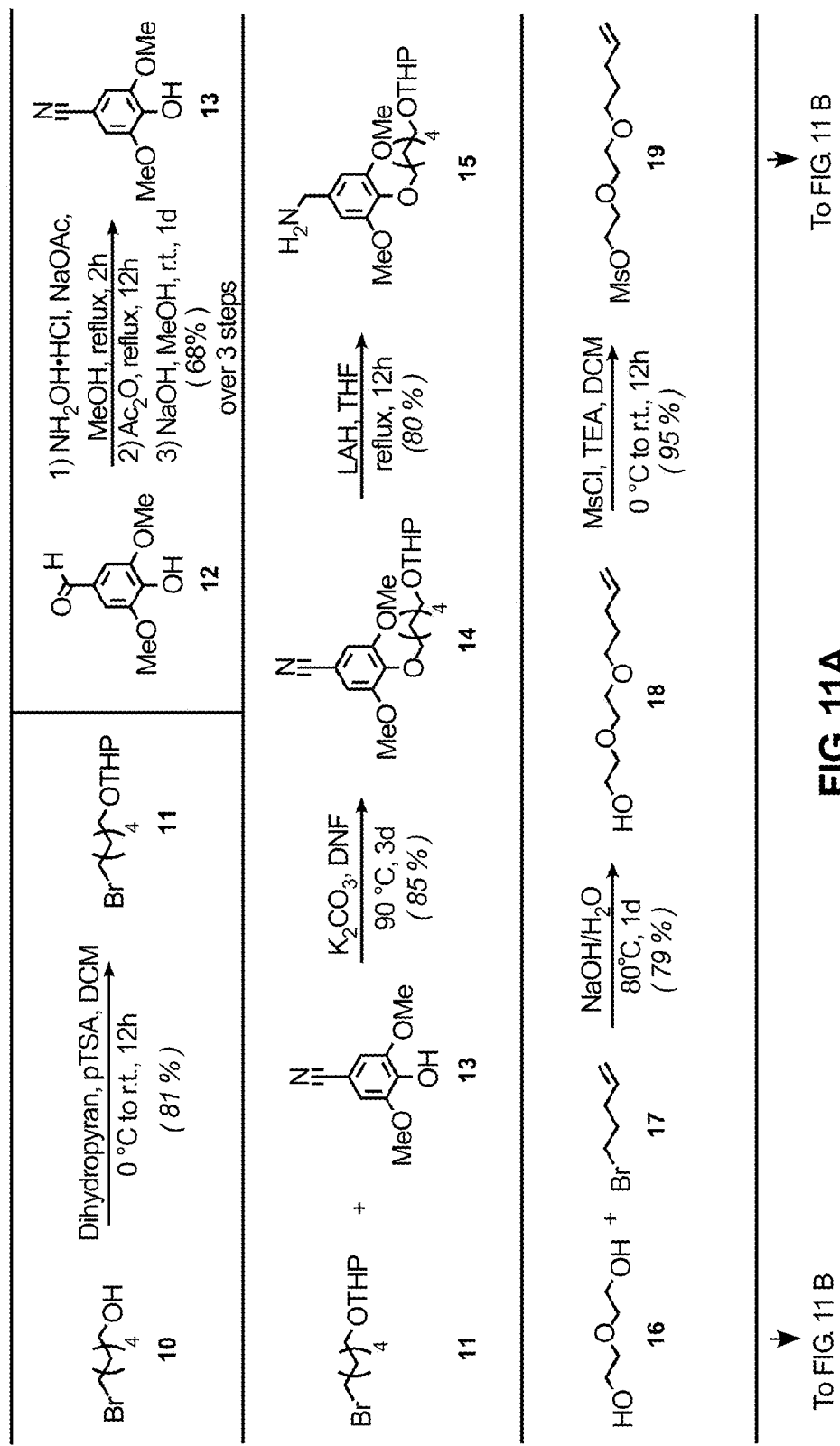
FIGS. 11A-11D show a reaction scheme related to production of the macromer depicted in FIG. 10 in a form suitable for dimerization.
Figure 11B:
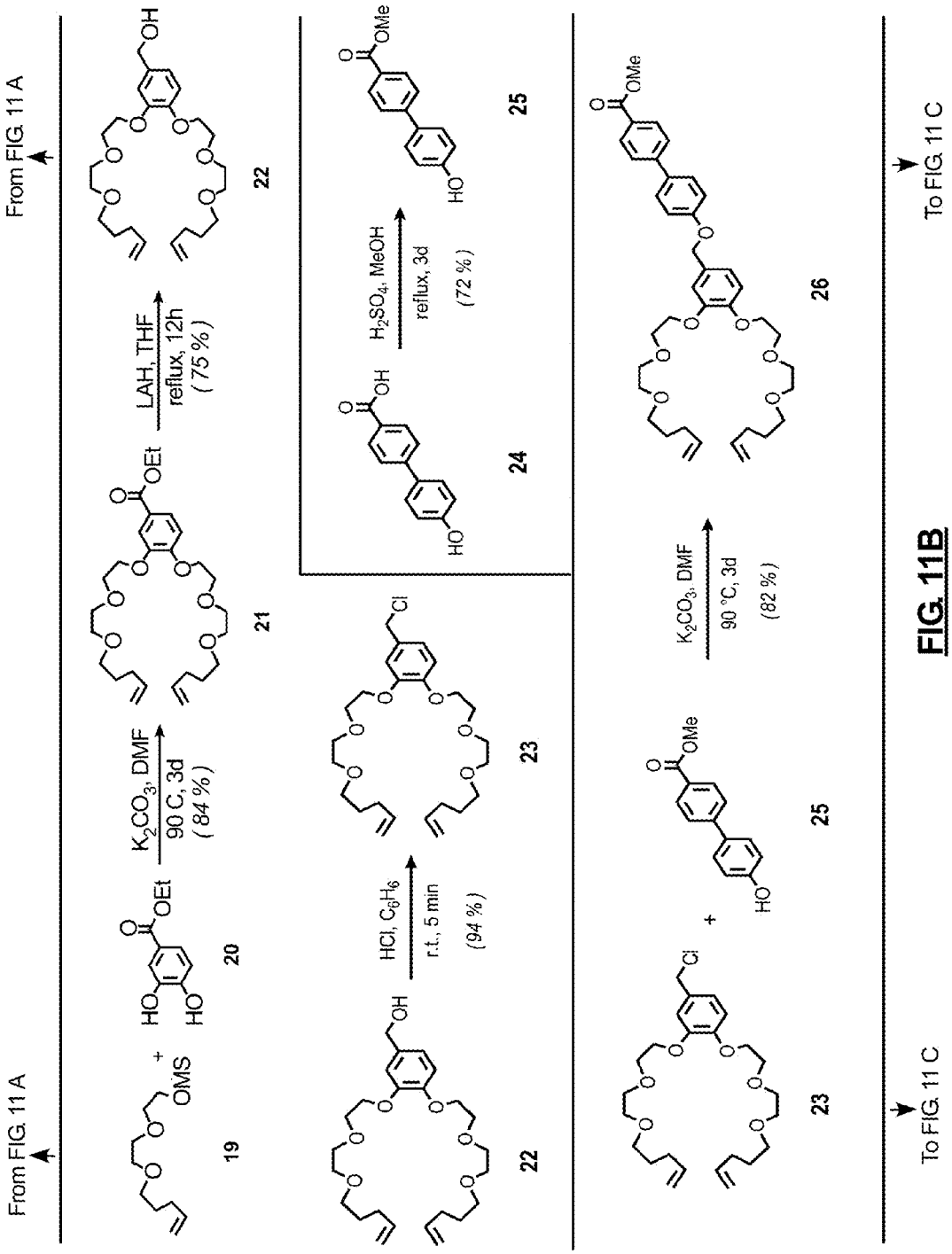
Figure 11C:
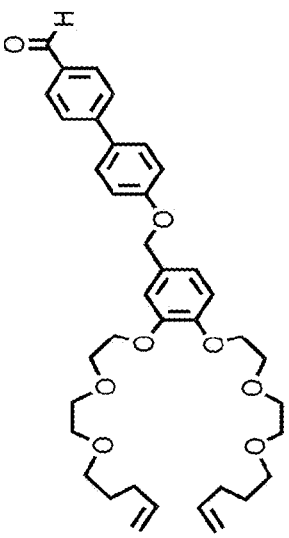
Figure 11C:
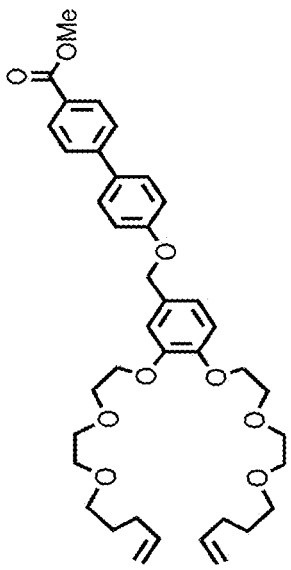
Figure 11D:
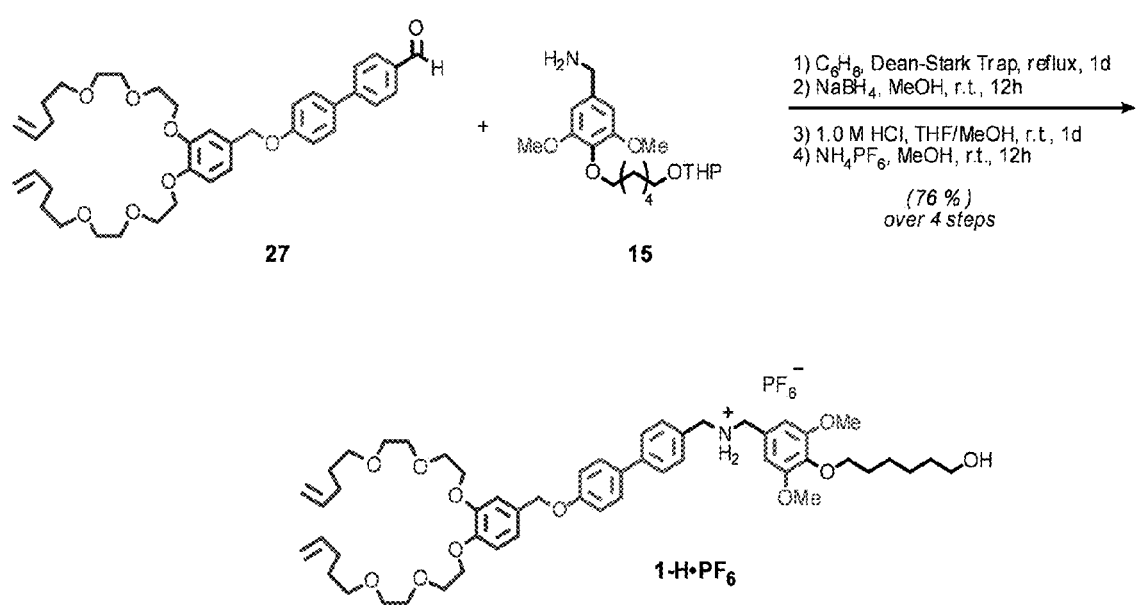

As shown in the schematic illustration of FIG. 8, polymerization can be performed by covalently linking corresponding functional groups presented on the cap portion of each macromer comprised in the DCD to be polymerized in a step growth condensation polymerization reaction.

For example, in embodiments where each macromer of the DCD has formula (I) and R10 is an amine (—NH2), the polymer can be synthesized by addition of an appropriate amide bond-forming agent (such as a diacidchloride or other appropriate species as determined by a skilled person). In embodiments, where each macromer of the DCD has formula (I) and R10 is an alcohol (—OH), the polymer can be synthesized by an appropriate esterification reaction. In other exemplary embodiments, where each macromer of the DCD has formula (I) and R10 is an alcohol, step growth polymerization reaction can be performed via functionalization of the alcohol as an azide (e.g. by treatment of the alcohol with mesyl chloride or tosyl chloride, followed by addition of sodium azide see Examples section). In some of those embodiments, using a copper catalyst (or another suitable catalyst), the resulting diazide dimer can be reacted with a dialkyne (such as 1,4-diethynylbenzene or propargyl ether) to allow the step-growth Huisgen 1,3-dipolar cycloaddition step growth polymerization product (see FIG. 8).

In some embodiments, the reagents of the step growth polymerization reaction are contacted in liquid form, and mixed in an about 1:1 molar ratio in an appropriate container without solvent and stirred vigorously. A minimum of an appropriate solvent can be added to solubilize insoluble or solid reagents. In some embodiments, solvent is kept to a minimum to drive the conversion of the step-growth polymerization to a high value (to give access to high molecular weight polymer). An "appropriate" solvent would be fulfilled by two requirements: solubilization of the components, and inability of the solvent to react with either the DCD functional group (e.g. alcohol) or other reagent used for the step growth reaction (e.g. the acyl chloride/activated acid reagent).

In some embodiments, attachment of the DCD in a polymer structure is performed through a handle portion covalently linked to the cap portions of each DCD forming macromer. The wording "handle portion" as used herein indicates a moiety presenting functional groups capable to covalently link corresponding functional groups on the cap portions of the DCDs to be polymerized. In some embodiments, the handle portion is a compound of formula (XXI)

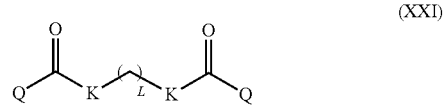

(XXI)

wherein
Q is an alogenide (e.g. chloride) or activated carboxylic acid,
K is Oxygen, or —CH2-, and
L is a 1 to 10 carbon chain.

In some embodiments, the handle portion, such as the compound of formula (XXI) can be reacted with a DCD to be polymerized to provide a handle presenting DCD which can be then polymerized through step growth polymerization reactions herein described.

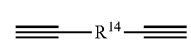

(XXII)

wherein

R$^{14}$ is alkyl, aryl, or other functionality as identifiable by a skilled person.

For example, in some embodiments, a handle portion of formula (XXII) presenting two terminal alkyne functionalities can be reacted with the cap portions of DCD comprising macromers of formula (I) displaying terminal azide functionality off of each cap to give a DCD polymer per the reaction conditions herein described in the Examples section.

Additional handle moieties and/or methods to attach the same to DCD for providing [c2] daisy chain polymer herein described are identifiable to a skilled person including for example methods described in Braunecker, Wade A.; Matyjaszewski, Krzysztof. Progress in Polymer Science 2007, 32, 93-146 herein incorporated by reference in its entirety.

In several embodiments, switching between contracted and extended state can be performed using the same methods and process herein described for DCDs.

In some embodiments, the [c2] daisy chain polymers can be used in providing materials of interest in diverse applications wherein the bioengineering: for example artificial molecular muscles.

In some embodiments, the [c2] daisy chain polymers herein described can be used to provide a material that is extendable/contractible upon introduction of a chemical trigger. In particular, in several embodiments, [c2]daisy chain polymers having the DCD units incorporated in a single strand polymer are used to provide an extendible/contractible material.

In particular, in some embodiments of materials formed by single strand [c2]daisy chain polymers, removal of coordinating interactions between the disubstituted ammonium ion and crown ether-type recognition moiety via neutralization of the ammonium ion enables the encircling crown-type arms to slide along the backbone of the DCD structure, extending the dimensions of the incorporated dimer units and, concomitantly, the dimensions of the polymer. In some embodiments of materials formed by [c2]daisy chain polymers, reprotonation of the binding site restores the crown-ammonium hydrogen bonding interactions and causes the recognitions moieties to return to their original bound conformation, resulting in contraction of the DCD units and shortening of the polymer.

In some embodiments where DCDs are incorporated in a 2-dimensional polymer sheet, the [c2] daisy chain polymers herein described can be used to provide expandable/shrinkable materials. In particular, in some embodiments of the [C2] daisy chain polymers herein described, by incorporating the dimers (in their contracted state) in a flat sheet, the reversible extension/contraction of the incorporated DCD units will cause an expansion/shrinking of the sheet in which they are incorporated.

In some embodiments, the [c2] daisy chain polymers herein described can be used to provide "self-healing" materials. In those embodiments, the [c2] daisy chain polymer is formed by DCD units that can be slided to accommodate, or make space for, a foreign object, then return to original conformation upon removal of object to "heal" the opening. In some of those embodiments, the reversible electrostatic interactions between the binding sites and recognition moieties can be disrupted (allowing extension of the dimers) without destruction of the DCD units. In some embodiments of self healing material herein described, if a material is composed of DCD units, and an object is introduced that would not be spatially accommodated, the DCD binding interactions can be disrupted and the DCD can extend. In some of those embodiments, this process provides additional space to accommodate that object. Upon removal of the object, the binding interactions of the DCD units can be restored, and the extra space created by the object be eliminated as the DCD units contracted, "healing" the material.

In some embodiments wherein extension or contraction of dimers will affect the dimensions of any 3-dimensional solid-state [c2]daisy chain polymer material in which the DCD are incorporated, the [c2] daisy chain polymers herein described can be used to provide controlled swelling of gels upon chemical trigger. In particular, in some embodiments, addition of a base would remove the binding interactions of the dimers, and the material could swell or extend beyond the dimensions of the same material with protonated/bound DCD species. The chemical trigger (e.g. addition of base) results in a dimension change of the DCD-containing gel.

In some embodiments, the [c2] daisy chain polymers herein described can be used in connection with nanodevice/nanoelectronic applications.

In some embodiments, the [c2] daisy chain polymers herein described can be used to provide chemically-triggered switches. Suitable applications for those switches comprise connecting or disconnecting a circuit depending on the bound or unbound DCD conformation. For example in some embodiments DCD units can be used to induce contact between two ends of a circuit. In some of those embodiments wherein the connection is completed when the dimer is in its contracted conformation, removal of the binding interactions of the dimer would allow extension of the dimer and loss of connectivity of the circuit. Subsequent reprotonation and contraction/binding of the DCD units can restore the connectivity of the circuit.

In some embodiments, the [c2] daisy chain polymers herein described can be used to provide molecular valves. In particular in some embodiments, valve-like behavior can be reproduced upon extension or contraction of DCD units of a [c2]daisy chain polymer material, increasing or decreasing the dimensions of an opening through which fluid or other material may flow. In some of those embodiments, the DCD can be incorporated in a cylindrical fashion at the end of a fluid-containing channel such that the contracted conformation of the dimers prevents flow of fluid out of the channel. In some embodiments, deprotonation of dimers in this arrangement results in extension of the dimers and the opening of the dimer "valve", providing a space that would enable flow of fluid out of the channel through the expanded dimers. In some embodiments, subsequent reprotonation and contraction of the dimeric units would result in closing of the dimer "valve" and prevention of fluid flowing out of the channel.

In some embodiments, the [c2] daisy chain polymers herein described can be used to provide a nanoscale delivery vehicle. In particular, in some of those embodiments a hollow structure can be provided with a shell of DCD units that under appropriate conditions would be poorly permeable prior to "switching" of the DCD units, which allows the DCD units to expand and thus increase the porous character of the shell to enable diffusion of the contents of the container into the surrounding environment. For example in embodiments wherein the [c2]daisy chain polymer is used in a cage-like structure with a shell of DCD units, the shell can be deprotonated. In some of those embodiments, a drug molecule can then be introduced and intercalated within the empty core of the DCD shell. In some embodiments, protonation of the DCD shell induces contraction of the DCD units and decrease the pore size of the membrane. In some embodiment, this process would prevent leaching of the encapsulated drug molecule into the external environment. In some embodiments, introduction of the drug-containing capsule into an appropriate biological environment would either disrupt the binding interactions (via a polar solvent that breaks up and disrupts hydrogen bonding between the ammonium and crown) or deprotonates the dimeric units and enables expansion of the capsule shell. This expansion would allow release of the encapsulated drug molecule.

In some embodiments, the [c2] daisy chain polymers herein described can be used to provide a nano"bungee" cord, a structure that has the ability to extend and contract rapidly and reversibly and thus behaves in an elastic manner. Incorporation of DCD units within a linear strand will enable highly-elastomeric behavior of linear fibers under strain by allowing the strand to extend and subsequently contract back to the original dimensions by restoring the electrostatic interactions between binding sites and recognition moieties within each incorporated DCD unit.

Additional materials and related methods and systems, comprising for example kit of parts for the synthesis of a [c2] daisy chain macromer, [c2] daisy chain dimer, [c2] daisy chain polymer or related materials herein described, and/or for the operation (e.g. switching from a contracted state to/from an extended state) of a [c2] daisy chain dimer, [c2] daisy chain polymer or related material herein described, comprising suitable reagents, vehicles or compositions, are identifiable by a skilled person upon reading of the present disclosure.

In particular, further details concerning the identification of the suitable vehicle comprising macromers, dimmers or polymers herein described, and generally manufacturing and packaging of the compositions and/or the kit, can be identified by the person skilled in the art upon reading of the present disclosure.

EXAMPLES

The macromers, dimers, polymers, and related compositions, methods system herein described are further illustrated in the following examples, which are provided by way of illustration and are not intended to be limiting.

In particular, the following examples illustrate exemplary synthesis and uses of macromer 1-H·PF$_6$ and related dimers and polymers performed according to the reaction scheme summarized in FIGS. 11A-11D, FIG. 12, and FIG. 16. A person skilled in the art will appreciate the applicability of the features described in detail for macromer 1-H·PF$_6$ for additional macromers having same or different cap, binding site, backbone and/or recognition moiety according to the present disclosure, and to related polymers.

The following experimental procedures and characterization data ($^1$H and $^{13}$C and 2D NMR, IR, HRMS, GPC) were used for all compounds and their precursors exemplified herein.

General Information. NMR spectra were obtained on either a Mercury 300 MHz spectrometer, an INOVA 500 MHz spectrometer equipped with an AutoX broadband probe with z-gradients, or an INOVA 600 MHz spectrometer equipped with an inverse HCN triple resonance probe with x,y,and z-gradients. All spectrometers were running Varian VNMRJ software. Chemical shifts for both $^1$H and $^{13}$C spectra are reported in per million (ppm) relative to Si(CH3)4 (δ=0) and referenced internally to the proteo solvent resonance. Multiplicities are abbreviated as follows: singlet (s), doublet (d), triplet (t), quartet (q), quintet (qt), septuptlet (sp), multiplet (m), and broad (br). MestReNova NMR 5.3.2 software was used to analyze all NMR spectra. Molecular mass calculations were performed with ChemBioDraw Ultra 11.0.1 (Cambridge Scientific). Mass spectrometry measurements (FAB, EI, and MALDI) were performed by the California Institute of Technology Mass Spectrometry Facility. Analytical thin-layer chromatography (TLC) was performed using silica gel 60 F254 precoated plates (0.25 mm thickness) with a fluorescent indicator. Visualization was performed using UV and iodine stain. Flash column chromatography was performed using silica gel 60 (230-400 mesh) from EM Science. Gel permeation chromatography (GPC) was carried out in 0.2 M LiBr in DMF on two I-series Mixed Bed Low MW Visco-Gel columns (Viscotek) connected in series with a DAWN EOS multiangle laser light scattering (MALLS) detector and an Optilab DSP differential refractometer (both from Wyatt Technology). No calibration standards were used, and do/dc values were obtained for each injection assuming 100% mass elution from the columns.

Materials and Methods. Anhydrous N,N-dimethylformamide (DMF) was obtained from Acros (99.8% pure, Acroseal). Dry tetrahydrofuran (THF), toluene, and dichloromethane (DCM) were purified by passage through solvent purification columns. [1] All water was deionized. 6-Bromo-1-hexanol (10, 97%), syringaldehyde (12, 98%), 5-bromo-1-pentene (17, 95%), protocatechuic acid ethyl ester (20, 97%) 4'-Hydroxy-4-biphenylcarboxylic acid (24, 99%), and 1,4-diethynylbenzene (96%) were purchased from Aldrich and used as received. Anhydrous potassium carbonate (J. T. Baker, 99.6%) was used as received. Grubbs 2nd Generation catalyst (H2IMes)(PCy$_3$)(Cl)$_2$Ru=CHPh (2) was obtained as a generous gift from Materia, Inc. All other compounds were purchased from Acros or Aldrich and used as received.

General Freeze-Pump-Thaw Procedure. A flask charged with reagents and solvent was frozen with liquid nitrogen. After the solution had frozen, the headspace of the flask was evacuated under vacuum. The flask was sealed and allowed to thaw to room temperature. The headspace of the flask was then backfilled with argon. The flask was sealed and the reaction mixture frozen again with liquid nitrogen. This process was repeated twice. On the third cycle, the solution was frozen and the headspace evacuated and backfilled with argon. Catalyst was quickly added to the top of the frozen solution, the headspace was again evacuated, and the solution allowed to warm to room temperature. The solution was backfilled with argon, refrozen, and subjected to another cycle for a total of four freeze-pump-thaw cycles.

General Phenol Alkylation Procedure. To a cooled, flame-dried, 2-neck round bottom flask, equipped with a stir bar and fitted with a septum, water jacketed reflux condenser, and vacuum adapter was added, under argon, 3 equivalents (relative to each mole of phenol) of anhydrous potassium carbonate, anhydrous DMF (to make a ~0.1 M solution), and phenol at room temperature. To this stirring mixture was added the alkylating agent dissolved in a minimal amount of DMF. The reaction was heated to 90° C. in an oil bath for 2 to 3 days, and, upon completion, was stopped by cooling to room temperature. The reaction mixture was poured into a separatory funnel, and partitioned between water (5× original volume of DMF) and ethyl acetate (1× original volume of DMF). The aqueous layer was extracted three times with fresh portions of ethyl acetate (1× original volume of DMF), and the combined organic layers were washed three times with fresh portions of water and brine (1× original volume of DMF). The washed organic layer was dried over anhydrous magnesium sulfate (MgSO$_4$), filtered through filter paper, and evaporated to dryness under reduced pressure to give the alkylation product. Purification was achieved by silica gel flash chromatography using various eluents.

General Lithium Aluminum Hydride Reduction Procedure. To a cooled, flame-dried 2-neck flask, equipped with a stir bar and fitted with a septum, water jacketed reflux condenser, and vacuum adapter was added, under argon and at 0° C., 3 equivalents of lithium aluminum hydride (LAH) powder (95+%), dry THF, and, slowly, 1 equivalent of ester, acid, aldehyde, or nitrile dissolved in a minimal amount of dry THF. The reaction was heated to 87° C. overnight in an oil bath. To quench the reaction mixture, the oil bath was removed and the reaction cooled to 0° C. Water (1 ml per gram of LAH) was added very slowly to the stirring mixture, followed by very slow addition of a 15% sodium hydroxide solution (1 ml per gram of LAH). Water (3 ml per gram of LAH) was added very rapidly, and the resulting slurry was allowed to stir for 4 hours at room temperature. After this time, a large excess of celite and anhydrous $MgSO_4$ was added, and the mixture allowed to stir for an additional hour. The reaction was filtered, and the solvent removed by rotary evaporation. The product was redissolved in organic solvent (0.5× original volume of THF), and partitioned with water (1× original volume of THF) in a separatory funnel. The water layer was extracted three times with fresh solvent (0.25× original volume of THF), and the combined organic layer was washed with two fresh portions of water (0.5× original volume of THF), dried over anhydrous $MgSO_4$, filtered, and evaporated to dryness under reduced pressure to give the reduced product. The products were used with no further purification, or purified via specified protocols.

Example 1

Preparation of a Precursor of an Ester Type Ethyl Crown Recognition Fragment 2-(2-(Pent-4-enyloxy)ethoxy)ethyl methanesulfonate 19, an exemplary precursor of the ester type ethyl crown recognition fragment described in Example 2 was prepared according to the procedures exemplified below.

2-(6-Bromohexyloxy)tetrahydro-2H-pyran 11, was first synthesized according to the following reaction scheme.

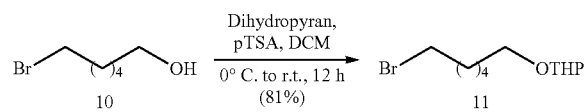

In particular, a cooled, flame-dried round bottom flask equipped with a stir bar and septum was charged, under argon and at 0° C., with 6-bromo-1-hexanol 10 (7.6551 g, 42.28 mmol, 1 eq), dry DCM (10 ml), dihydropyran (4.25 ml, 46.51 mmol, 1.1 eq), and p-toluenesulfonic acid (0.4030 g, 2.12 mmol, 5 mol %). The reaction was allowed to stir at room temperature overnight, and was quenched by diluting with water (50 ml) and DCM (50 ml) in a separatory funnel. The organic layer was washed three times with brine (3×50 ml), dried ($MgSO_4$), filtered, and evaporated to dryness under reduced pressure. Flash chromatography ($SiO_2$: 15:1 hexanes to ethyl acetate) gave 11 (9.0902 g, 81% yield) as a clear oil. $^1$H NMR (500 MHz, $CDCl_3$): δ 84.56 (t, J=2.75 Hz, 1H), 3.85 (m, 1H), 3.72 (m, 1H), 3.51 (m, 1H), 3.40 (m, 3H), 1.95-1.36 (br m, 14H). $^{13}$C NMR (126 MHz, $CDCl_3$): δ 99.05, 67.56, 62.54, 34.02, 32.92, 30.94, 29.73, 28.18, 25.67, 25.65, 19.87. HRMS-FAB (m/z): [M+H] calcd for $C_{11}H_{22}O_2Br$, 265.0803; found 265.0804.

Nitrile cap fragment 13, was then prepared according to the following reaction scheme

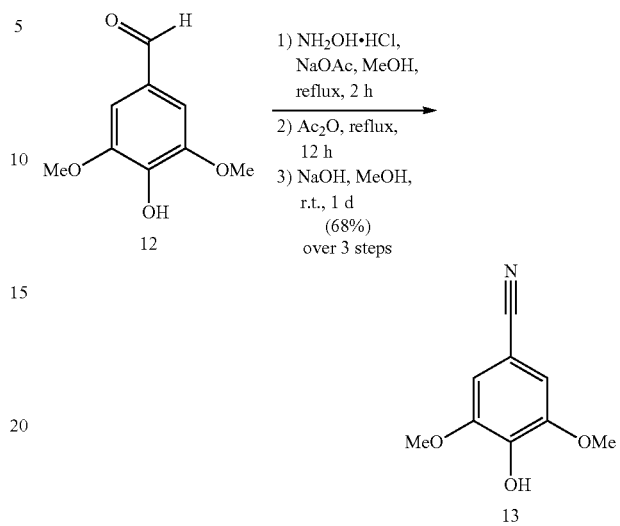

In particular, to a flask fitted with a reflux condenser was added syringaldehyde 12 (5.0000 g, 27.44 mmol, 1 eq) and methanol. Sodium acetate (3.3999 g, 42.43 mmol, 1.51 eq) was added to the stirring solution, followed by hydroxylamine hydrochloride (2.8610 g, 41.16 mmol, 1.5 eq). The solution was heated to reflux for 2 h, then cooled to room temperature. The methanol was removed under reduced pressure, and the residue redissolved in ethyl acetate (100 ml) and added to a separatory funnel. Brine (50 ml) and an aqueous solution of citric acid (23.1 g, 109.8 mmol, 4 eq in 220 ml water, 0.5 M) were added, and the aqueous layer was extracted twice more with fresh ethyl acetate (2×50 ml). The combined organic layer was washed with brine (2×50 ml), dried over magnesium sulfate, filtered, and evaporated to dryness under reduced pressure to give a yellow solid (5.1273 g, 95%). The oxime was dissolved in acetic anhydride (25 ml, 250 mmol, 10 eq) and heated to reflux for 1d. The acetic anhydride was removed under high vacuum, and the resulting black residue dissolved in ethyl acetate and mixed in a separatory funnel with saturated sodium bicarbonate and water. The aqueous layer was extracted with fresh ethyl acetate (2×100 ml), and the combined organic layers were dried over magnesium sulfate, filtered, and evaporated to dryness, giving a brown oil. Methanol (80 ml, 0.4 M) was added to the oil, followed by a 50 weight percent solution of sodium hydroxide (10.33 g, 250 mmol). After stirring overnight, the methanol was removed by rotary evaporation and the aqueous layer acidified with 2 M hydrochloric acid. Ethyl acetate was mixed with the aqueous layer, and the solution extracted with fresh ethyl acetate (3×50 ml). The combined organic layers were washed with water (2×100 ml), dried over magnesium sulfate, and evaporated under reduced pressure to give a thick oil that solidified upon standing. Purification was achieved by flash chromatography ($SiO_2$: gradient from 6:1 to 4:1 to 2:1 hexanes to acetone) to give 13 as an off-white crystalline solid (3.1574 g, 68%). $^1$H NMR (600 MHz, Acetone-$d_6$): δ 8.20 (br s, 1H), 6.97 (s, 2H), 3.85 (s, 6H). $^{13}$C NMR (75 MHz, Acetone-$d_6$): δ 148.95, 141.51, 120.15, 110.41, 102.06, 56.91. HRMS-EI (m/z): [M+H] calcd for $C_9H_{10}NO_3$, 180.0661; found 180.0643.

The alkylated nitrile cap fragment 14 was then prepared according to the following reaction scheme.

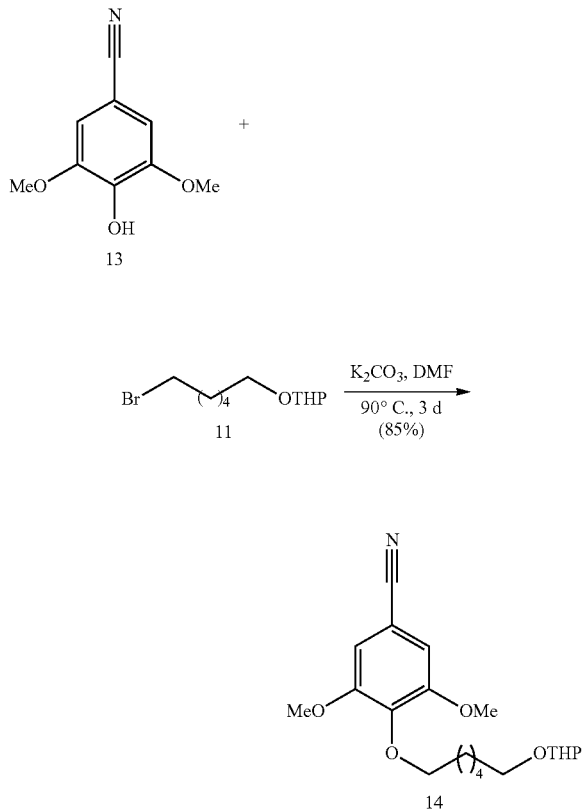

In particular, standard alkylation conditions were used with 13 (2.8437 g, 15.87 mmol, 1 eq), 11 (4.2089 g, 15.87 mmol, 1 eq), K$_2$CO$_3$ (6.5802 g, 47.61 mmol, 3 eq), and dry DMF (150 ml, 0.1M). The reaction was heated for 3 days, followed by extraction with ethyl acetate. Flash chromatography (SiO$_2$: 4:1 hexanes to acetone) gave 14 (4.9 g, 85% yield) as a clear oil. $^1$H NMR (500 MHz, CDCl$_3$): δ 6.78 (s, 2H), 4.49 (t, J=2.75 Hz, 1H), 4.95 (t, J=6.74 Hz, 2H), 3.80 (m, 1H), 3.78 (s, 6H), 3.65 (m, 1H), 3.41 (m, 1H), 3.31 (m, 1H), 1.91-1.32 (m, 14H). $^{13}$C NMR (126 MHz, CDCl$_3$): δ 153.83, 141.77, 119.06, 109.50, 106.45, 98.90, 73.65, 67.55, 62.39, 56.39, 30.82, 30.03, 29.75, 26.02, 25.64, 25.53, 19.76. HRMS-EI (m/z): [M+H] calcd for C$_{20}$H$_{29}$NO$_5$, 363.2046; found 363.2031.

The alkylated nitrile cap fragment 15 was then prepared according to the following reaction scheme.

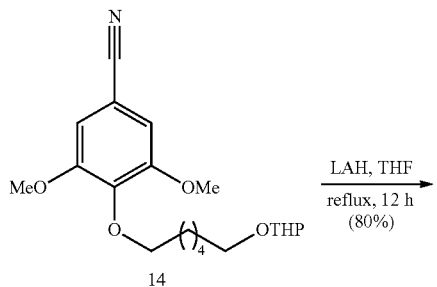

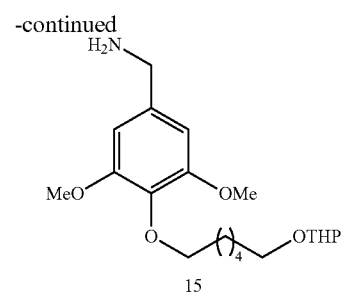

In particular, standard LAH reduction conditions were used with 14 (4.9 g, 13.48 mmol, 1 eq), LAH (1.5349 g, 40.44 mmol, 3 eq), and dry THF (200 ml, 0.07 M). After heating overnight, the reaction was quenched, filtered, and the solvent removed under reduced pressure to give 15 (3.9635 g, 80% yield) as a clear oil. $^1$H NMR (500 MHz, CDCl$_3$): δ 6.52 (s, 2H), 4.55 (t, J=2.75 Hz, 1H), 3.92 (m, 2H), 3.84 (m, 1H), 3.82 (s, 6H), 3.80 (s, 2H), 3.72 (m, 1H), 3.47 (m, 1H), 3.37 (m, 1H), 1.86-1.26 (m, 14H). $^{13}$C NMR (126 MHz, CDCl$_3$): δ 153.58, 138.75, 136.09, 104.11, 98.89, 73.39, 67.66, 62.39, 56.15, 46.79, 30.84, 30.22, 30.08, 29.81, 26.13, 25.80, 25.56, 19.76. HRMS-FAB (m/z): [M+H] calcd for C$_{20}$H$_{34}$O$_5$N, 368.2437; found 368.2450.

2-(2-(Pent-4-enyloxy)ethoxy)ethanol 18 was then prepared according to the following reaction scheme.

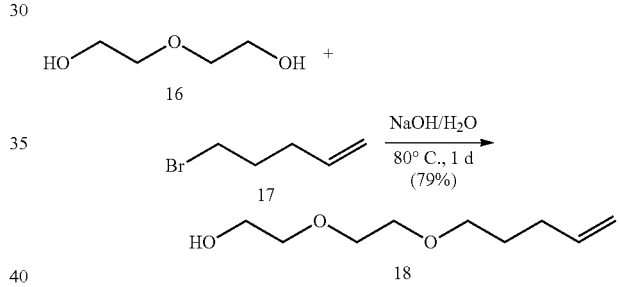

In particular, a flask equipped with a stir bar was charged with diethylene glycol 16 (637 ml, 6.71 moles, 20 eq) and 5-bromo-1-pentene 17 (50 g, 0.37 moles, 1 eq). A solution of sodium hydroxide and water (67.1 g NaOH, 1.68 moles, 5 eq; 67 ml of H$_2$O) was added slowly over a period of one hour via an addition funnel, resulting in turbidity of the reaction mixture. The reaction was heated to 80° C. for one day, and after cooling to room temperature, the mixture was poured into a separatory funnel, diluted with methylene chloride (500 ml), water (500 ml), and brine (500 ml). The aqueous layer was extracted four times with fresh methylene chloride (4×250 ml), and the combined organic layers were washed two times with fresh water and brine (2×500 ml), dried over magnesium sulfate, filtered, and evaporated to dryness under reduced pressure. The resulting residue was purified by flash chromatography, (SiO$_2$: gradient from 3:1 hexanes to ethyl acetate to 1:1 hexanes to ethyl acetate) to afford pure 18 (46.8 g, 80% yield) as a clear oil. $^1$H NMR (600 MHz, CDCl$_3$): δ=5.81 (m, center, 1 H), 5.05-4.94 (m, 2 H), 3.75-3.72 (m, 2 H), 3.69-3.66 (m, 2 H), 3.64-3.61 (m, 2 H), 3.61-3.58 (m, 2 H), 3.48 (t, J=6.7, 2 H), 2.42 (t, J=6.1 Hz, 1H), 2.14-2.09 (m, 2 H), 1.70 (qt, J=7.1, 2 H); $^{13}$C NMR (125 MHz, CDCl$_3$): δ=138.37, 115.02, 72.70, 70.99, 70.73, 70.43, 62.10, 30.41, 28.95. HRMS-EI (m/z): [M +H] calcd for C$_9$H$_{18}$O$_3$, 174.1256; found 174.1262.

2-(2-(Pent-4-enyloxy)ethoxy)ethyl methanesulfonate 19 was finally prepared according to the following reaction scheme.

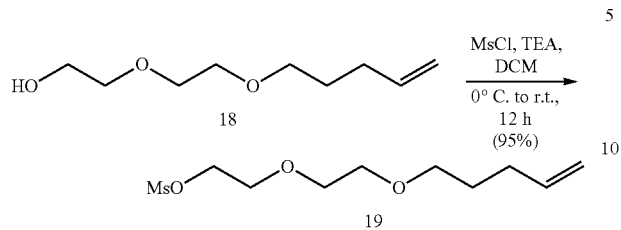

In particular, cooled, flame-dried flask equipped with a stir bar and septum was charged with 18 (46.3 g, 0.266 moles, 1 eq) and dry DCM (300 ml, 0.9 M), then cooled to 0° C. To the cooled reaction mixture was slowly added methanesulfonyl chloride (31 ml, 0.399 moles, 1.5 eq) and triethylamine (55.5 ml, 0.399 moles, 1.5 eq) alternately in several batches. The reaction was allowed to warm to room temperature and stirred overnight. Stirring was stopped and the reaction mixture poured into a separatory funnel and partitioned with water and brine (1 L). The aqueous layer was extracted three times with fresh DCM (3×300 ml), and the combined organic layers were washed three times with fresh water and brine (3×300 ml), dried over magnesium sulfate, filtered, and evaporated to dryness under reduced pressure. The resulting crude oil was purified by flash chromatography (plug of $SiO_2$: 3:2 hexanes to ethyl acetate) to give 19 (64.2 g, 96% yield) as a clear oil. $^1$H NMR (500 MHz, $CDCl_3$): δ=5.80 ppm (m, 1 H), 5.04-4.94 (br m, 2 H), 4.39-4.37 (m, 2 H), 3.78-3.75 (m, 2 H), 3.67-3.64 (m, 2 H), 3.59-3.56 (m, 2 H), 3.45 (t, J=6.6 Hz, 2 H), 3.06 (s, 1 H), 2.17-2.07 (m, 2 H), 1.67, (qt, J=7.1 Hz, 2 H); $^{13}$C NMR (126 MHz, $CDCl_3$): δ=138.34, 115.01, 70.93, 70.92, 70.25, 69.48, 69.25, 37.92, 30.40, 28.97. HRMS-EI (m/z): [M+H] calcd for $C_{10}H_{21}O_5S$, 253.1110; found 253.1119.

Example 2

Production of an Ester Type Ethyl Crown Recognition Fragment

Ester type ethyl crown recognition fragment 21 was prepared according to the following reaction scheme.

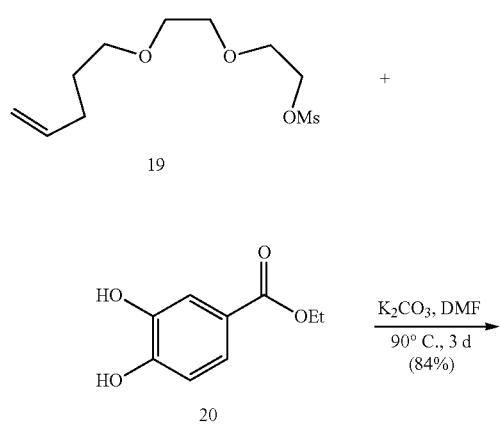

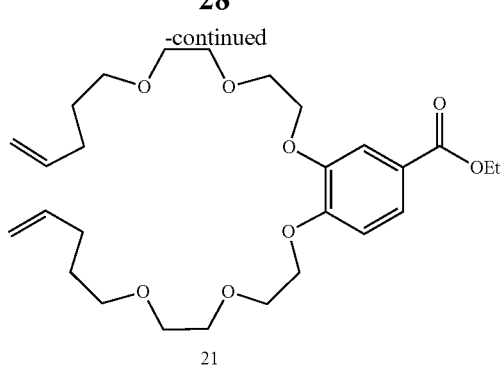

In particular, standard alkylation conditions were used with protocatechuic acid ethyl ester 20 (12.6345 g, 69.35 mmol, 1 eq), 19 (35.0000 g, 0.139 moles, 2 eq), $K_2CO_3$ (57.5217 g, 0.416 moles, 6 eq), and dry DMF (1 L, 0.07 M). After 3 days, the reaction was extracted and purified via flash chromatography ($SiO_2$: 4:1 hexanes to acetone), giving 21 (28.8 g, 84% yield) as a clear oil. $^1$H NMR (300 MHz, $CDCl_3$): δ7.60 (m, 1H), 7.53 (m, 1H), 6.86 (m, 1H), 5.75 (m, 2H), 5.05-4.84 (m, 4H), 4.28 (m, 2H), 4.16 (m, 4H), 3.84 (m, 4H), 3.68 (m, 4H), 3.54 (m, 4H), 3.41 (m, 4H), 2.13-1.98 (m, 4H), 1.62 (m, 4H), 1.31 (m, 3H). $^{13}$C NMR (75 MHz, $CDCl_3$): δ166.36, 152.90, 148.28, 138.32, 138.30, 123.98, 123.39, 115.00, 114.81, 114.79, 112.69, 71.04, 70.97, 70.82, 70.28, 70.27, 69.71, 69.61, 68.91, 68.68, 60.84, 30.31, 28.85, 14.49. HRMS-TOF MS (m/z): [M+Na] calcd for $C_{27}H_{42}O_8Na$, 517.2777; found 517.2796.

Example 3

Production of a Benzyl Alcohol Crown Type Recognition Fragment

Benzyl Alcohol Crown-Type Recognition Fragment 22 was prepared according to the following reaction scheme.

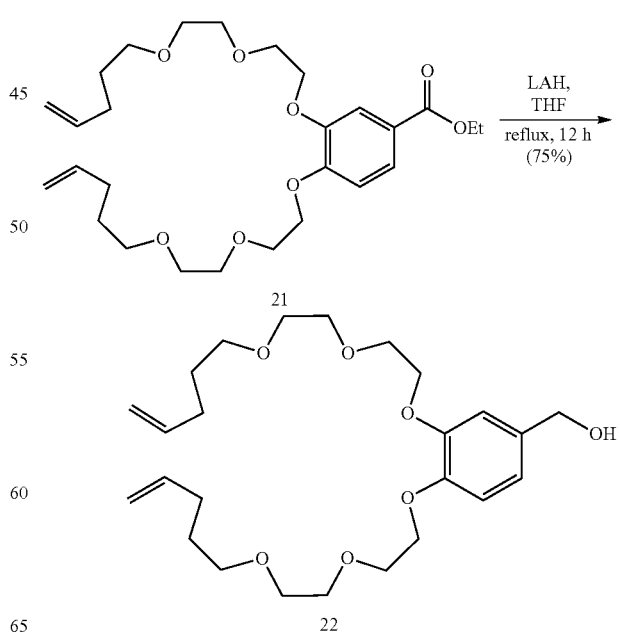

In particular, standard LAH reduction conditions were used with 21 (28.6 g, 63.24 mmol, 1 eq), LAH (7.1998 g, 0.190 moles, 3 eq), and dry THF (~630 ml, 0.1 M). The reaction was refluxed overnight, quenched, filtered, and extracted to give 22 (21.9 g, 75% yield) as a clear oil. The product was used with no further purification. $^1$H NMR (300 MHz, CDCl$_3$): δ 6.94 (s, 1H), 6.87-6.79 (m, 2H), 5.79 (m, 2H), 5.04-4.85 (m 4H), 4.55 (s, 2H), 4.14 (m, 4H), 3.83 (t, J=5.09 Hz, 4H), 3.60 (m, 4H), 3.57 (m, 4H), 3.45 (t, J=6.60 Hz, 4H), 2.14 (s, 1H), 2.08 (q, J=6.60 Hz, 4H), 1.66 (qt, J=6.60 Hz, 4H). $^{13}$C NMR (75 MHz, CDCl$_3$): δ 149.02, 148.33, 138.33, 134.74, 120.12, 114.83, 114.73, 113.75, 70.91, 70.85, 70.83, 70.25, 69.86, 69.83, 69.06, 68.84, 64.96, 30.31, 28.83. HRMS-TOF MS (m/z): [M+Na] calcd for C$_{25}$H$_{40}$O$_7$Na, 475.2672; found 475.2649.

Example 4

Production of a Benzyl Chloride Crown Type Recognition Fragment

Benzyl Chloride Crown-Type Recognition Fragment 23 was prepared according to the following reaction scheme.

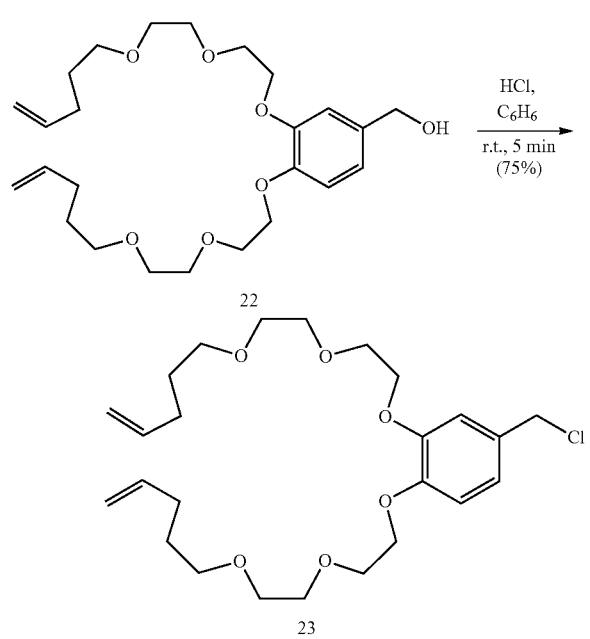

In particular, in a flask, 22 (21.9 g, 48.42 mmol, 1 eq) was dissolved in benzene (500 ml, 0.1 M), then transferred to a separatory funnel. To this mixture was added concentrated hydrochloric acid (241 ml). The reaction was shaken, with periodic venting, for 5 minutes. To quench the reaction, the solution was diluted with water (500 ml). The aqueous layer was extracted three times with fresh benzene (3×100 ml), and the combined organic layers were further washed with three portions of fresh water (3×100 ml), dried over magnesium sulfate, filtered, and evaporated to dryness under reduced pressure to provide 23 (21.4 g, 94% yield) as a pale yellow oil. The product was used without further purification. $^1$H NMR (300 MHz, CDCl$_3$): δ 6.96-6.78 (m, 3H), 5.78 (m, 2H), 5.05-4.89 (m, 4H), 4.49 (s, 2H), 4.14 (q, J=5.14 Hz, 4H), 3.83 (m, 4H), 3.69 (m, 4H), 3.57 (m, 4H), 3.44 (m, 4H), 2.09 (q, J=7.23 Hz, 4H), 1.66 (qt, J=7.08 Hz, 4H). $^{13}$C NMR (75 MHz, CDCl$_3$): δ 148.85, 148.69, 137.96, 130.40, 121.58, 114.83, 114.49, 114.00, 70.58, 70.38, 69.94, 69.45, 69.41, 68.69, 68.63, 46.18, 29.99, 28.55. HRMS-EI (m/z): [M+Na] calcd for C$_{25}$H$_{39}$O$_6$NaCl, 493.2333; found 493.2354.

Example 5

Production of a Methyl Ester Backbone Fragment

Methyl Ester backbone Fragment 25 was prepared was prepared according to the following reaction scheme.

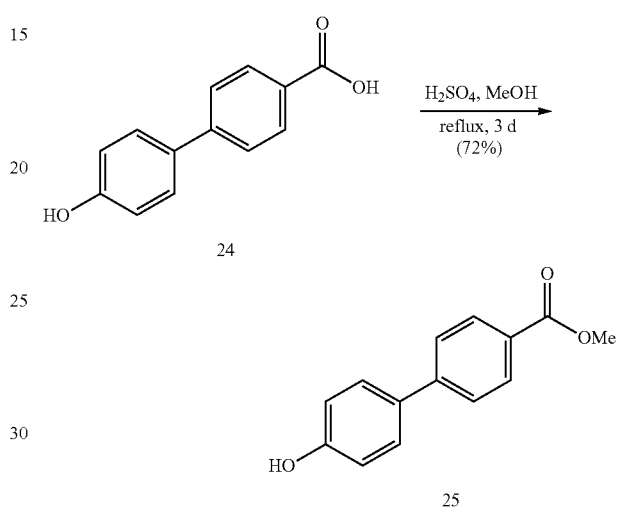

In particular, a flask equipped with a stir bar was charged with 4'-hydroxy-4-biphenylcarboxylic acid 24 (9.1003 g, 42.48 mmol, 1 eq) and methanol (40 ml, 1 M). The solution was cooled to 0° C., and concentrated sulfuric acid (6 ml, 33.2 mmol, 0.8 eq) was added dropwise. The flask was fitted with a reflux condenser, and the reaction heated to reflux for 5 hours. After cooling to 0° C. in an ice bath, a 10% sodium hydroxide solution (150 ml) was added slowly to the reaction. The reaction mixture was poured into a separatory funnel, and diluted with ethyl acetate (250 ml) and water and brine (500 ml). The aqueous layer was extracted four times with ethyl acetate (4×100 ml), and the organic layers were combined, dried over magnesium sulfate, filtered, and evaporated to dryness under reduced pressure. Recrystallization from a minimum of hot ethyl acetate afforded 25 (7.0104 g, 72%) as a white crystalline solid. $^1$H NMR (300 MHz, Acetone-d$_6$): δ 8.64 (s, 1H), 8.04 (d, J=8.53 Hz, 2H), 7.73 (d, J=8.80 Hz, 2H), 7.61 (d, J=8.80 Hz, 2H), 6.97 (d, J=8.80 Hz, 2H), 3.89 (s, 3H). $^{13}$C NMR (126 MHz, Acetone-d$_6$): δ 167.22, 158.93, 146.31, 131.81, 130.83, 129.28, 129.08, 127.10, 116.84, 52.32. HRMS-FAB (m/z): [M+H] calcd for C$_{14}$H$_{12}$O$_3$, 228.0786; found 228.0796.

Example 6

Production of a Methyl Ester Recognition Backbone Fragment

Methyl Ester recognition backbone Fragment 26 was prepared was prepared according to the following reaction scheme.

31 32

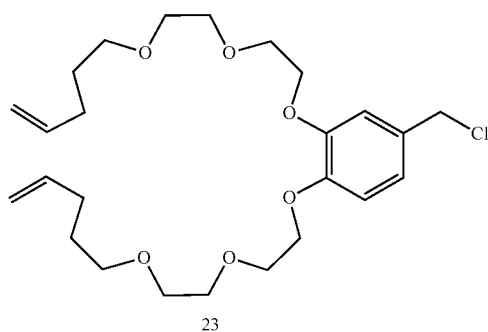 + 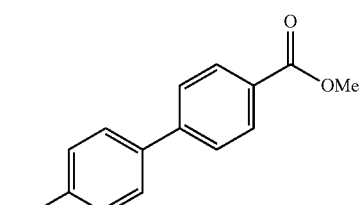

23    25

$\xrightarrow{\text{K}_2\text{CO}_3, \text{DMF}}$
90° C., 3 d
(82%)

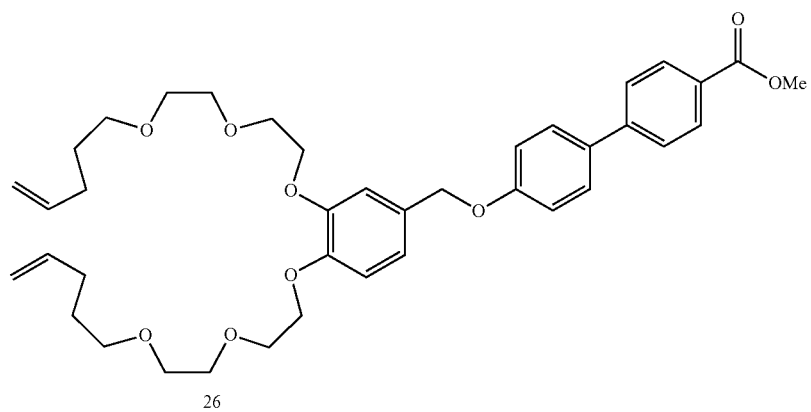

26

In particular, standard alkylation conditions were used with 23 (14.4292 g, 31.91 mmol, 1.05 eq), 25 (6.7775 g, 29.69 mmol, 1 eq), K$_2$CO$_3$ (12.3121 g, 89.07 mmol), and dry DMF (500 ml). The reaction was heated for 3 days, then extracted with ethyl acetate. The residue was purified via flash chromatography (SiO$_2$: gradient from 12:1 to 8:1 to 6:1 to 4:1 to 2:1 hexane to acetone) as eluent to give 26 (16.1 g, 82% yield) as a white crystalline solid. $^1$H NMR (300 MHz, CDCl$_3$): δ 8.05 (d, J=8.25 Hz, 2H), 7.60 (d, J=8.25 Hz, 2H), 7.55 (d, J=8.81 Hz, 2H), 7.03 (d, J=8.80 Hz, 2H), 7.01-6.85 (m, 3H), 5.78 (m, 2H), 5.05-4.88 (m, 6H), 4.16 (m 4H), 3.91 (s, 3H), 3.85 (t, J=5.09 Hz, 4H), 3.70 (m, 4H), 3.58 (m, 4H), 3.45 (m, 4H), 2.08 (m, 4H), 1.66 (m, 4H). $^{13}$C NMR (75 MHz, CDCl$_3$): δ 167.22, 159.16, 149.24, 149.00, 145.32, 138.43, 132.73, 130.26, 130.11, 128.52, 128.38, 126.63, 121.09, 115.46, 114.89, 114.77, 114.42, 71.04, 70.93, 70.36, 70.17, 69.90, 69.11, 69.07, 52.26, 30.41, 28.94. HRMS-TOF MS (m/z): [M+Na] calcd for C$_{39}$H$_{50}$O$_9$Na, 685.3353; found 685.3358.

Example 7

Production of an Aldehyde Recognition Backbone Fragment

Aldehyde Recognition-Backbone Fragment 27 was prepared according to the following reaction scheme.

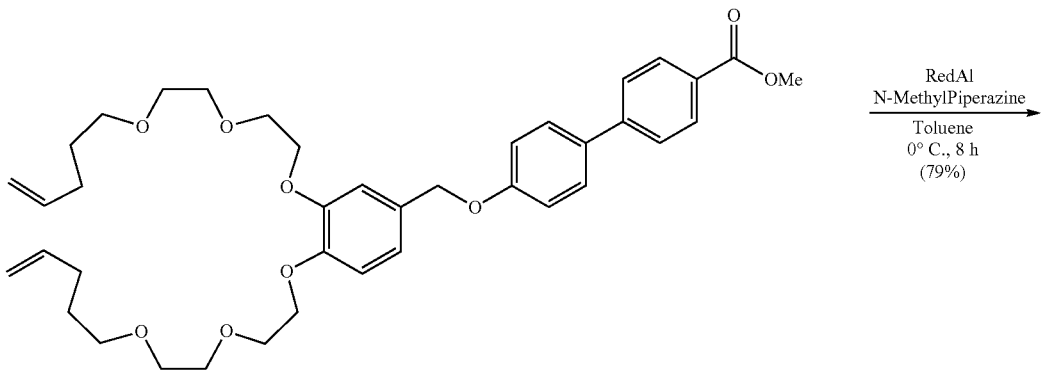

26

$\xrightarrow{\begin{array}{c}\text{RedAl}\\\text{N-MethylPiperazine}\end{array}}$
Toluene
0° C., 8 h
(79%)

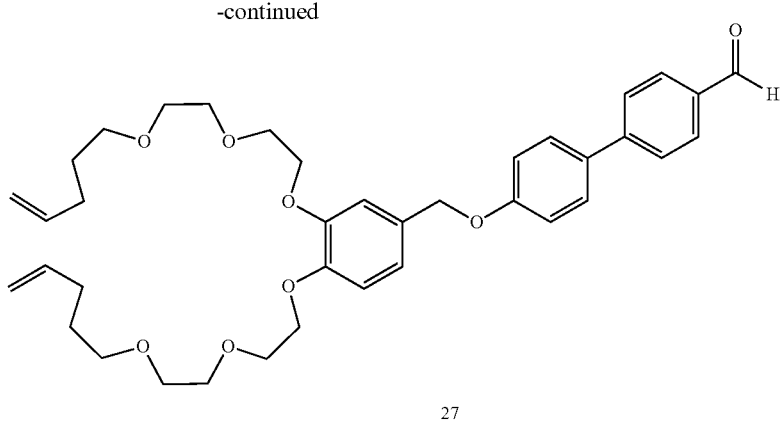

27

In particular, a cooled, flame-dried two-neck flask equipped with a stir bar, water condenser, gas port, and septum was charged, under argon at 0° C., with RedAl (9.84 ml, 32.79 mmol, 1 eq) and dry toluene (16.4 ml). To this stirring mixture was added, slowly, N-methylpiperazine (4.01 ml, 36.07 mmol, 1.2), and the reaction allowed to stir for 30 minutes at 0 ° C. A separate cooled, flame-dried two-neck flask equipped with a stir bar, water condenser, gas port, and septum was charged, under argon at 0° C., with 26 (16.1 g, 24.29 mmol) and dry toluene (25 ml). After the 30 minute incubation time, the RedAl solution was added dropwise to the stirring solution of 26 in toluene.

The reaction was allowed to stir for 8 hours at 0° C., then quenched by addition of water (20 ml). The reaction was poured into a separatory funnel, and partitioned between ethyl acetate (100 ml) and water (200 ml) and brine (200 ml). The aqueous layer was extracted two times with DCM (2×100 ml), and the ethyl acetate and DCM layers were combined and washed with fresh water and brine (2×200 ml), dried with magnesium sulfate, filtered, and the solvent removed under reduced pressure. Flash chromatography (SiO$_2$: 4:1 hexane to acetone) gave 27 (12.1 g, 79% yield) as a white crystalline solid. $^1$H NMR (300 MHz, CDCl$_3$): δ 9.93 (s, 1H), 7.82 (d, J=8.25 Hz, 2H), 7.61 (d, J=8.26 Hz, 2H), 7.49 (d, J=8.80 Hz, 2H), 6.98 (d, J=8.57 Hz, 2H), 6.95-6.79 (m, 3H), 5.73 (m, 2H), 5.05-4.88 (m, 6H), 4.12 (q, J=5.04 Hz, 4H), 3.81 (t, J=4.95 Hz, 4H), 3.67 (t, J=4.68 Hz, 4H), 3.53 (t, J=4.68 Hz, 4H), 3.40 (m, 4H), 2.12-1.98 (m, 4H), 1.62 (m, 4H). $^{13}$C NMR (75 MHz, CDCl$_3$): δ 192.04, 159.42, 149.27, 149.05, 146.87, 138.41, 134.81, 132.37, 130.46, 130.01, 128.64, 127.20, 121.09, 115.55, 114.88, 114.81, 114.47, 71.03, 70.91, 70.35, 70.17, 69.89, 69.13, 69.10, 30.39, 28.93. HRMS-FAB (m/z): [M+H−H$_2$] calcd for C$_{38}$H$_{47}$O$_8$, 631.3271; found 631.3258.

Example 8

Production of Self-Complimentary Macromer (1-HPF$_6$)

A self-complimentary macromer having formula 1-H—PF$_6$ was synthesized according to the following reaction scheme.

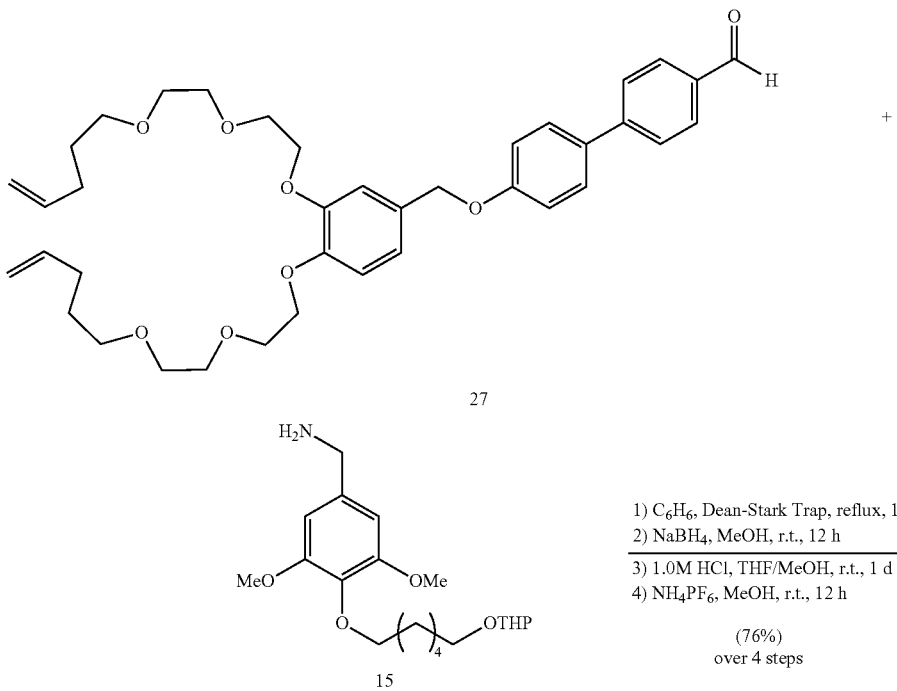

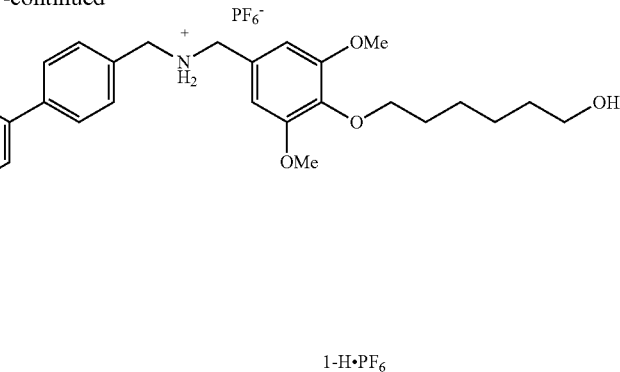

1-H·PF₆

In particular, a flask equipped with a stir bar was charged with 27 (6.8249 g, 10.79 mmol, 1 eq), 15 (3.9635 g, 10.79 mmol, 1 eq), and benzene (250 ml). The flask was fitted with a Dean-Stark trap and reflux condenser, and heated to 100° C. The trap was flushed several times over the course of the reaction. After 1 day, the reaction was cooled to room temperature and the benzene removed under reduced pressure to give imine 1a as a viscous oil (10.59 g).

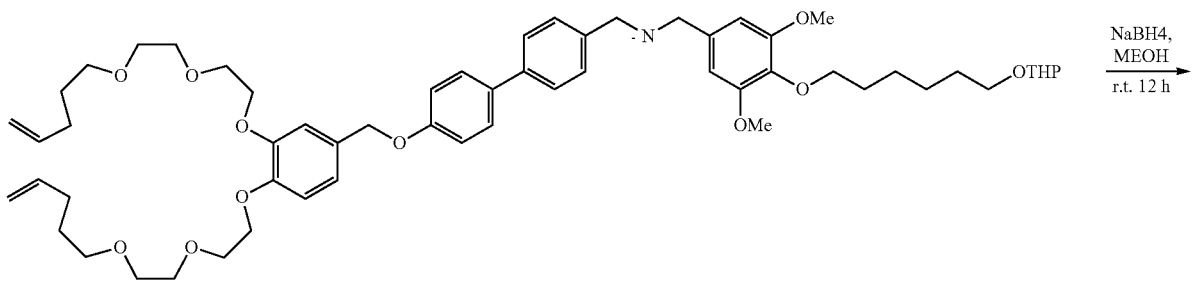

1a

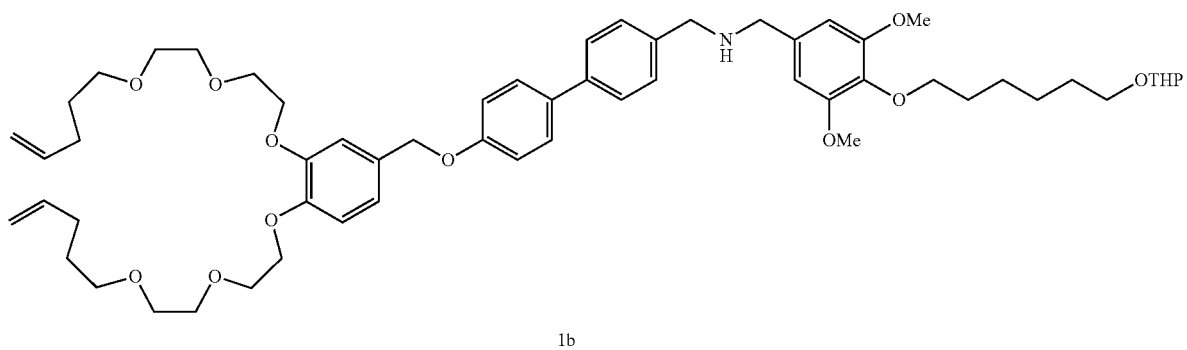

1b

Imine 1a (10.59 g) was dissolved in methanol (108 ml), and sodium borohydride (1.2241 g, 32.37 mmol) was added to the reaction. Stirring was continued at room temperature for 12 hours. The methanol was removed under reduced pressure, and the residue dissolved in DCM and transferred to a separatory funnel. Water was added, and the organic layer was rinsed three times with fresh portions of water. The organic layer was then dried over magnesium sulfate, filtered, and concentrated under reduced pressure, giving amine 1b as a thick oil (10.3 g).

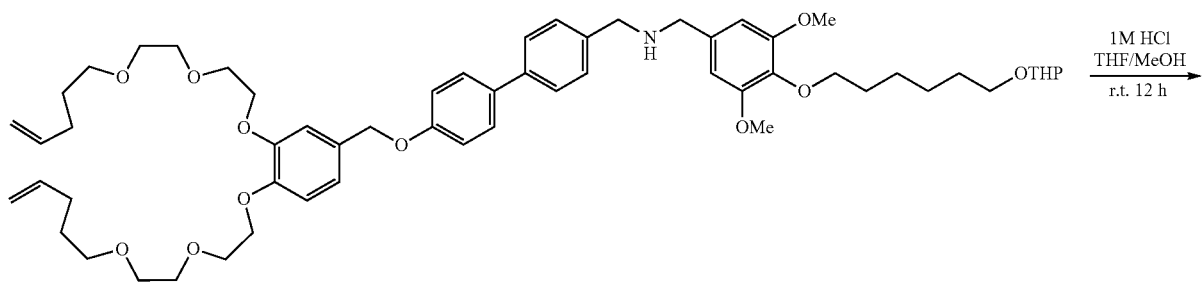

1b

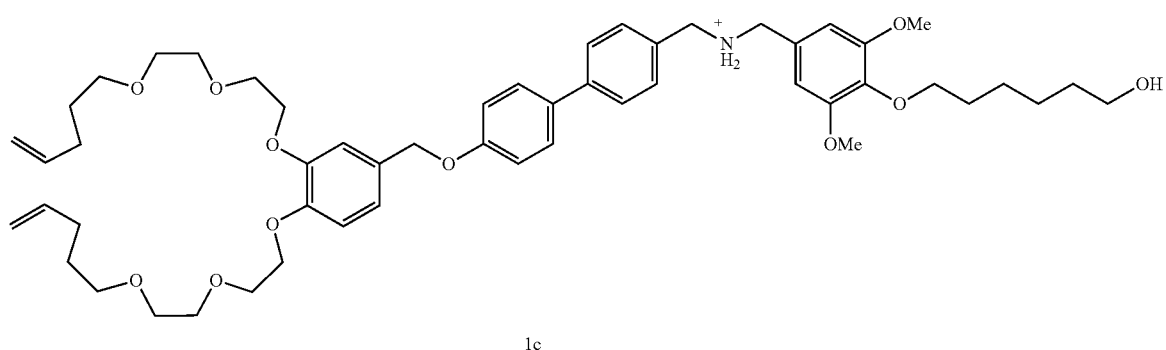

1c

The amine 1b (10.3 g) was dissolved in methanol (20 ml) and THF (100 ml), and to this mixture was added 1.0 M hydrochloric acid (155 ml, in water). This mixture was allowed to stir for one day, poured into a separatory funnel, and diluted with water and DCM. The water layer was extracted three times with fresh DCM and the combined organic layers were washed another two times with water, dried over magnesium sulfate, filtered, and evaporated to dryness under reduced pressure, giving ammonium-alcohol 1c as a waxy solid (7.9 g).

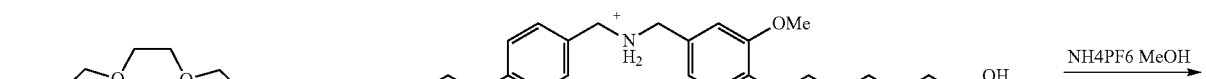

1c

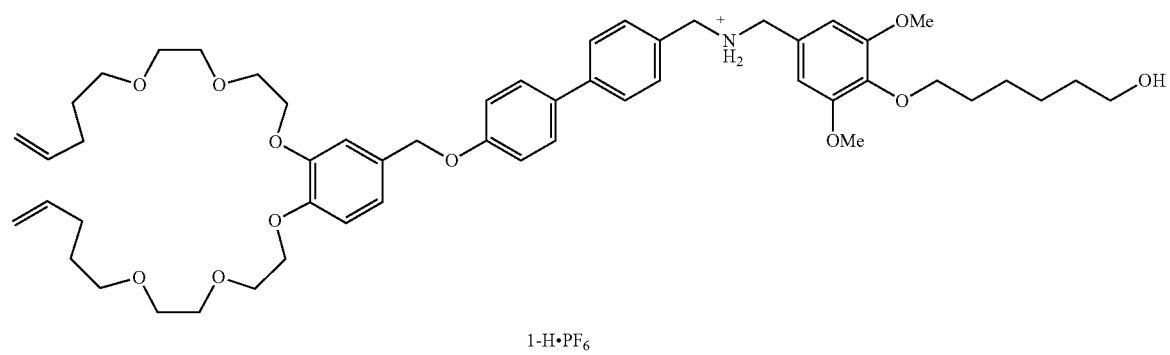

1-H·PF$_6$

The compound was redissolved in methanol (150 ml), and ammonium hexafluorophosphate (13.7485 g, 84.34 mmol) was added. The reaction mixture was allowed to stir overnight, and was halted by evaporation of methanol under reduced pressure. The residue was dissolved in DCM, poured into a separatory funnel, and diluted with water. The organic layer was washed several times with fresh water, poured through filter paper, and evaporated to dryness under reduced pressure. Flash chromatography ($SiO_2$: gradient from 2%, then 2.5%, then 10% DCM to methanol eluent) gave 1-H.$PF_6$ (8.6 g, 76% yield over 4 steps) as a pale-yellow waxy solid. $^1$H NMR (500 MHz, $CDCl_3$): δ 7.37 (m, 6H), 6.91 (m, 4H), 6.78 (s, 1H), 6.70 (s, 2H), 5.76 (m, 2H), 5.05-4.86 (m, 4H), 4.74 (s, 2H), 4.48-3.98 (m, 4H), 3.91 (t, J=6.50 Hz, 2H), 3.88-3.66 (m, 16H), 3.66-3.42 (m, 12H), 2.08 (m, 4H), 1.67 (sp, J=1.67 Hz, 4H), 1.58-1.27 (m, 8H). $^{13}$C NMR (126 MHz, $CDCl_3$): δ 158.42, 153.70, 146.50, 145.99, 141.44, 137.88, 137.72, 137.44, 131.86, 130.52, 130.03, 128.23, 127.82, 126.48, 126.35, 119.65, 115.14, 114.92, 112.30, 110.80, 105.89, 73.28, 71.18, 71.02, 70.94, 70.72, 69.85, 69.76, 69.53, 69.34, 68.53, 67.66, 62.64, 56.14, 52.41, 32.47, 30.08, 30.01, 29.86, 28.58, 28.46, 25.49, 25.38. HRMS-FAB (m/z): [M–$PF_6$] calcd for $C_{53}H_{74}NO_{11}$, 900.5262; found, 900.5245.

Example 9

Production of [c2] Daisy-Chain Dimer 3-$H_2$.$2PF_6$)

A dimer formed by monomers 1-$HPF_6$ synthesized according to the procedure exemplified in Example 1, was manufactured according to the following reaction scheme.

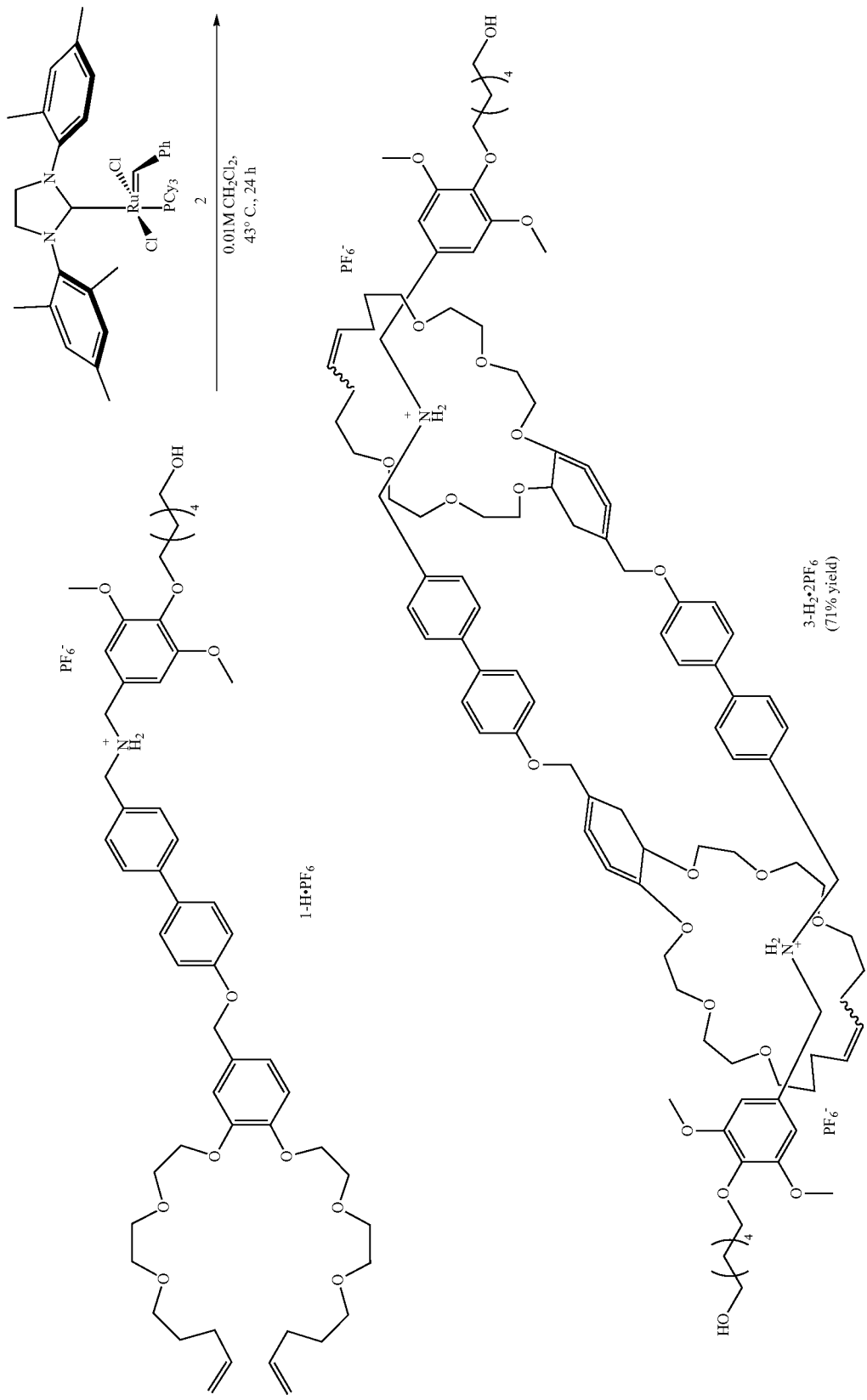

In particular, a cooled, flame-dried flask equipped with a stir bar, gas port, and septum was charged, under argon, with 1-H.PF$_6$ (10.00 g, 9.56 mmol, 1 eq) and dry DCM (960 ml, 0.01 M). This mixture was sparged with argon for 30 minutes, and catalyst (H2IMes)(PCy$_3$)(Cl)$_2$Ru=CHPh 2 (406 mg, 0.478 mmol, 5 mol %) was added. The reaction was heated to 43° C. for 24 hours and was then quenched by addition of 5 ml of ethyl vinyl ether, which was allowed to stir for 30 minutes at elevated temperature. The solvent was removed under reduced pressure to give crude 3-H$_2$.2PF$_6$ as a brown foam (9.2650 g, 91.4% recovered).

A 100.0 mg portion of the foam was purified by flash chromatography (SiO$_2$: gradient from pure DCM to 0.5% methanol in DCM to 1.0% methanol in DCM to 2% methanol in DCM to 5% methanol in DCM) to afford pure 3-H$_2$.2PF$_6$ as a white foam (77.6 mg, 71% overall isolated yield). Note: see $^1$H spectra for full assignment. $^1$H NMR (600 MHz, CD$_3$CN): δ 8.10 (br s, 2H), 7.75 (br s, 2H), 7.48-7.35 (m, 4H), 7.30-7.12 (m, 8H), 7.09 (d, J=7.6 Hz, 1H), 7.02-6.75 (m, 11H), 6.38 (m, 1H), 6.25 (m, 1H), 5.75-5.39 (m, 4H), 4.88-3.12 (br m, 72H), 2.44 (t, J=5.3 Hz, 2H), 2.41-1.99 (br m, 8H), 1.91-1.55 (m, 8H), 1.67 (qt, J=7.0 Hz, 4H), 1.54-1.43 (m, 8H), 1.41-1.32 (m, 4H). $^{13}$C NMR (126 MHz, CD$_3$CN): δ 159.96, 159.87, 155.30, 147.41, 147.26, 146.89, 146.81, 142.47, 139.18, 133.46, 133.36, 132.78, 132.69, 132.06, 132.01, 131.93, 131.59, 131.48, 131.33, 131.27, 130.90, 130.85, 130.25, 129.30, 129.27, 128.46, 127.43, 127.29, 120.35, 119.82, 116.20, 116.16, 113.52, 113.24, 111.42, 111.02, 107.71, 107.27, 74.31, 73.45, 73.25, 73.07, 72.85, 72.80, 72.51, 72.41, 72.11, 72.05, 71.41, 71.23, 71.15, 71.00, 70.96, 70.77, 70.56, 70.48, 69.72, 69.46, 69.11, 68.90, 62.97, 57.30, 57.27, 53.66, 53.43, 33.98, 31.79, 31.75, 31.25, 30.44, 30.35, 29.71, 29.67, 29.58, 29.19, 29.09, 29.07, 26.93, 26.80, 26.66, 25.95. FTIR (NaCl, cm$^{-1}$): 3594.29, 3445.56, 3143.46, 3008.55, 2936.49, 2870.07, 2625.68, 2249.01, 1949.63, 1721.96, 1607.67, 1594.00, 1514.17, 1502.65, 1463.46, 1433.21, 1391.50, 1372.07, 1354.31, 1334.36, 1291.77, 1249.20, 1195.92, 1181.75, 1162.97, 1128.93, 1100.34, 1050.97, 993.38, 973.95, 948.94, 913.43, 842.34, 780.57, 763.77, 730.64, 697.31, 673.00, 647.63, 619.96. ESI-TOF MS (m/z): [M+2H−2PF$_6$]$^{+2}$ calcd for C$_{51}$H$_{70}$NO$_{11}$, 872.9966; found 872.9941.

Example 10

Saturated [c2] Daisy-Chain Dimer (4-H$_2$.2PF$_6$)

A saturated dimer starting from dimers 3-H$_2$2PF$_6$ synthesized according to the procedure exemplified in Example 9 was manufactured according to the following reaction scheme.

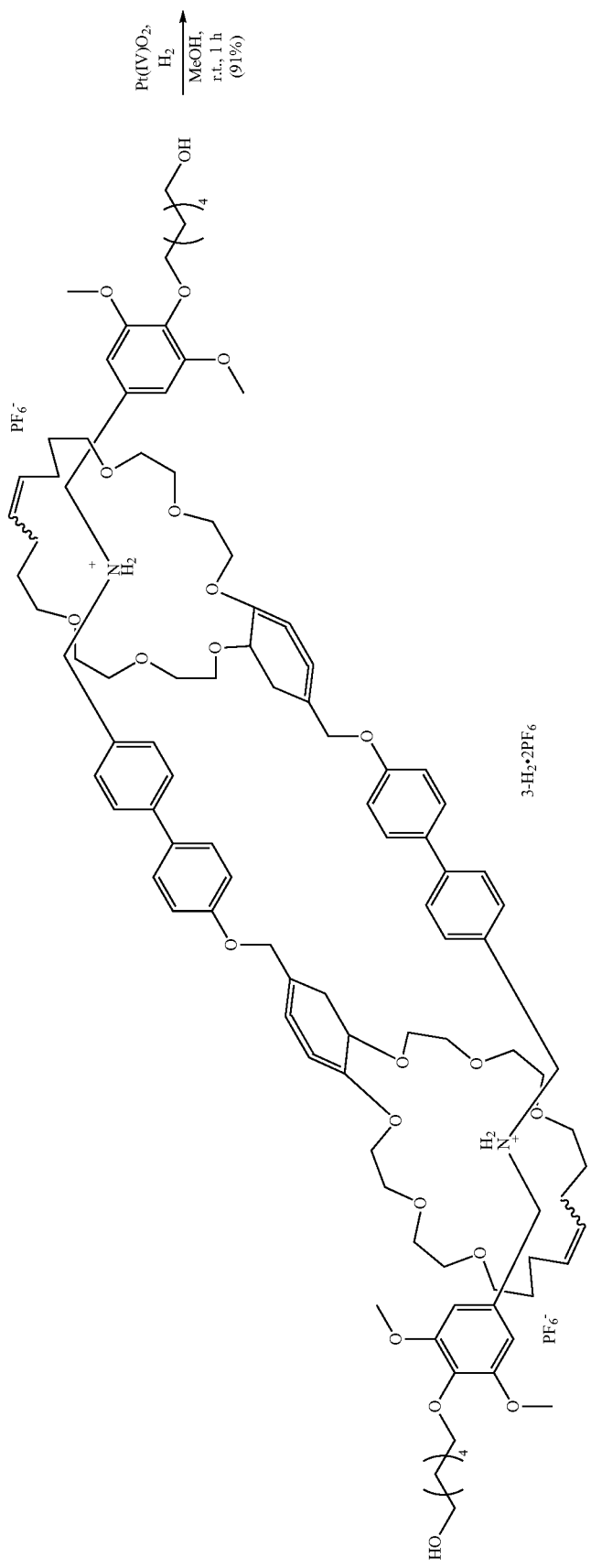

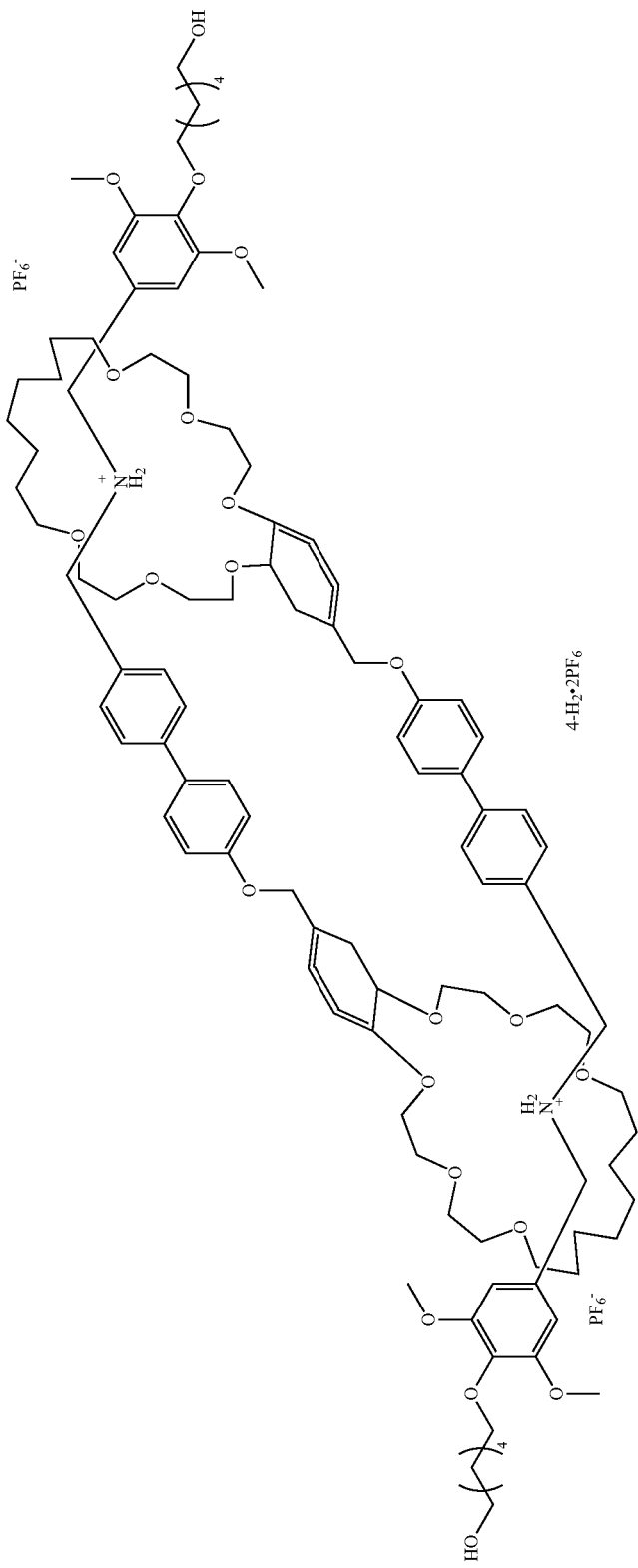

In particular, 3-H$_2$.2PF$_6$ (40.0 mg, 19.6 µmol, 1 eq) and methanol (25 ml) was added to a round bottom flask equipped with a stir bar. The dimer was dissolved in the methanol via heating, then allowed to cool to room temperature. To the solution, "Adam's Catalyst" platinum(IV) oxide (89 mg, 0.393 mmol, 20 eq) was added in one portion. The flask was sealed with a septum, and, with stirring, was vigorously sparged with hydrogen gas for 15 minutes. The catalyst changed color from brown to black-gray. After the sparging was complete, a balloon of hydrogen was placed into the septum, and a positive pressure of hydrogen was maintained throughout the course of the reaction. The reaction was stirred very vigorously for one hour then filtered through a pad of celite to give the saturated dimer 4-H$_2$.2PF$_6$ as a white solid (36.4 mg, 91% yield). (see $^1$H of 3-H$_2$.2PF$_6$ for proton letter assignments) $^1$H NMR (600 MHz, CD$_3$CN): δ 8.10 (br s, 2H), 7.75 (br s, 2H), 7.45 (d, J=8.7 Hz, 1.6H, H$_{n\,m}$), 7.41 (d, J=8.7 Hz, 2.4H, H$_{n\,r}$), 7.30-7.24 (m, 4H, H$_p$), 7.21 (d, J=8.2 Hz, 1.6H, H$_{q\,m}$), 7.17 (d, J=8.2 Hz, 2.4H, H$_{q\,r}$), 7.8 (d, J=6.7 Hz, 0.9H, H$_{l\,m}$), 6.98 (d, J=8.5 Hz, 0.9H, H$_{k\,m}$), 6.96-6.93 (s+d, 5.2H, H$_r$+H$_{l\,r}$), 6.89 (d, J=8.5 Hz, 1.3H, H$_{k\,r}$), 6.86 (d, J=8.7 Hz, 1.6H, H$_{o\,m}$), 6.82 (d, J=8.7 Hz, 2.4H, H$_{o\,r}$), 6.40 (m, 1.2 H, H$_{b\,r}$), 6.26 (m, 0.8H, H$_{b\,r}$), 4.85-4.25 (m, 12H, H$_a$+H$_j$), 4.15-3.40 (m +t$_{3.95}$+s$_{3.79}$+t$_{3.47}$, 60H, [m=H$_f$-H$_j$]+[t$_{3.95}$=H$_t$]+ [S$_{3.79}$=H$_s$]+[t$_{3.47}$=H$_y$]), 2.44 (t, J=5.3 Hz, 2H, H$_z$), 1.73-1.33 (br m, 40H, H$_u$-H$_x$+H$_c$-H$_e$). $^{13}$C NMR (126 MHz, CD$_3$CN): δ 159.96, 159.87, 155.29, 147.34, 147.24, 146.71, 146.66, 142.41, 142.28, 139.05, 133.34, 133.28, 131.98, 131.82, 131.60, 131.47, 130.23, 129.26, 128.49, 128.47, 127.44, 127.31, 120.24, 119.83, 118.69, 116.13, 113.35, 113.07, 111.31, 111.02, 107.32, 74.28, 73.44, 73.19, 73.15, 72.88, 72.83, 71.76, 71.36, 71.11, 70.12, 69.93, 69.68, 69.40, 68.95, 68.78, 62.95, 57.29, 53.80, 53.73, 33.97, 31.24, 30.88, 30.83, 30.53, 30.49, 29.10, 29.08, 28.96, 26.92, 26.79, 26.74, 26.73, 26.57, 26.55. FTIR (NaCl, cm$^{-1}$): 3593.99, 3433.21, 3137.28, 2933.11, 2860.90, 1952.15, 1593.24, 1514.07, 1501.41, 1463.66, 1435.55, 1393.10, 1372.52, 1353.85, 1334.80, 1293.11, 1248.93, 1196.12, 1181.25, 1162.76, 1128.62, 1099.00, 1048.90, 1001.31, 974.66, 906.59, 842.20, 780.29, 763.75, 735.51, 701.04, 672.30, 619.80, 588.82, 557.65, 528.46. ESI-TOF MS (m/z): [M–PF$_6$]$^{1+}$ calcd for C$_{102}$H$_{144}$N$_2$O$_{22}$F$_6$P, 1893.9853; found, 1893.9867.

Example 11

Interlocked Nature of [c2] Daisy-Chain Dimer: NMR and Crystal Diffraction

Confirmation of the interlocked nature of the product was achieved through a variety of characterization techniques. High-resolution mass spectrometry showed a dicationic species corresponding to the proposed DCD 3-H2·2PF6 of Example 9. Further evidence for the interlocked nature of the product was observed in the increased complexity of the 1H NMR spectrum, a result of the presence of both (E) and (Z) olefin isomers and a mixture of diastereomers.4a Full assignment of the 1H NMR spectrum was accomplished using a complementary set of two dimensional NMR techniques.

In addition to NMR spectroscopy and mass spectrometry characterization of 3-H2·2PF6, saturated dimer 4-H2·2PF$_6$ prepared according to the procedure of Example 10, were treated to readily produced X-ray quality crystals.

In particular, crystals suitable for x-ray diffraction were obtained for the mesoform via slow evaporation of a solution of 4-H$_2$.2PF$_6$ (10.7 mg) in 3:3:1 hexanes:ethyl acetate:acetonitrile (0.5 ml, 0.5 ml, 0.17 ml, respectively). The racemic mixture remained soluble and did not crystallize (see $^1$H NMR of each diastereomer in spectra section). The solid-state structure was deposited in the CCDC: 734570.

Crystals were mounted on a glass fiber using Paratone oil then placed on the diffractometer under a nitrogen stream at 100K. The hydroxy tail (O1-C6) is disordered and was modeled isotropically with geometry restraints. All anions and possible solvent molecules were removed from the coordinates and the program SQUEEZE (Sluis, P. v.d.; Spek, A. L. Acta Crystallogr., Sect A 1990, 46, 194-201). was used to adjust intensities so as to account for electrons in the solvent region without including them explicitly as discrete atoms. Approximately 1152 electrons (eight hexafluorophosphates) were excluded in this way and 1233 were recovered by the program. These were NOT included in the molecular weight, calculated density or F(000).

Refinement of F$^2$ was applied against ALL reflections. The weighted R-factor (wR) and goodness of fit (S) are based on F$^2$, conventional R-factors (R) are based on F, with F set to zero for negative F$^2$. The threshold expression of F$^2$>2σ(F$^2$) is used only for calculating R-factors(gt) etc. and is not relevant to the choice of reflections for refinement. R-factors based on F$^2$ are statistically about twice as large as those based on F, and R-factors based on ALL data will be even larger.

All esds (except the esd in the dihedral angle between two l.s. planes) are estimated using the full covariance matrix. The cell esds were taken into account individually in the estimation of esds in distances, angles and torsion angles; correlations between esds in cell parameters are only used when they are defined by crystal symmetry. An approximate (isotropic) treatment of cell esds is used for estimating esds involving l.s. planes.

Figure 13:
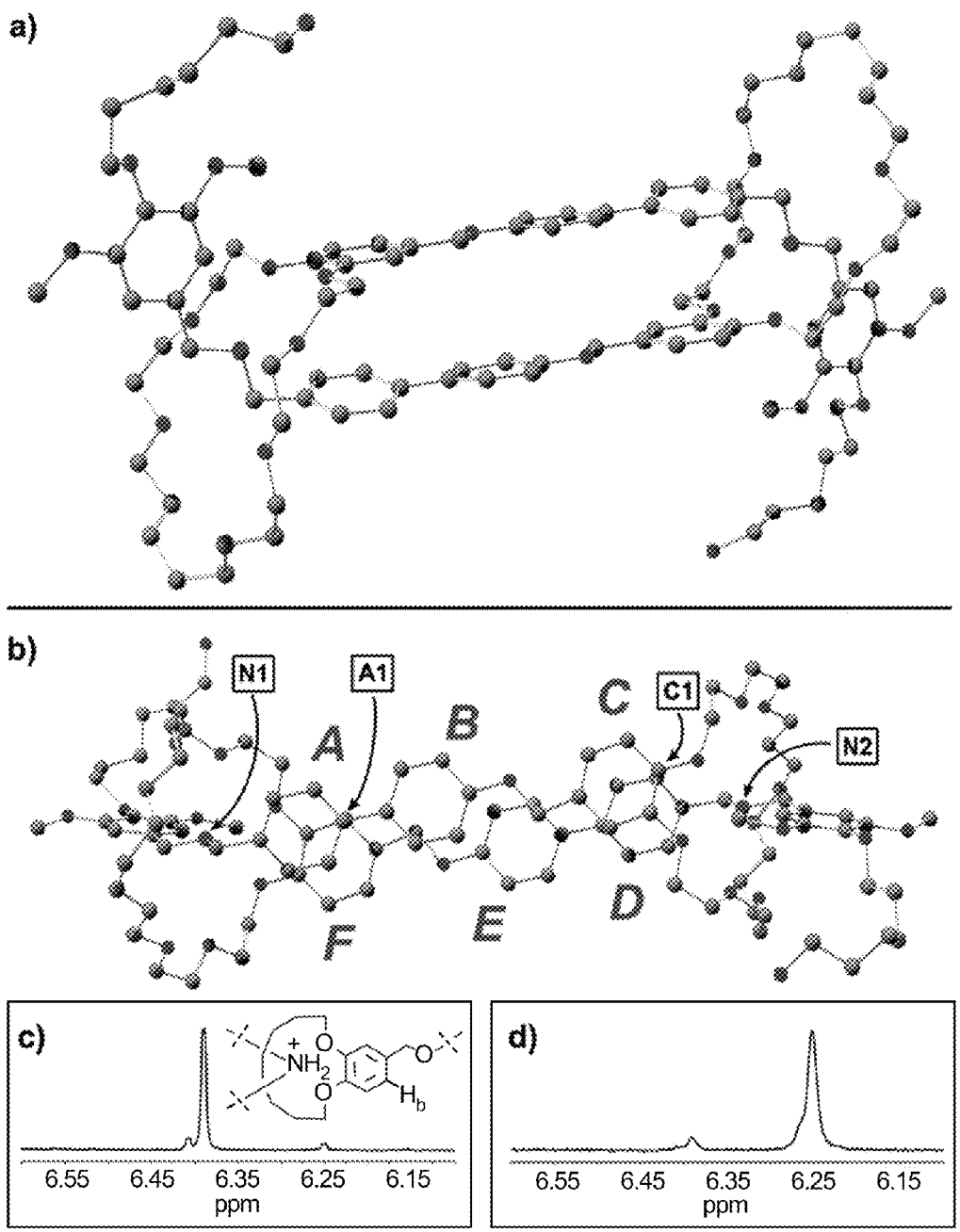
FIG. 13 shows an ORTEP representation of 4-H2·2PF6: side-on view (a) and topdown view (b), showing π-π slipped-stacking interactions between rings A and F as well as C and D (average interplanar distance: 3.4 Å). Hydrogen atoms, counterions, and solvent molecules have been omitted for clarity. Partial 1H NMR spectrum of 4-H2·2PF6 corresponding to the signal from Hb of the racemate (c) and mesoform (d).
Figure 15:
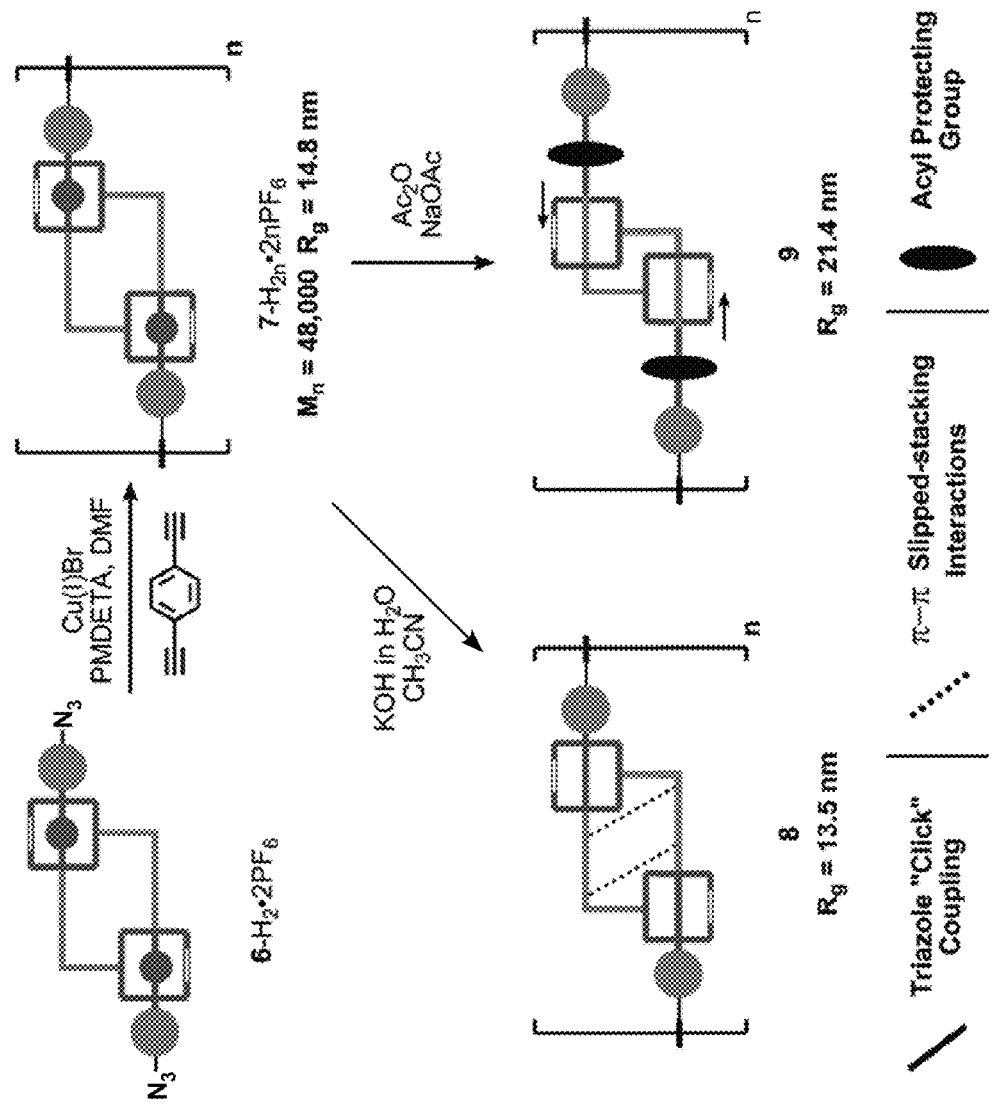
FIG. 15 shows a graphical representation depicting a synthesis of a linear "Click" Polymer 7-H2n· and activation of 2nPF6, Decoordinated Polymer 8, and Extended Acylated Polymer 9.

The solid-state structure illustrated in FIG. 13 unambiguously confirmed the interlocked nature of 4-H2·2PF6, with the crown ether-type arms encircling the ammonium of a partner macromer. In contrast to other reports of such compounds,4a,8a the mesoform of 4-H2·2PF6 was observed in the solid state structure. A possible and binding explanation of this phenomenon which is provided for guidance purpose by the Applicants is that such phenomenon is attributed to the presence of strong π-π slipped-stacking interactions17 (average "backbone"-to-"backbone" distance of 3.4 Å) between rings A and F as well as C and D (FIG. 15B), imparting enhanced stability to the mesoform of the dimer.

Due to inversion of one crown-aryl ring (either C or F) prior to interlocking, the racemic form of 4-H2·2PF6 is likely unable to simultaneously engage in extensive π-πslipped-stacking interactions and strong crown ether-ammonium hydrogen bonding interactions, resulting in limited crystallinity. Evidence for the distinct environment of crown-aryl proton Hb (Scheme 1) of each diastereomer is observed in the 1H NMR spectrum (FIG. 15C and FIG. 15D), confirming the altered alignment of the crown-aryl rings. Evidence from the crystal structure provided insight into the expected extension distance of the deprotonated forms of 3-H2·2PF6 and 4-H2·2PF6. One scenario would involve sliding of the dimer backbone through the crown-type macrocycles until ring A aligned over ring D in a conformation similar to ring C in the bound state. In this case, the measured distance between A1 to C1 (a 10.7 Å extension distance) can be related to the binding-siteto-binding-site dimer length from N1 to N2 (18.3 Å), giving an extension of 58%.

This value is very similar to the largest known extension percent of synthetic interlocked molecular actuators (66%) .18 To demonstrate utility as a molecular actuator, switching between bound and unbound conformations of 3-H2·2PF6 was easily and rapidly accomplished. Addition of a solution of potassium hydroxide in D2O to 3-H2·2PF6 in CD3CN (FIG. 14) quickly affected ammonium deprotonation to give the unbound analogue as illustrated in greater detail in the following Example 13.

Example 13

Deprotonated [c2] Daisy-Chain Dimer

A deprotonated [c2] daisy-chain dimer starting from dimers 3-$H_2$.$2PF_6$ synthesized according to the procedure exemplified in Example 9 was manufactured according to the following reaction scheme.

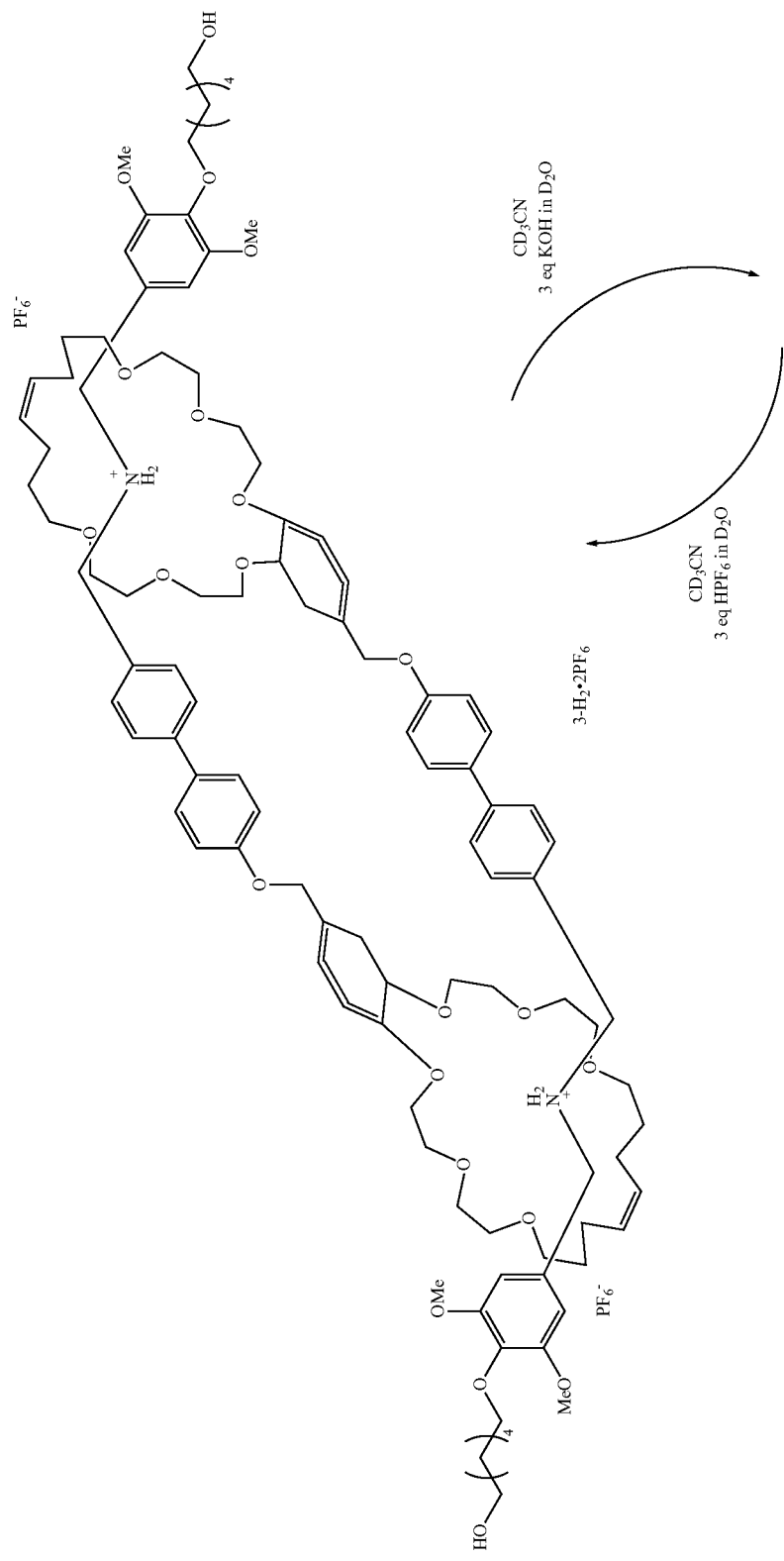

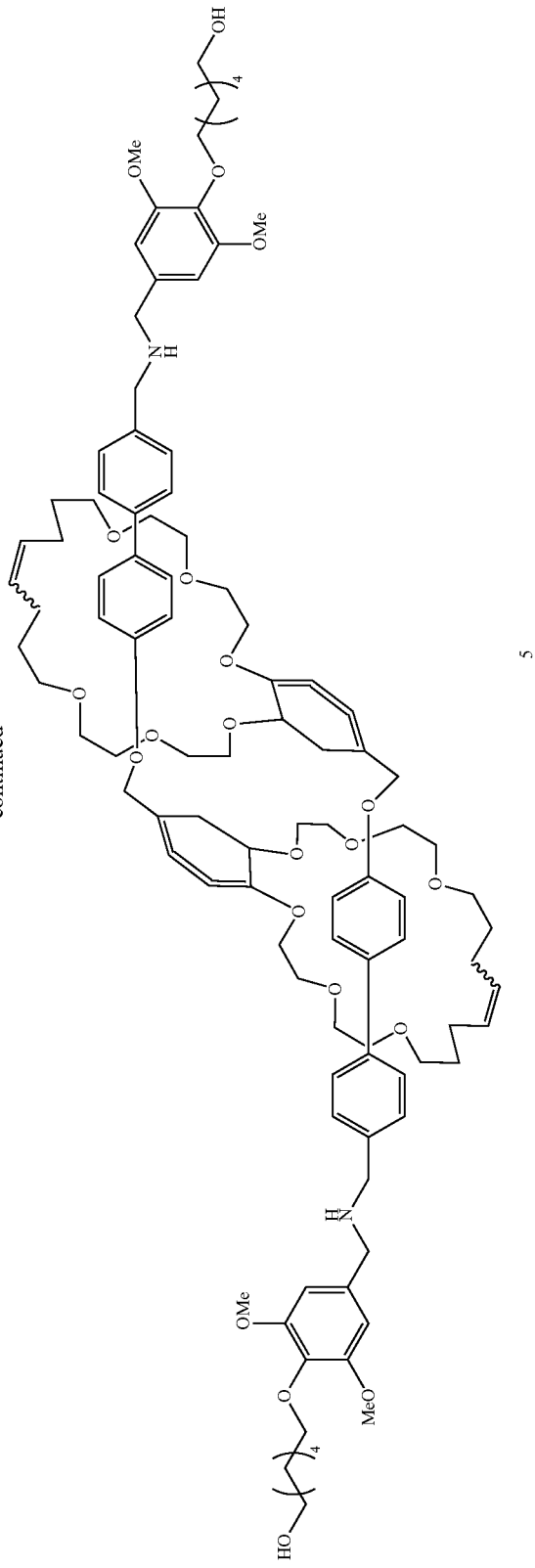

In particular, 3-H$_2$.2PF$_6$ (44.3 mg, 21.8 μmol, 1 eq) and deuterated acetonitrile (0.5 ml) were added to a vial, and this solution was transferred via pipet to a 5 mm NMR tube. To a separate vial was added potassium hydroxide (122 mg, 2.18 mmol, 100 eq) and deuterium oxide (0.50 ml). Using a 25 μl syringe (Hamilton 1700 Series Gastight Syringe), 5 μl injections (total of 3 injections) of the KOH/D$_2$O solution was added to the NMR tube. After each injection, the tube was vigorously shaken for 10-15 seconds, and then reinserted into the spectrometer. Deprotonation was complete after addition of 3 equivalents of potassium hydroxide, giving 5. The sample remained stable for 36 h, with an unchanged $^1$H NMR spectrum, and was subjected to reprotonation with no purification. $^1$H NMR (600 MHz, CD$_3$CN): δ 7.75-7.30 (br m, 5H), 7.30-7.15 (m, 4H), 7.15-6.19 (br m, 17H), 5.85-5.15 (br m, 4H), 4.87-3.15 (br m, 74H), 2.45-2.00 (br m, 8H), 1.83-1.53 (br m, 12H), 1.53-1.42 (m, 8H), 1.34 (qt, 4H). $^{13}$C NMR (126 MHz, CD$_3$CN): δ 159.48, 154.59, 148.98, 148.78, 147.07, 141.84, 140.98, 140.10, 139.12, 136.49, 134.58, 131.68, 131.10, 130.54, 130.02, 128.94, 126.69, 120.72, 116.51, 116.18, 112.85, 107.55, 107.29, 74.05, 72.76, 71.85, 71.49, 71.04, 70.77, 70.60, 70.42, 70.01, 69.70, 69.03, 68.47, 62.72, 56.99, 56.89, 54.86, 53.48, 33.74, 31.73, 31.10, 30.40, 29.71, 27.68, 26.81, 26.66.

A third vial was charged with deuterium oxide (0.5 ml) and hexafluorophosphoric acid (296 μl, 2.18 mmol, 100 eq, 60 wt % in H$_2$O). Using the same 25 μl syringe, 5 μl injections (total of 3 injections) of this solution were added to the NMR tube containing 5, restoring the $^1$H NMR spectrum corresponding to 3-H$_2$.2PF$_6$ and completing the "switching" of the dimer. (see $^1$H NMR spectral information for 3-H$_2$.2PF$_6$) Note: spectra were taken immediately after appropriate locking and shimming protocols with no extra time allowed for additional reaction. All deprotonation and reprotonation reactions were complete by the time the necessary NMR protocols were complete (<3 min).

After the switching was complete, the NMR sample was transferred to a vial and the solvent was removed under reduced pressure. The residue was dissolved in DCM (10 ml), and water was added (20 ml). The aqueous layer was extracted with fresh DCM (2×5 ml), and the combined organic layer further washed with fresh water (2×5 ml). The organic layer was poured through filter paper, and the solvent removed via rotary evaporation to return 3-H$_2$.2PF$_6$ (37.5 mg, 85% recovery). 3-H$_2$.2PF$_6$.was characterized by $^1$H NMR spectra as illustrated in the following Example 14.

Example 14

Conformational Switch: NMR Spectra of Protonated/Deprotonated Dimers

1 The protonated and deprotonated 3-H2 2PF6 of Example 13 were characterized by $^1$H NMR spectra to provide further confirmation of conformational switch between bound and unbound state associated with the protonation/deprotonation trigger.

Figure 14:
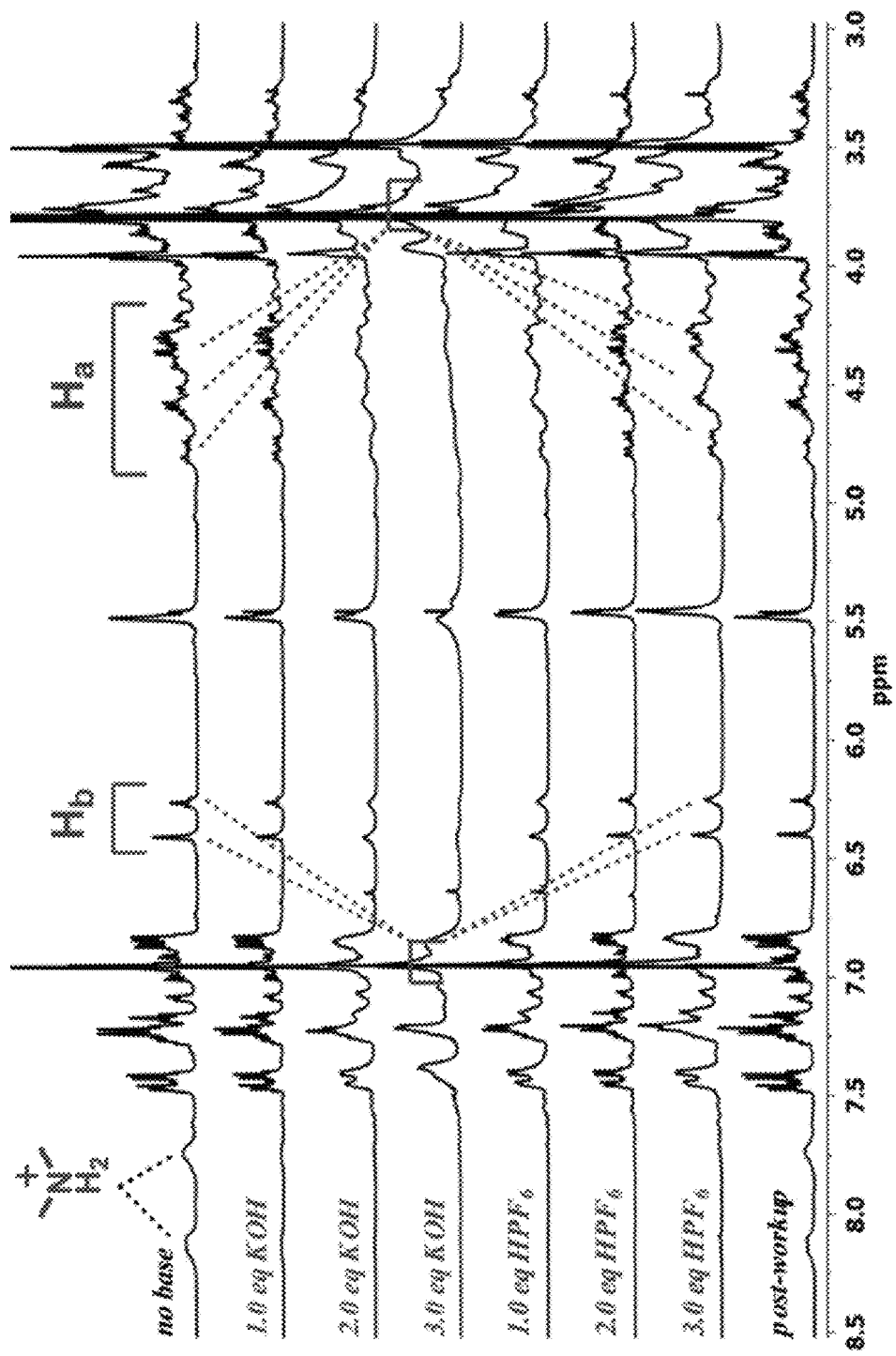
FIG. 14 shows a partial 1H NMR spectrum of 3-H2·2PF6 depicting the switching from bound to unbound conformations upon addition of 3.0 equiv of KOH and subsequent recoordination upon addition of 3.0 equiv of HPF6. An aqueous workup restores ammonium proton resonances.

The results illustrated in FIG. 14 showed that due to the absence of a secondary binding site, the 1H NMR spectrum broadens significantly upon deprotonation, indicating conformational heterogeneity possible only upon removal of crown-ammonium coordinating interactions. Heteronuclear single quantum coherence (HSQC) NMR analysis of the deprotonated dimer confirmed an upheld shift (from 4.5 ppm to 3.7 ppm) of the resonance of the benzylic protons Ha adjacent to the ammonium, suggesting deprotonation. Furthermore, the resonance of proton Hb shifts downfield to 7.0 ppm and coalesces, indicating the presence of a variety of conformations distinct from the native forms of 3-H2·2PF6. Upon addition of an equivalent amount of hexafluorophosphoric acid, the original 1H NMR spectrum of 3-H2·2PF6 was restored, completing the switching and showing facile return of the dimer to the contracted, bound conformation.

Example 15

[c2] Diazide Daisy-Chain Dimer (6-H$_2$.2PF$_6$)r

Figure 12:
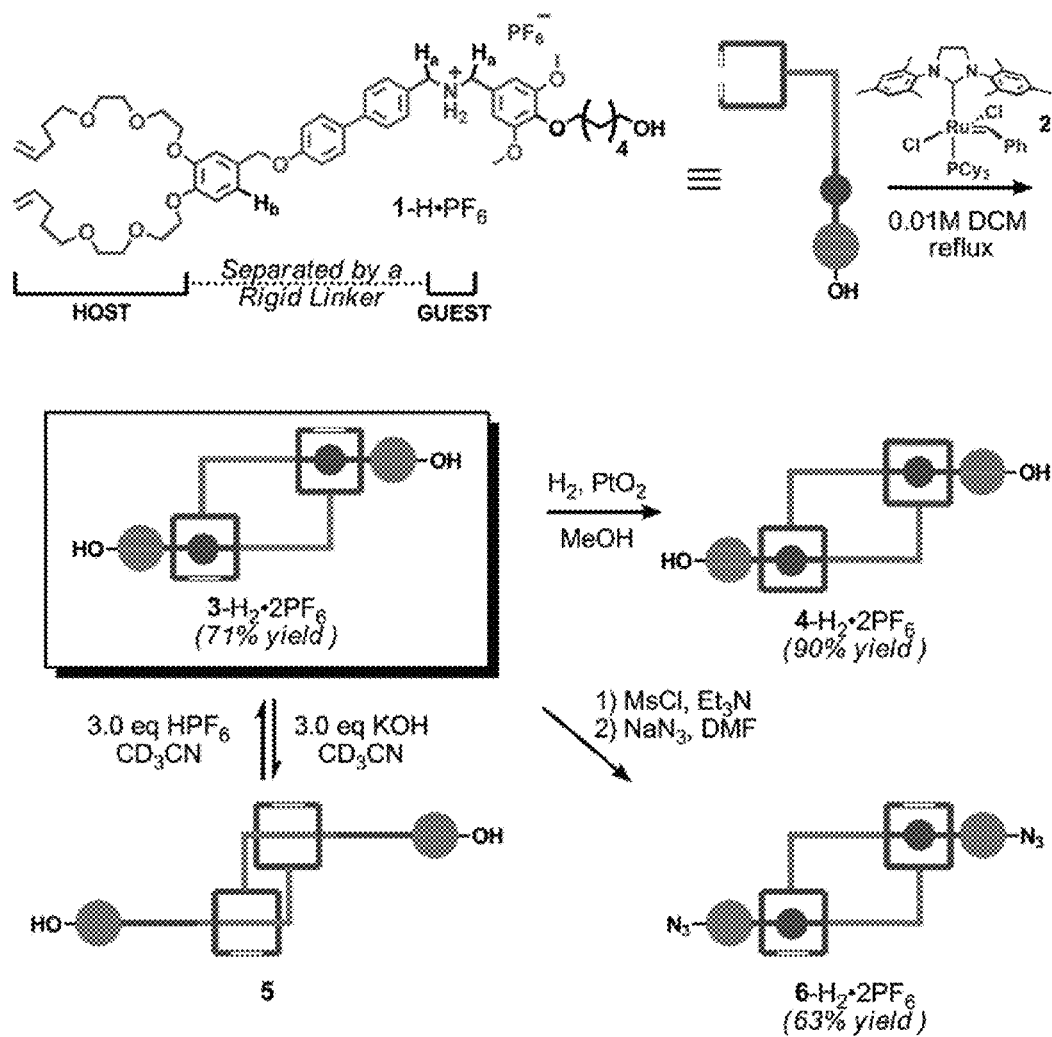
FIG. 12 shows a graphical representation of the synthesis of [c2]Daisy-Chain Dimer 3-H2·2PF6, Hydrogenated Derivative 4-H2·2PF6, Decoordinated Dimer 5, and Diazide Analogue 6-H2·2PF6

In preparation for materials synthesis, the terminal alcohols of 3-H2.PF6 were converted to mesylates and subsequently treated with sodium azide to give diazide 6-H2·2PF6 (FIG. 12).

In particular, the diazide [c2] daisy-chain dimer 6-H2·2PF6 was synthesized starting from dimers 3-H$_2$.2PF$_6$ according to the following reaction scheme.

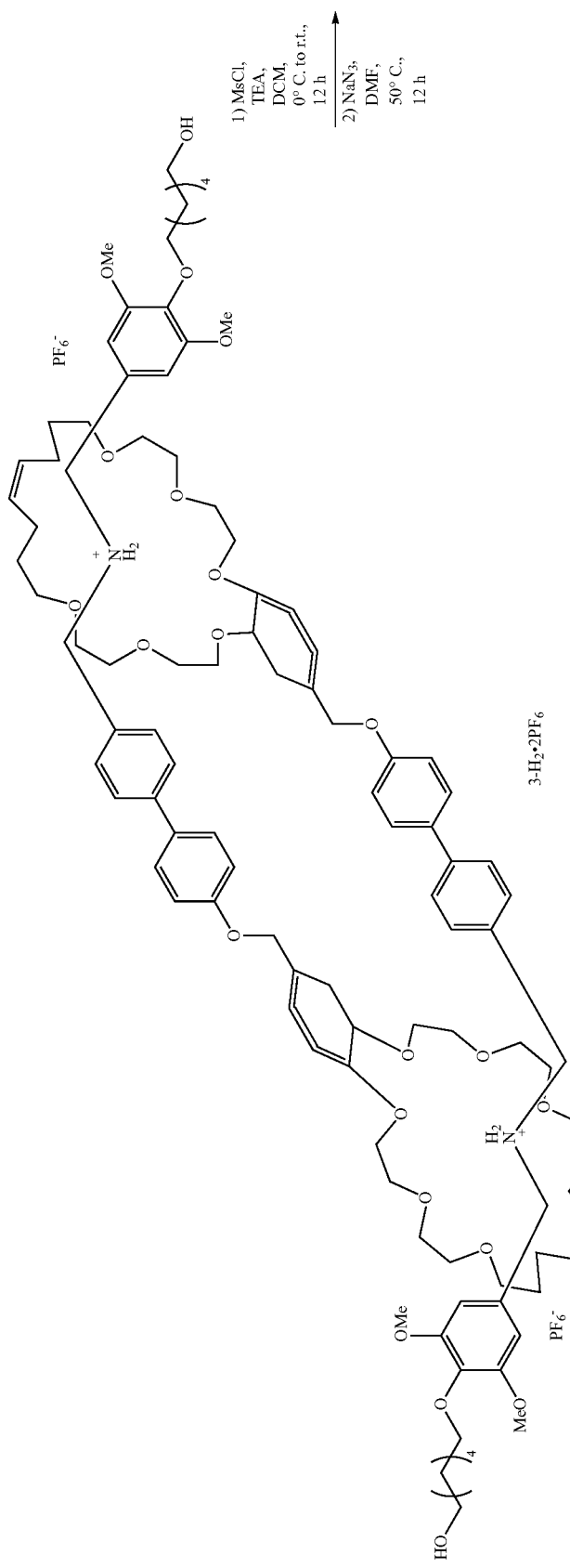

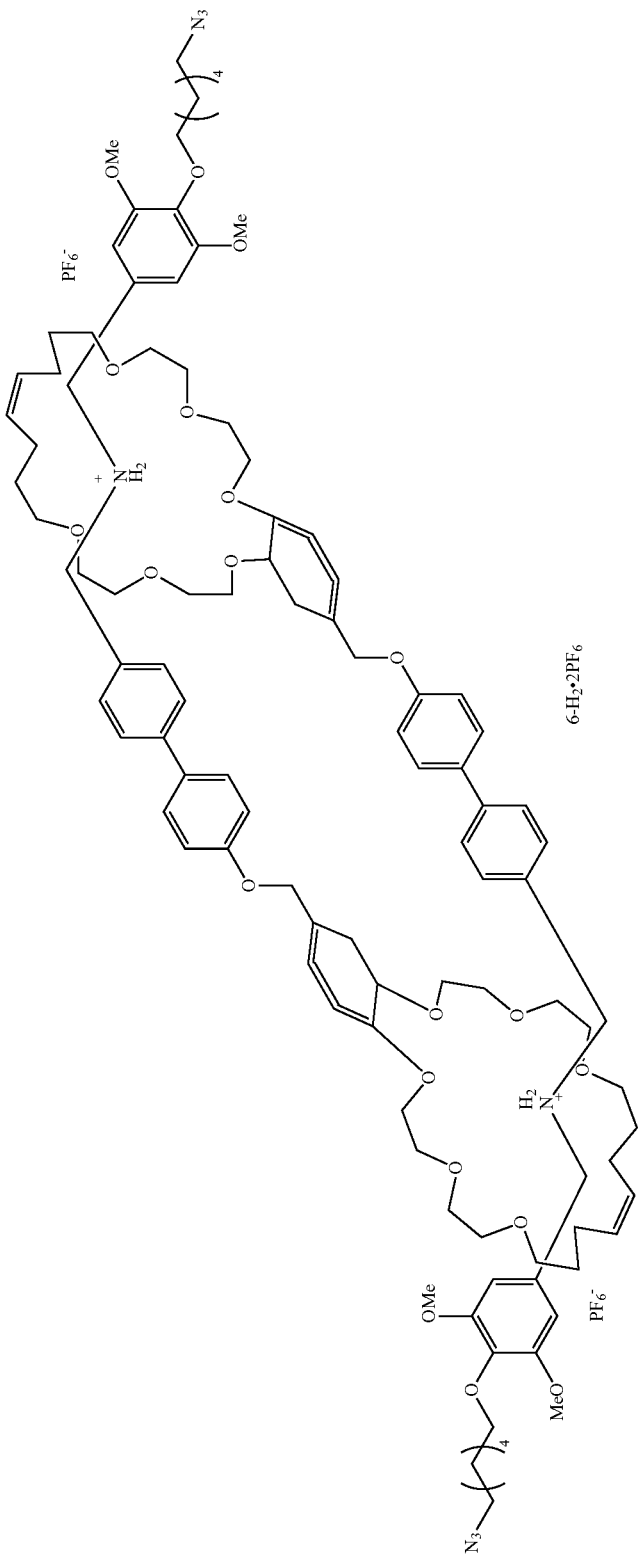

Crude 3-$H_2.PF_6$ was mixed with ethyl acetate (5 ml) and vigorously sonicated for 15 minutes giving a tan oil. The ethyl acetate was decanted, and a fresh portion of ethyl acetate (5 ml) was added. The suspension was again sonicated vigorously for 15 minutes, and the ethyl acetate was decanted to give a pale tan powder. This terminal diol [c2]daisy-chain dimer 3-$H_2.PF_6$ powder (2.58 g, 1.27 mmol, 1 eq) was dissolved in DCM (12.7 ml, 0.1 M) and triethylamine (1.1 ml, 7.62 mmol, 6 eq), and cooled to 0° C. To this stirring solution, mesyl chloride (0.60 ml, 7.62 mmol, 6 eq) was added dropwise. The reaction was warmed to room temperature for 12 h, then poured into a separatory funnel and diluted with water (100 ml) and DCM (25 ml). The aqueous layer was extracted with fresh DCM (2×25 ml), and the combined organic layer was washed with fresh water (50 ml). The organic layer was poured through filter paper, and evaporated to dryness. The resulting foam was mixed with ethyl acetate (5 ml) and subjected to sonication for 15 minutes. The ethyl acetate was decanted, and another 5 ml of fresh ethyl acetate was added. The suspension was sonicated for an additional 15 minutes, the ethyl acetate decanted, and the tan powder (2.24 g) was used without further purification. $^1$H NMR (500 MHz, CDCl$_3$): δ 8.08 (br m, 2H), 7.68 (br m, 2H), 7.43-7.27 (m, 4H), 7.22-7.02 (m, 8 H), 7.02-6.60 (m, 12 H), 6.32-6.10 (m, 2H), 5.68-5.21 (br m, 4 H), 5.05-4.01 (br m, 19 H), 3.96 (t, J=6.4 Hz, 4H), 3.93-3.10 (br m, 48 H), 2.97 (s, 4H), 2.42-1.93 (br m, 8 H), 1.90-1.31 (br m, 24 H).

The dimesylated dimer (2.24 g, 1.02 mmol, 1 eq) was added to a flame dried flask equipped with a stir bar and under a positive argon atmosphere, and dry DMF (50 ml, 0.02 M) was added. Sodium azide (0.80 g, 12.24 mmol, 12 eq) was added in one portion, and the reaction mixture was heated to 50° C. for 12 h. The solution was poured into a separatory funnel and diluted with ethyl acetate (100 ml) and water (50 ml). The aqueous layer was extracted with fresh ethyl acetate (4×25 ml), and the combined organic layer was washed with fresh water (50 ml). The organic layer was poured through filter paper and evaporated to dryness.

The resulting foam was sonicated with ethyl acetate (2×5 ml) to give 6-$H_2.2PF_6$ (1.67 g, 63%) as a pale tan foam that was used without further purification. $^1$H NMR (500 MHz, CDCl$_3$): δ 8.10 (br s, 2H), 7.65 (br s, 2H), 7.42-7.30 (m, 4H), 7.20-7.05 (m, 8H), 7.04 (d, J=7.8 Hz, 1H), 6.95-6.70 (m, 11H), 6.28 (m, 1H), 6.15 (m, 1H), 5.61-5.29 (m, 4H), 4.82-3.18 (br m, 72H), 2.41-1.90 (br m, 8H), 1.90-1.35 (m, 24H). $^{13}$C NMR (126 MHz, CDCl$_3$) δ 158.54, 158.48, 154.06, 154.01, 145.86, 145.70, 145.31, 145.18, 141.53, 137.94, 131.62, 131.13, 130.61, 129.98, 128.24, 127.86, 127.13, 126.23, 119.28, 118.75, 114.97, 111.89, 111.75, 109.89, 109.57, 105.94, 105.30, 77.48, 77.23, 76.98, 73.57, 73.47, 71.83, 71.36, 71.22, 71.16, 71.04, 70.36, 70.04, 69.88, 69.80, 69.40, 69.30, 68.67, 68.25, 67.93, 67.90, 67.57, 67.47, 62.89, 56.44, 56.40, 52.31, 52.27, 51.51, 32.79, 30.62, 30.54, 30.11, 30.05, 29.18, 29.14, 28.90, 28.39, 28.34, 28.15, 28.01, 26.59, 25.71, 25.62, 25.52, 24.96, 24.91. FTIR (NaCl, cm$^{-1}$): 3956.56, 3659.54, 3592.45, 3141.56, 3008.82, 2936.76, 2623.29, 2530.03, 2360.09, 2343.93, 2096.21, 1952.38, 1593.87, 1505.34, 1455.83, 1393.37, 1372.65, 1353.86, 1335.16, 1249.54, 1195.47, 1181.54, 1162.53, 1125.38, 1048.91, 973.99, 898.13, 838.37, 779.95, 763.92, 734.50, 701.42, 672.28, 644.56, 632.82, 619.78, 588.90, 557.67, 528.21. ESI-TOF MS (m/z): [M+2H−2PF$_6$]$^{+2}$ calcd for C$_{51}$H$_{69}$N$_4$O$_{10}$, 897.5013; found 897.5054. GPC (DMF with 0.2 M LiBr): $M_n$=3123 g/mol; $M_w$=3868 g/mol; PDI=1.24; dn/dc=0.121; $R_{gz}$=n/a.

Figure 16:
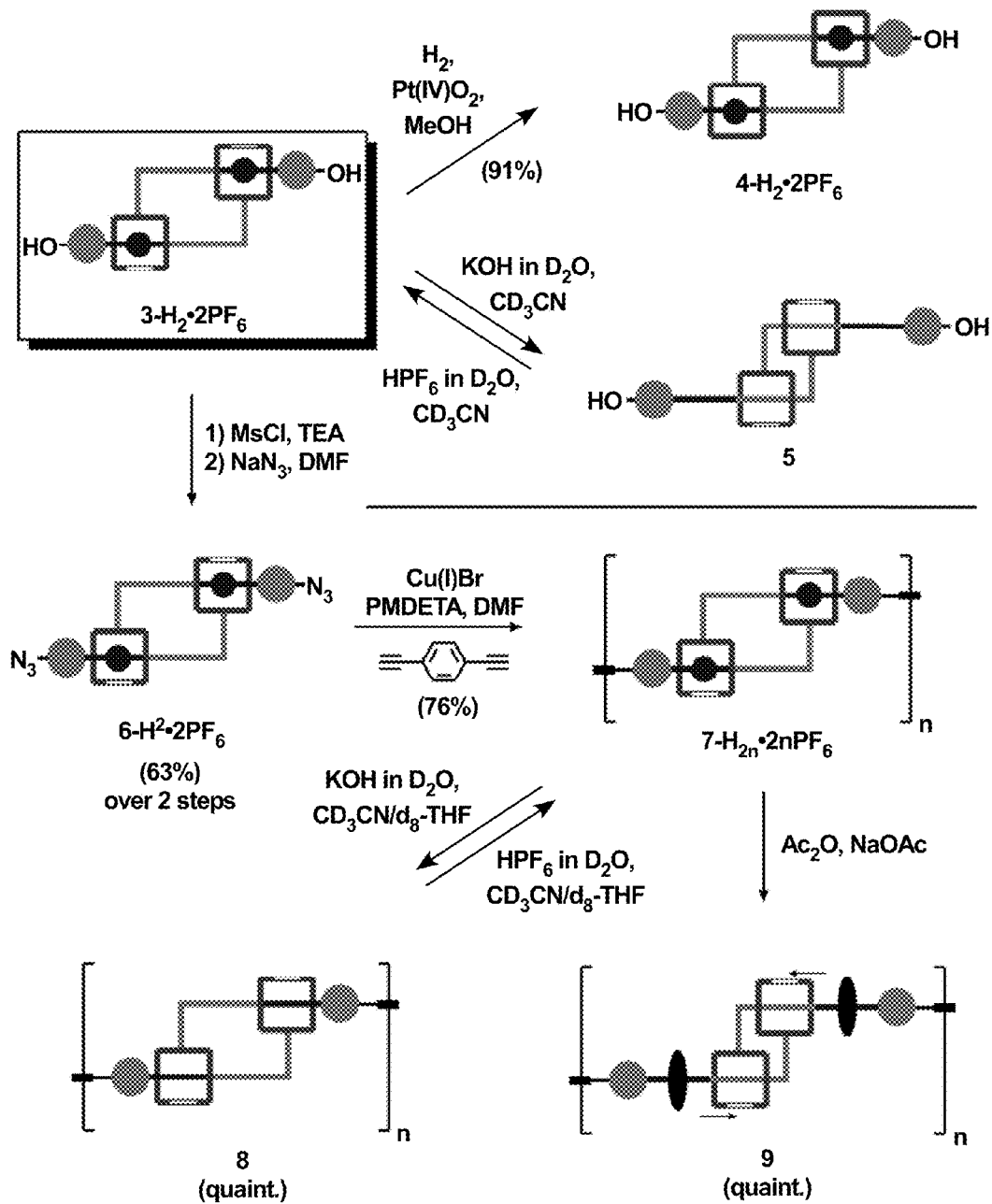
FIG. 16 shows a graphic representation depicting synthesis and modification of the conformation of a dimer according to some embodiments herein described.
Figure 17:
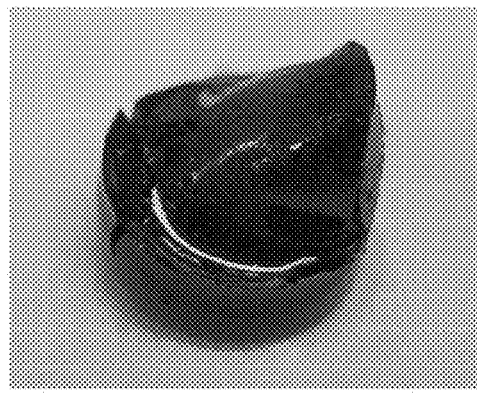
FIG. 17 shows a depiction of an amorphous gel formed by a [c2] daisy chain polymer according to some embodiments herein described.

The [c2] diazide daisy chain dimer 6-H2·2PF6 were used for the synthesis of Linear "Click" Polymer 7-H2n·2nPF6, Decoordinated Polymer 8a, and Extended Acylated Polymer 9a as illustrated in FIG. 16 and detailed in the following Examples 16, 17 and 18.

Example 16

[c2]Daisy-Chain Dimer Polymer (7-$H_{2n}.2PF_6$)

Figure 19:
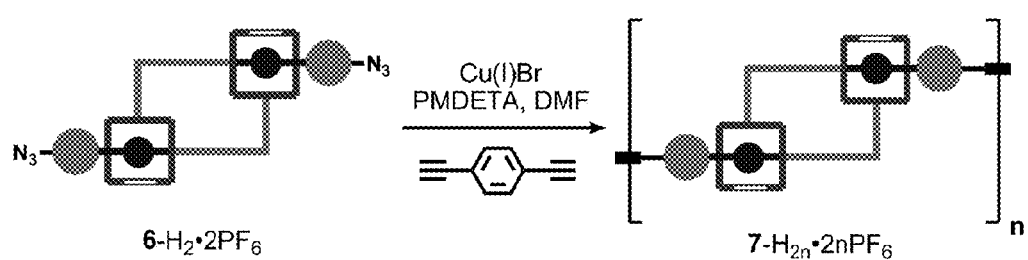
FIG. 19 shows a reaction scheme related to production of a [c2] daisy chain dimer polymer according to an embodiment herein described.

The [c2] daisy-chain polymer 7-$H_2.2nPF_6$ was prepared starting from 6-$H_2.2PF_6$, according to the reaction scheme of FIG. 19.

In particular, 6-$H_2.2PF_6$ (75.0 mg, 35.9 μmol, 1 eq), 1,4-diethynylbenzene (4.5 mg, 35.9 μmol, 1 eq), N,N,N',N'',N''-pentamethyl-diethylenetriamine (37.5 μl, 179.8 μmol, 5 eq), and dry DMF (360 μl, 0.1M) were added to a flame-dried vial equipped with a stir bar and septum cap. This mixture was subjected to standard freeze-pump-thaw protocol, with addition of copper(I) bromide (26.4 mg, 179.8 μmol, 5 eq) after the 3$^{rd}$ freeze. After the 4$^{th}$ freeze-pump-thaw cycle was completed, the vial was placed in a 50° C. oil bath for 24 h. The viscous reaction mixture was cooled to room temperature, and added dropwise to a stirring solution of methanol (40 ml). The precipitate was collected, dried, redissolved in dichloromethane (0.5 ml), and subjected to a second precipitation in fresh methanol (40 ml). The solid was collected and dried under reduced pressure to afford 7-$H_{2n}.2nPF_6$ (60.4 mg, 76% yield) as an off-white powder.

The product was used with no further purification. $^1$H NMR (500 MHz, CDCl$_3$): δ8.10 (br m, 4H), 7.91 (s, 4H), 7.82 (d, J=7.7 Hz, 0.6H), 7.70 (br s, 2H), 7.55 (d, J=8.1 Hz, 0.6 H), 7.48-7.35 (m, 5H), 7.28-7.02 (m, 11H), 7.01-6.75 (m, 13H), 6.45-6.15 (m, 2H), 5.71-5.35 (m, 4H), 4.85-3.08 (br m, 88H), 2.50-1.80 (br m, 10H), 1.80-1.35 (m, 28H+HDO). $^1$H NMR (500 MHz, CD$_2$Cl$_2$): δ8.12 (br m, 2H), 7.89 (s, 3H), 7.80 (d, J=8.1 Hz, 0.5 H), 7.68 (br s, 2H), 7.53 (d, J=7.3 Hz, 0.6 H), 7.48-7.30 (m, 4H), 7.28-7.08 (m, 9H), 7.05-6.60 (m, 11H), 6.40-6.10 (m, 2H), 5.71-5.35 (m, 4H), 4.90-3.08 (br m, 72H), 2.50-1.80 (br m, 12H), 1.80-1.35 (m, 22H+HDO). FTIR (NaCl, cm$^{-1}$): 3645.89, 3436.49, 3275.37, 3140.73, 3047.82, 3007.96, 2935.65, 2867.49, 2626.16, 2362.05, 2103.24, 1949.57, 1593.01, 1513.78, 1501.17, 1463.53, 1432.12, 1389.82, 1371.32, 1353.86, 1333.98, 1291.59, 1248.54, 1195.05, 1181.27, 1163.07, 1128.14, 1100.30, 1048.58, 973.32, 899.38, 842.74, 780.23, 763.80, 734.32, 700.48, 672.09, 644.03, 632.82, 619.48, 588.59, 557.58, 528.37. GPC (0.2 M LiBr in DMF): $M_n$=47,940 g/mol; $M_w$=141,100 g/mol; PDI=2.94; dn/dc=0.116; $R_{gz}$=14.8 nm.

Example 17

Deprotonation of [c2]Daisy-Chain Dimer Polymer 7-$H_{2n}.2nPF_6$)

Figure 20:
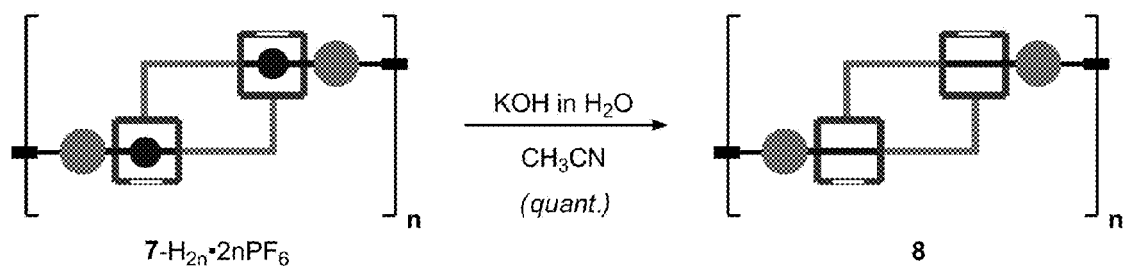
FIG. 20 shows a reaction scheme related to deprotonation of a [c2] daisy chain dimer polymer according to an embodiment herein described.

Deprotonation of [c2] daisy-chain polymer 7-$H_2.2nPF_6$ was performed according to the reaction scheme of FIG. 20.

In particular, a vial was charged with 7-$H_{2n}.2nPF_6$ (10 mg, 9 μmol, 1 eq) and acetonitrile (2 ml). To this mixture was added a 1.0 M solution of aqueous potassium hydroxide (1.8 ml), resulting in immediate precipitation of an off-white solid. The solution was decanted, and the solid was washed with fresh acetonitrile (2×2 ml). The deprotonated polymer 8 (9 mg, quant. yield) was analyzed with no further purification. The CD$_2$Cl$_2$ used in the NMR study was passed through a plug of basic alumina prior to addition to the deprotonated polymer sample. $^1$H NMR (500 MHz, CD$_2$Cl$_2$): δ 7.92-7.82 (m, 3.8H), 7.80 (d, J=7.7 Hz, 0.4H), 7.53 (d, J=7.9 Hz, 0.4H), 7.48-6.20 (m, 26H), 5.65-5.35 (m, 4H), 4.86-3.05 (br m, 72H), 2.55-1.55 (br m, 32H+$H_2O$ signal). GPC (0.2 M LiBr in DMF): $M_n$=41,680 g/mol; $M_w$=125,800 g/mol; PDI=3.02; dn/dc=0.148; $R_{gz}$=13.5 nm.

Example 18

5× Switching of Polymer 7-$H_{2n}$·2n$PF_6$

Figure 21:
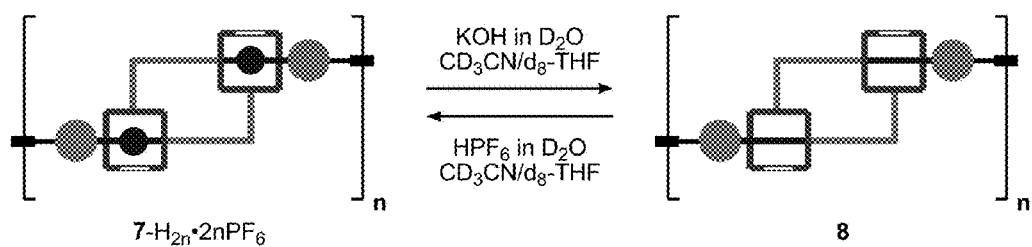
FIG. 21 shows a reaction scheme related to switching of a [c2] daisy chain polymer according to an embodiment herein described.

5× switching of polymer 7-$H_{2n}$·2n$PF_6$ was performed according to the reaction scheme of FIG. 21.

In particular, a vial was charged with 7-$H_{2n}$·2n$PF_6$ (11.6 mg, 5.3 μmol, 1 eq), and the polymer was dissolved in $CD_3CN$ (0.4 ml) and loaded in an NMR tube. To the tube was added $d_8$-THF (0.4 ml), and the mixture was shaken vigorously for several seconds. The switching was performed via addition of a stock solution of KOH in $D_2O$ (Stock Solution: 180 mg KOH in 0.5 ml $D_2O$; 5 μl injection volume, 6 eq) followed by vigorous shaking for 15 seconds to give 8, and, after analysis, subsequent reprotonation via addition of a stock solution of $HPF_6$ in $D_2O$ (450 μl 65% $HPF_6$ in 0.5 ml $D_2O$; 5 μl injection volume, 6 eq) to regenerate 7-$H_{2n}$·2n$PF_6$. See 5 for syringe specifications. After 5 cycles of deprotonation and reprotonation were completed, the polymer solution was transferred to a vial and the solvent was removed under reduced pressure. The residue was washed with water (2×2 ml) and dried under high vacuum, returning 7-$H_{2n}$·2n$PF_6$ as a white solid (11.6 mg, quant. yield). Protonated Polymer: $^1$H NMR (500 MHz, 1:1 $CD_3CN/d_8$-THF): δ8.25-8.02 (m, 2.8 H), 7.92 (m, 2.6H), 7.85 (d, J=8.0 Hz, 0.4H), 7.75 (br s, 2H), 7.53 (d, J=8.1 Hz, 0.4H), 7.48-7.35 (m, 4H), 7.32-7.13 (m, 8H), 7.12-6.75 (12H), 6.47-6.18 (m, 2H), 5.75-5.35 (m, 4H), 4.86-3.15 (br m, 72H+$d_8$-THF), 2.55-1.70 (m, 18H+ CD3CN+$d_8$-THF signal), 1.70-1.32 (m, 14H).

Example 19

Acylated [c2]Daisy-Chain Dimer Polymer

Figure 22:
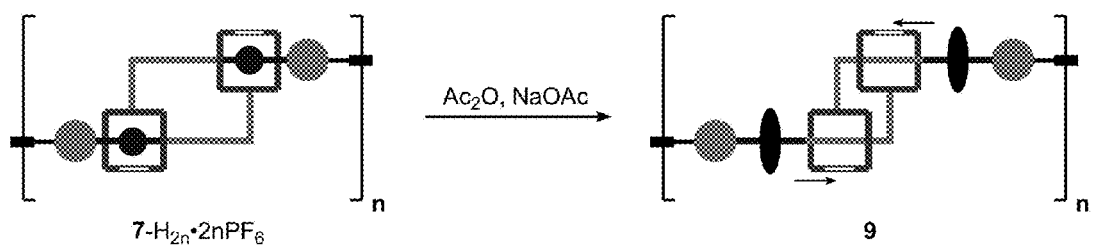
FIG. 22 shows a reaction scheme related to preparation of an acylated [c2] daisy chain dimer polymer according to an embodiment herein described.

An acylated [c2]Daisy-chain Dimer Polymer was prepared according to the reaction scheme of FIG. 22.

In particular, 7-$H_{2n}$·2n$PF_6$ (10.0 mg, 208 nmol, 1 eq), sodium acetate (18.5 mg, 225 μmol, 25 eq per ammonium), and acetic anhydride (500 μl) were added to a vial equipped with a stir bar. This solution was placed under a positive pressure of argon and heated to 90° C. for 2 hours. The acetic anhydride was removed under reduced pressure, and the resulting residue washed with water (3×2 ml) to give the acylated derivative 9 (9.1 mg, quant. yield) as an off white powder. The product was used with no further purification. $^1$H NMR (500 MHz, $CD_2Cl_2$): δ7.82-7.68 (m, 5H), 7.67-7.48 (m, 8H), 7.48-6.67 (br m, 15H), 6.45-6.15 (m, 6H), 5.50-4.98 (m, 4H), 4.60-4.15 (m, 16H), 4.09-3.05 (br m, 62H), 2.50-1.55 (br m, 30H), 1.50-1.28 (m, 10H). GPC (0.2 M LiBr in DMF): $M_n$=26,870 g/mol; $M_w$=117,200 g/mol; PDI=4.36; dn/dc=0.133; $R_{gz}$=21.8 nm.

Example 20

Macroscopic Gel Synthesis: Amorphous Gel

Figure 23:
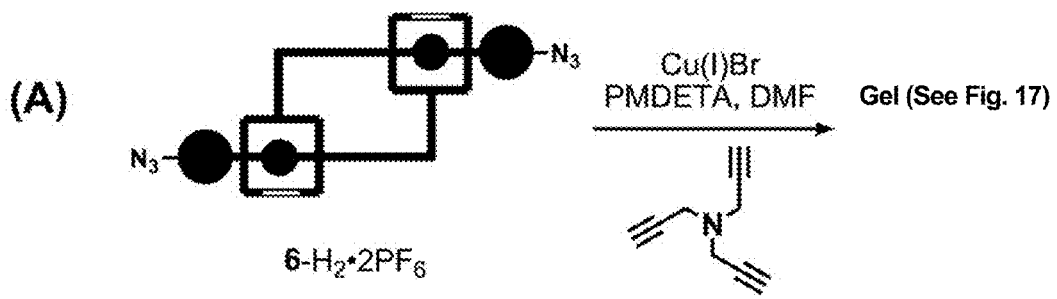
FIG. 23 shows a reaction scheme related to production of a macroscopic Gel-synthesis according to an embodiment herein described

An amorphous macroscopic gel formed by [2] Daisy-chain dimer 6-$H_2$·2$PF_6$ was prepared according to the reaction scheme of FIG. 23.

In particular, to an oven-dried vial equipped with a stir bar was added 6-$H_2$·2$PF_6$ (70.0 mg, 33.6 μmol, 1 eq), tripropargylamine (3.0 μl, 22.4 μmol, 0.67 eq), N,N,N',N',N"-pentamethyldiethylenetriamine (35.1 μl, 167.9 μmol, 5 eq) and dry DMF (340 μl, 0.1 M). This mixture was subjected to standard freeze-pump-thaw protocol, with addition of copper(I) bromide (48.2 mg, 33.6 μmol, 1 eq) after the 3$^{rd}$ freeze. After the 4$^{th}$ freeze-pump-thaw cycle was completed, the solution was allowed to warm to room temperature. The solution became deep green and, after 30 seconds to 1 minute, became a solid gel (see video). The vial was placed in a 50° C. oil bath for 2 days to complete reaction, then cooled to room temperature. The DMF and other volatiles were removed under reduced pressure, and the resulting amorphous gel was placed in a vial containing fresh DMF (10 ml). The DMF was removed and fresh DMF was added (3×10 ml) to afford a pale green gel. The volatiles were again removed to generate a hardened gel (73 mg, quant. yield).

Example 21

Macroscopic Gel Synthesis: Gel Cylinders

Figure 24:
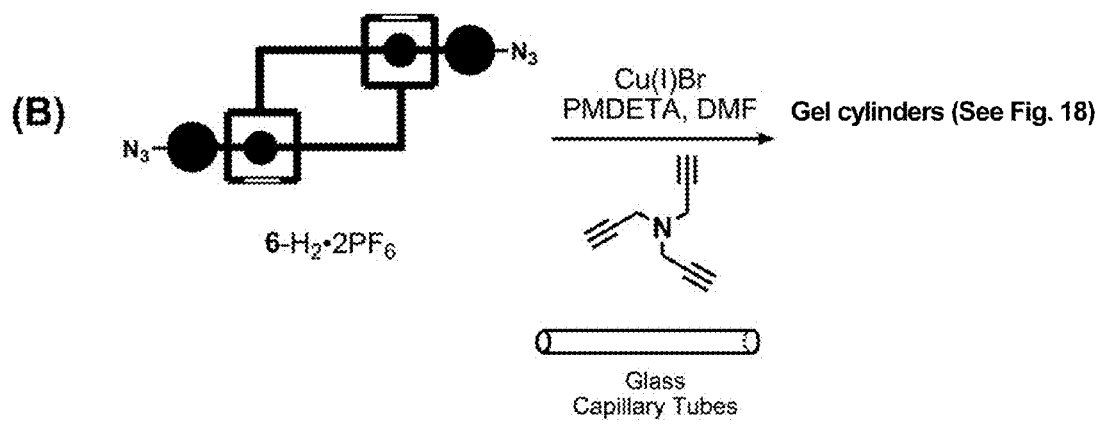
FIG. 24 shows a reaction scheme related to production of a macroscopic Gel-synthesis according to an embodiment herein described.

Gel cylinders of a macroscopic gel formed by [2] Daisy-chain dimer 6-$H_2$·2$PF_6$ was prepared according to the reaction scheme of FIG. 24.

Figure 18A:
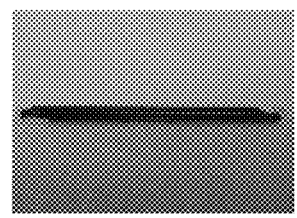
FIG. 18 shows a depiction of gel cylinders formed by a [c2] daisy chain polymer and a schematic representation of steps of a related method of production according to some embodiments herein described. Ruler increments in gel photos are in mm.
Figure 18B:
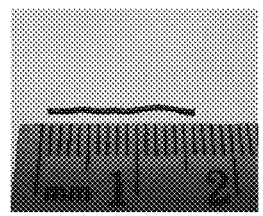
Figure 18C:
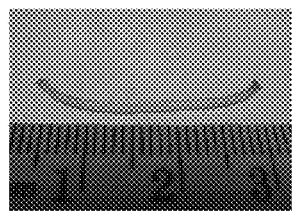

In particular, to an oven-dried vial equipped with a stir bar was added 6-$H_2$·2$PF_6$ (100 mg, 47.9 μmol, 1 eq), tripropargylamine (4.5 μl, 32.0 μmol, 0.67 eq), N,N,N',N',N"-pentamethyldiethylenetriamine (50.1 μl, 239.7 μmol, 5 eq), and dry DMF (0.48 ml, 0.1 M). This mixture was subjected to standard freeze-pump-thaw protocol, with addition of copper(I) bromide (34.4 mg, 239.8 μmol, 5 eq) after the 3$^{rd}$ freeze. After the 4$^{th}$ freeze-pump-thaw cycle was completed, the solution was allowed to warm to room temperature and was stirred for 30 seconds. The vial was rapidly opened and a glass capillary tube was added (cut to 20 mm long, 1.5-1.8 mm diameter, Kimax-51 Glass Capillary Tubes, Fischer Scientific Product Number #34505). The vial was turned horizontal and the solution was allowed to fill the capillary tube and solidify. After gelation, the vial was placed in a 50° C. oil bath for 2 days to complete reaction, then cooled to room temperature. The glass capillary tube with intercalated gel was removed from the surrounding amorphous gel, and placed in a vial under high vacuum (FIG. 18A). A blunt needle was used to carefully push the shrunken gel from the glass tube. After removal from the tube (FIG. 18B), the gel was subjected to repeated swellings with 1:1 DCM/Acteone (3×10 ml) to afford nearly-transparent gel cylinders (see FIG. 18C).

The examples set forth above are provided to give those of ordinary skill in the art a complete disclosure and description of how to make and use the embodiments of the macromer, dimers, polymers, compositions, systems and methods of the disclosure, and are not intended to limit the scope of what the inventors regard as their disclosure. Modifications of the above-described modes for carrying out the disclosure that are obvious to persons of skill in the art are intended to be within the scope of the following claims. All patents and publications mentioned in the specification are indicative of the levels of skill of those skilled in the art to which the disclosure pertains.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually.

It is to be understood that the disclosures are not limited to particular compositions materials, or biological systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

Unless otherwise indicated, the disclosure is not limited to specific reactants, substituents, catalysts, reaction conditions, or the like, as such may vary. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Thus, for example, reference to "a polymer" includes a single polymer as well as a combination or mixture of two or more polymers, reference to "a substituent" encompasses a single substituent as well as two or more substituents, and the like.

As used in the specification and the appended claims, the terms "for example," "for instance," "such as," or "including" are meant to introduce examples that further clarify more general subject matter. Unless otherwise specified, these examples are provided only as an aid for understanding the applications illustrated in the present disclosure, and are not meant to be limiting in any fashion.

In this disclosure and in the claims that follow, reference will be made to a number of terms, which shall be defined to have the following meanings:

The term "alkyl" as used herein refers to a linear, branched, or cyclic saturated hydrocarbon group typically although not necessarily containing 1 to about 10 carbon atoms, preferably 1 to about 6 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 6 carbon atoms. The term "cycloalkyl" intends a cyclic alkyl group, typically having 4 to 8, preferably 5 to 7, carbon atoms. The term "substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl, respectively.

The term "heteroatom-containing" as in a "heteroatom-containing alky group" refers to a alkyl group in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and "heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 24 carbon atoms, and particularly preferred aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituents in which at least one carbon atom is replaced with a heteroatom, as will be described in further detail infra.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 24 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. In some embodiments, alkaryl and aralkyl groups contain 6 to 24 carbon atoms, and particularly alkaryl and aralkyl groups contain 6 to 16 carbon atoms. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

The term "acyl" refers to substituents having the formula —(CO)-alkyl, —(CO)-aryl, or —(CO)-aralkyl, and the term "acyloxy" refers to substituents having the formula —O(CO)-alkyl, —O(CO)-aryl, or —O(CO)-aralkyl, wherein "alkyl," "aryl, and "aralkyl" are as defined above.

The terms "cyclic" and "ring" refer to alicyclic or aromatic groups that may or may not be substituted and/or heteroatom containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic or polycyclic.

The terms "halo" and "halogen" are used in the conventional sense to refer to a chloro, bromo, fluoro or iodo substituent.

1 The term "polyether" as used herein indicates a structure containing multiple carbon-oxygen-carbon covalent linkages.

The term "olefins" as used herein indicates two carbons covalently bound to one another that contain a double bond ($sp^2$-hybridized bond) between them. The other functional groups bound to each of these two carbons can be additional carbons, hydrogen atoms, or heteroatoms.

By "substituted" as in "substituted alkyl," "substituted aryl," and the like, as alluded to in some of the aforementioned definitions, is meant that in the, alkyl, aryl, or other moiety, at least one hydrogen atom bound to a carbon (or other) atom is replaced with one or more non-hydrogen substituents.

Examples of such substituents include, without limitation: functional groups such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{24}$ aryloxy, $C_6$-$C_{24}$ aralkyloxy, $C_6$-$C_{24}$ alkaryloxy, acyl (including $C_2$-$C_{24}$ alkylcarbonyl(—CO-alkyl) and $C_6$-$C_{24}$ arylcarbonyl (—CO-aryl)), acyloxy(—O-acyl, including $C_2$-$C_{24}$ alkylcarbonyloxy(—O—CO-alkyl) and $C_6$-$C_{24}$ arylcarbonyloxy(—O—CO-aryl)), $C_2$-$C_{24}$ alkoxycarbonyl(—(CO)—O-alkyl), $C_6$-$C_{24}$ aryloxycarbonyl(—(CO)—O-aryl), halocarbonyl(—CO)—X where X is halo), $C_2$-$C_{24}$ alkylcarbonato(—O—(CO)—O-alkyl), $C_6$-$C_{24}$ arylcarbonato(—O—(CO)—O-aryl), carboxy(—COOH), carboxylato(—COO⁻), carbamoyl (—(CO)—NH$_2$), mono-($C_1$-$C_{24}$ alkyl)-substituted carbamoyl(—(CO)—NH($C_1$-$C_{24}$ alkyl)), di-($C_1$-$C_{24}$ alkyl)-substituted carbamoyl(—(CO)—N($C_1$-$C_{24}$ alkyl)$_2$), mono-($C_5$-$C_{24}$ aryl)-substituted carbamoyl(—(CO)—NH-aryl), di-($C_5$-$C_{24}$ aryl)-substituted carbamoyl(—(CO)—N($C_5$-$C_{24}$ aryl)$_2$), di-N—($C_1$-$C_{24}$ alkyl), N—($C_5$-$C_{24}$ aryl)-substituted carbamoyl, thiocarbamoyl(—(CS)—NH$_2$), mono-($C_1$-$C_{24}$ alkyl)-substituted thiocarbamoyl(—(CO)—NH($C_1$-$C_{24}$ alkyl)), di-($C_1$-$C_{24}$ alkyl)-substituted thiocarbamoyl(—(CO)—N($C_1$-$C_{24}$ alkyl)$_2$), mono-($C_5$-$C_{24}$ aryl)-substituted thiocarbamoyl(—(CO)—NH-aryl), di-($C_5$-$C_{24}$ aryl)-substituted thiocarbamoyl(—(CO)—N($C_5$-$C_{24}$ aryl)$_2$), di-N—($C_1$-$C_{24}$ alkyl), N—($C_5$-$C_{24}$ aryl)-substituted thiocarbamoyl, carbamido(—NH—(CO)—NH$_2$), cyano(—C≡N), cyanato (—O—C≡N), thiocyanato(—S—C≡N), formyl(—(CO)—H), thioformyl(—(CS)—H), amino(—NH$_2$), mono-($C_1$-$C_{24}$ alkyl)-substituted amino, di-($C_1$-$C_{24}$ alkyl)-substituted amino, mono-($C_5$-$C_{24}$ aryl)-substituted amino, di-($C_5$-$C_{24}$ aryl)-substituted amino, $C_2$-$C_{24}$ alkylamido(—NH—(CO)-alkyl), $C_6$-$C_{24}$ arylamido(—NH—(CO)-aryl), imino(—CR=NH where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino(—CR=N(alkyl), where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino(—CR=N(aryl), where R=hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro(—NO$_2$), nitroso (—NO), sulfo(—SO$_2$—OH), sulfonato(—SO$_2$—O⁻), $C_1$-$C_{24}$ alkylsulfanyl(—S-alkyl; also termed "alkylthio"), $C_5$-$C_{24}$ arylsulfanyl(—S-aryl; also termed "arylthio"), $C_1$-$C_{24}$ alkylsulfinyl(—(SO)-alkyl), $C_5$-$C_{24}$ arylsulfinyl(—(SO)-aryl), $C_1$-$C_{24}$ alkylsulfonyl(SO$_2$-alkyl), $C_5$-$C_{24}$ arylsulfonyl(—SO$_2$-aryl), boryl(—BH$_2$), borono(—B(OH)$_2$), boronato(—B(OR)$_2$ where R is alkyl or other hydrocarbyl), phosphono(—P(O)(OH)$_2$), phosphonato(—P(O)(O⁻)$_2$), phosphinato(—P(O)(O⁻)), phospho(—PO$_2$), phosphino(—PH$_2$), silyl (—SiR$_3$ wherein R is hydrogen or hydrocarbyl), and silyloxy(—O-silyl); and the hydrocarbyl moieties $C_1$-$C_{24}$ alkyl (preferably $C_1$-$C_{12}$ alkyl, more preferably $C_1$-$C_6$ alkyl), $C_2$-$C_{24}$ alkenyl (preferably $C_2$-$C_{12}$ alkenyl, more preferably $C_2$-$C_6$ alkenyl), $C_2$-$C_{24}$ alkynyl (preferably $C_2$-$C_{12}$ alkynyl, more preferably $C_2$-$C_6$ alkynyl), $C_5$-$C_{24}$ aryl (preferably $C_5$-$C_{14}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl).

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

The term "distal" as used herein indicates substitution in the para-position (aryl rings), or at the farthest possible point of attachment from the point of origin (cyclic alkyl ring).

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

In the molecular structures herein, the use of bold and dashed lines to denote particular conformation of groups follows the IUPAC convention. A bond indicated by a broken line indicates that the group in question is below the general plane of the molecule as drawn, and a bond indicated by a bold line indicates that the group at the position in question is above the general plane of the molecule as drawn.

The term "carbon chain" as used herein indicates a linear or branched line of connected carbon atoms.

Although any methods and materials similar or equivalent to those described herein can be used in the practice for testing of the specific examples, additional appropriate materials and methods are described herein.

A number of embodiments of the disclosure have been described. Nevertheless, it will be understood that various modifications may be made without departing from the spirit and scope of the present disclosure. Accordingly, other embodiments are within the scope of the following claims.

REFERENCES (1) Rescifina, A.; Zagni, C.; Iannazzo, D.; Merino, P. *Curr. Org. Chem.* 2009, 13, 448-481.

(2) (a) Meyer, C. D.; Joiner, C. S.; Stoddart, J. F. *Chem. Soc. Rev.* 2007, 36, 1705-1723. (b) Haussmann, P. C.; Stoddart, J. F. *Chem. Record* 2009, 9, 136-154. (c) Rowan, S. J.; Cantrill, S. J.; Cousins, G. R. L.; Sanders, J. K. M.; Stoddart, J. F. *Angew. Chem., Int. Ed.* 2002, 41, 898-952.

(3) (a) Bilig, T.; Oku, T.; Furusho, Y.; Koyama, Y.; Asai, S.; Takata, T. *Macromolecules* 2008, 41, 8496-8503. (b) Bugler, J.; Sommerdijk, N. A. J. M.; Visser, A. J. W. G.; van Hoek, A.; Nolte, R. J. M.; Engbersen, J. F. J.; Reinhoudt, D. N. *J. Am. Chem. Soc.* 1999, 121, 28-33. (c) Hirotsu, K.; Higuchi, T.; Fujita, K.; Ueda, T.; Shinoda, A.; Imoto, T.; Tabushi, I. *J. Org. Chem.* 1982, 47, 1143-1144. (d) Liu, Y.; Li; Fan, Z.; Zhang, H.-Y.; Wu, X.; Guan, X.-D.; Liu, S.-X. *Nano Lett.* 2002, 2, 257-261. (e) Liu, Y.; You, C.-C.; Zhang, M.; Weng, L.-H.; Wada, T.; Inoue, Y. *Org. Lett.* 2000, 2, 2761-2763. (f) Wu, J.; Leung, K. C.-F.; Stoddart, J. F. *Proc. Natl. Acad. Sci. U.S.A.* 2007, 104, 17266-17271.

(4) (a) Cantrill, S. J.; Youn, G. J.; Stoddart, J. F.; Williams, D. J. *J. Org. Chem.* 2001, 66, 6857-6872. (b) M. Consuelo Jime'nez, M. C.; Dietrich-Buchecker, C.; Sauvage, J.-P.; De Cian, A. *Angew. Chem., Int. Ed.* 2000, 39, 1295-1298. (c) Yamaguchi, N.; Devdatt, S.; Nagvekar, D. S.; Gibson, H. W. *Angew. Chem., Int. Ed.* 1998, 37, 2361-2364. (d) Peter, R.; Ashton, P. R.; Baxter, I.; Cantrill, S. J.; Fyfe, M. C. T.; Glink, P. T.; Stoddart, J. F.; White, A. J. P.; Williams, D. J. *Angew. Chem., Int. Ed.* 1998, 37, 1294-1297.

(5) (a) Coutrot, F.; Romuald, C.; Busseron, E. *Org. Lett.* 2008, 10, 3741-3744. (b) Wu, J.; Leung, K. C.-F.; Benitez, D.; Han, J.-Y.; Cantrill, S. J.; Fang, L.; Stoddart, J. F. *Angew. Chem., Int. Ed.* 2008, 47, 7470-7474. (c) Jime'nez, M. C.; Dietrich-Buchecker, C.; Jean-Pierre Sauvage, J.-P. *Angew.Chem.* 2000, 39, 3284-3287. (d) Elizarov, A. M.; Chiu, S.-H.; Stoddart, J. F. *J. Org. Chem.* 2002, 67, 9175-9181. (e) Pease, A. R.; Jeppesen, J. O.; Stoddart, J. F.; Luo, Y.; Collier, C. P.; Heath, J. R. *Acc. Chem. Res.* 2001, 34, 433-444.

(6) (a) Fustin, C. A.; Clarkson, G. J.; Leigh, D. A.; Van Hoof, F.; Jonas, A. M.; Bailly, C. *Macromolecules* 2004, 37, 7884-7892. (b) Fustin, C.-A.; Bailly, C.; Clarkson, G. J.; Galow, T. H.; Leigh, D. A. *Macromolecules* 2004, 37, 66-70.

(7) (a) Fustin, C.-A.; Bailly, C.; Clarkson, G. J.; De Groote, P.; Galow, T. H.; Leigh, D. A.; Robertson, D.; Slawin, A. M. Z.; Wong, J. K. Y. *J. Am. Chem. Soc.* 2003, 125, 2200-2207. (b) Watanabe, N.; Ikari, Y.; Kihara, N.; Takata, T. *Macromolecules* 2004, 37, 6663-6666. (c) Werts, M. P. L.; van den Boogaard, M.; Tsivgoulis, G. M.; Hadziioannou, G. *Macromolecules* 2003, 36, 7004-7013.

(8) (a) Guidry, E. N.; Li, J.; Stoddart, J. F.; Grubbs, R. H. *J. Am. Chem. Soc.* 2007, 129, 8944-8945. (b) Fang, L.; Hmadeh, M.; Wu, J.; Olson, M. A.; Spruell, J. M.; Trabolsi, A.; Yang, Y.-W.; Elhabiri, M.; Albrecht-Gary, A.-M.; Stoddart, J. F. *J. Am. Chem. Soc.* 2009, 131, 7126-7134.

(9) (a) Chiu, S.-H.; Rowan, S. J.; Cantrill, S. J.; Stoddart, J. F.; White, A. J. P.; Williams, D. J. *Chem. Commun.* 2002, 2948-2949. (b) Rowan, S. J.; Cantrill, S. J.; Stoddart, J. F.; White, A. J. P.; Williams, D. J. *Org. Lett.* 2000, 2, 759-762. (c) Ueng, S.-H.; Hsueh, S.-Y.; Lai, C.-C.; Liu, Y.-H.; Peng, S.-M.; Chiu, S.-H. *Chem. Commun.* 2008, 817-819. (d) Hoshino, T.; Miyauchi, M.; Kawaguchi, Y.; Yamaguchi, H.; Harada, A. *J. Am. Chem. Soc.* 2000, 122, 9876-9877.

(10) (a) Trnka, T. M.; Grubbs, R. H. *Acc. Chem. Res.* 2001, 34, 18-29. (b) Scholl, M.; Ding, S.; Lee, C. W.; Grubbs, R. H. *Org. Lett.* 1999, 1, 953-956.

(11) (a) Kidd, T. J.; Leigh, D. A.; Wilson, A. J. *J. Am. Chem. Soc.* 1999, 121, 1599-1600. (b) Weck, M.; Mohr, B.; Sauvage, J.-P.; Grubbs, R. H. *J. Org. Chem.* 1999, 64, 5463-5471. (c) Mobian, P.; Kern, J.-M.; Sauvage, J.-P. *J. Am. Chem. Soc.* 2003, 125, 2016-2017. (d) Sambrook, M. R.; Beer, P. D.; Wisner, J. A.; Paul, R. L.; Cowley, A. R. *J. Am. Chem. Soc.* 2004, 126, 15364-15365. (e) Guidry, E. N.; Cantrill, S. J.; Stoddart, J. F.; Grubbs, R. H. *Org. Lett.* 2005, 7, 2129-2132.

(12) (a) Wisner, J. A.; Beer, P. D.; Drew, M. G. B.; Sambrook, M. R. *J. Am. Chem. Soc.* 2002, 124, 12469-12476. (b) Kilbinger, A. F. M.; Cantrill, S. J.; Waltman, A. W.; Day, M. W.; Grubbs, R. H. *Angew. Chem., Int. Ed.* 2003, 42, 3281-3285. (c) Hannam, J. S.; Kidd, T. J.; Leigh, D. A.; Wilson, A. J. *Org. Lett.* 2003, 5, 1907-1910.

(13) (a) Coumans, R. G. E.; Elemans, J. A. A. W.; Thordarson, P.; Nolte, R. J. M.; Rowan, A. E. *Angew. Chem., Int. Ed.* 2003, 42, 650-654. (b) Badjic', J. D.; Cantrill, S. J.; Grubbs, R. H.; Guidry, E. N.; Orenes, R.; Stoddart, J. F. *Angew. Chem., Int. Ed.* 2004, 43, 3273-3278. (c) Wang, L.; Vysotsky, M. O.; Bogdan, A.; Bolte, M.; Bohmer, V. *Science* 2004, 304, 1312-1314. (d) Zhu, X.-Z.; Chen, C.-F. *J. Am. Chem. Soc.* 2005, 127, 13158-13159.

(14) Nielsen, M. B.; Hansen, J. G.; Becher, J. *Eur. J. Org. Chem.* 1999, 2807-2815.

(16) Crystallographic data have been deposited at the CCDC: deposition number 734570. See Supporting Information of Paul G. Clark, Michael W. Day and Robert H. Grubbs *J. Am. Chem. Soc.,* 2009, 131 (38), pp 13631-13633 for complete details.

(17) Coates, G. W.; Dunn, A. R.; Henling, L. M.; Dougherty, D. A.; Grubbs, R. H. *Angew. Chem., Int. Ed.* 1997, 36, 248-251.

(18) Liu, Y.; Flood, A. H.; Bonvallet, P. A.; Vignon, S. A.; Northrop, B. H.; Tseng, H.-R.; Jeppesen, J. O.; Huang, T. J.; Brough, B.; Baller, M.; Magonov, S.; Solares, S. D.; Goddard, W. A.; Ho, C.-M.; Stoddart, J. F. *J. Am. Chem. Soc.* 2005, 127, 9745-97.

(19) (a) Kolb, H. C.; Finn, M. G.; Sharpless, K. B. *Angew. Chem., Int. Ed.* 2001, 40, 2004-2021. (b) Lutz, J.-F. *Angew. Chem., Int. Ed.* 2008, 47, 2182-2184.

What is claimed is:

1. A [c2] daisy chain macromer, comprising
    a binding site and a corresponding recognition moiety, the binding site presenting a secondary amine and the corresponding recognition moiety comprising a first polyether chain and a second polyether chain, the first polyether chain presenting a first olefin and the second polyether chain presenting a second olefin, the first and second polyether chains being configured to allow binding of the first olefin with the second olefin through a metathesis reaction;
    a backbone portion located between the binding site and the recognition moiety, wherein the backbone portion comprises structurally rigid functionalities configured to minimize intramolecular interactions between the binding site and the corresponding recognition moiety; and
    a cap portion adjacent to the binding site, the cap portion configured to constrain movements of the recognition moiety when coordinately bound to the binding site, the cap portion and the recognition moiety being located at opposite ends of the macromer,
    wherein the binding site and the recognition moiety are configured to allow a coordinate binding of the recognition moiety to the binding site with an association constant ($K_a$) equal to or greater than about 75 M$^{-1}$; and
    wherein the cap portion, the binding site, the backbone and the recognition moiety are attached together to form a linear [c2]daisy chain macromer structure.

2. The [c2] daisy chain macromer of claim 1, wherein the backbone portion comprises substituted or unsubstituted biphenyl structures.

3. The [c2] daisy chain macromer of claim 1, wherein the backbone portion comprises terminally functionalized naphthalene, anthracene, or naphthacene.

4. The [c2] daisy chain macromer of claim 1, having formula

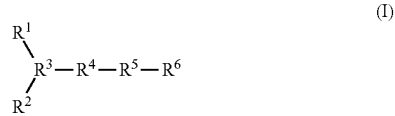
(I)

wherein
R¹ and R² are independently a polyether chain of formula (II)

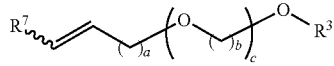

(II)

wherein
R⁷ is a hydrogen or a linear carbon chain having 1 to 3 carbon atoms
a is 2 to 5,
b is independently 1 to 3 for each iteration of the carbon oxygen chain, and
c is 1 to 3;
R3 has formula (III), (IV) (V), (VI), (VII), (VIII) or (IX)

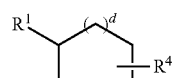

(III)

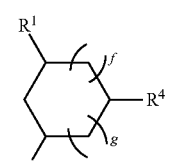

(IV)

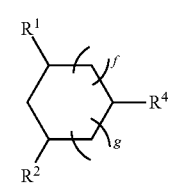

(V)

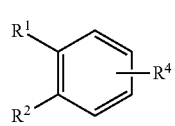

(VI)

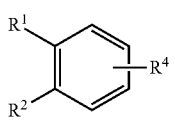

(VII)

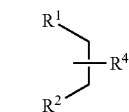

(VIII)

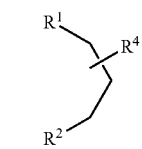

(IX)

wherein
d is 1 to 3,
e is 1 to 3,
f is 1 to 3, and
g is 1 to 3;

R⁴ has formula (X) or (XI)

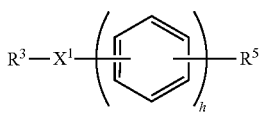

(X)

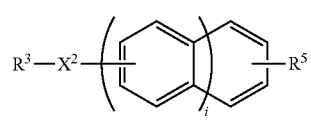

(XI)

wherein
X¹ and X² are a linear or branched, optionally heteroatom containing, alkyl chain having 1 to 4 carbons, wherein the heteroatom is oxygen or sulfur,
h is 1 to 3, and
i is 1 to 3;
R⁵ has formula (XII)

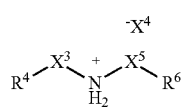

(XII)

wherein
X³ and X⁵ are independently: a linear alkyl chain having 1 to 3 carbons; a single ring aryl moiety linking N and R⁴ in meta or para positions; an aryloxy group; or an aralkoxy group, and
X⁴ is a negative charged species capable of engaging in attractive ionic interactions with the $NH_2+$ moiety; and
R⁶ has formula (XIII), (XIV) or (XV)

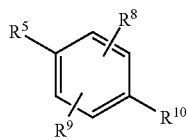

(XIII)

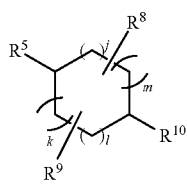

(XIV)

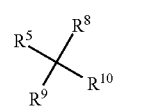

(XV)

wherein
R⁸ and R⁹ are independently an alkyl, alkoxy, or an aryl group,
R⁸ can be covalently attached to any carbon of the j alkyl chain or the m alkyl chain,
R⁹ can be covalently attached to any carbon of the k alkyl chain or the l alkyl chain, $R^{10}$ is an H, or a linear or branched alkyl chain having 1 to 20 carbon atoms having a terminal functional group, j is 0 to 3,
k is 0 to 3,
l is 0 to 3, and
m is 0 to 3.

5. The [c2] daisy chain macromer of claim 4, wherein at least one of $R^1$ and $R^2$ is a compound of formula (II) wherein b is 2 and is the same for each iteration of the carbon oxygen chain.

6. The [c2] daisy chain macromer of claim 5, wherein c is 2.

7. The [c2] daisy chain macromer of claim 4, wherein $R^1$, $R^2$ and $R^3$ form together a compound of formula (XVI)

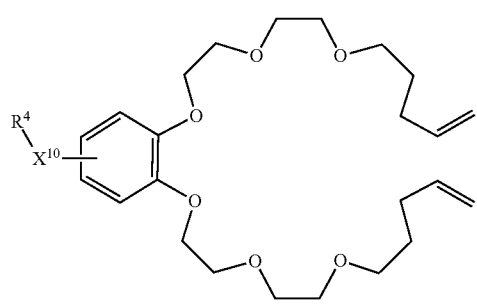

(XVI)

wherein
$x^{10}=$ is —O—, an alkyl chain (—CH$_2$—)q , or S, and
q is 1 to 3.

8. The [c2] daisy chain macromer of claim 4, wherein R4 is a compound of formula (XVII) or (XVIII)

(XVII)

(XVIII)

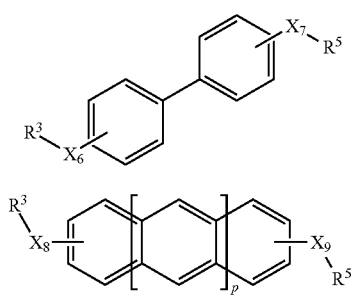

wherein
$X^6$, $X^7$, $X^8$, and $X^9$ are independently —O—, —CH$_2$—, or —S— and
p is 0 to 3.

9. The [c2] daisy chain macromer of claim 4, wherein $R^4$ is a compound of formula (XVII) or (XVIII) wherein $X^6$, $X^7$, $X^8$ and $X^9$ are CH$_2$ and P is 0 or 1.

10. The [c2] daisy chain macromer of claim 4, wherein $R^5$ is a compound of Formula (XII) wherein $X^3$ and $X^4$ are independently an optionally substituted aryl moiety, —CH$_2$—, —O—, or —S—, n is 1 to 10, and $X^5$ is Trifloroacetate, Chloride, Bromide, Hexafluorophosphate, Triflate, or tetrakis [3,5-bis(trifluoromethyl)phenyl]-borate.

11. The [c2] daisy chain macromer of claim 4, wherein $R^5$ is a compound of Formula (XII) wherein $X^3$ and $X^4$ are independently: a benzyl moiety optionally meta substituted with an alkyl group, an aryl group or an alkoxy group.

12. The [c2] daisy chain macromer of claim 4, wherein $R^6$ is a compound of formula (XIX)

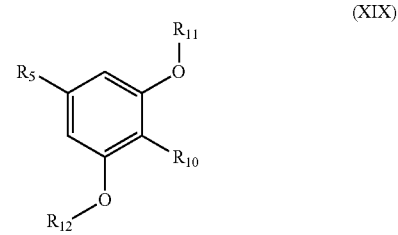

(XIX)

wherein
$R^{11}$ is an alkyl group, and
$R^{12}$ is an aryl group.

13. A [c2] daisy chain dimer comprising
a first [c2] daisy chain macromer according to claim 1 comprising a first binding site, a first backbone portion and a first recognition moiety wherein the first and second polyether chains of the first recognition moiety are linked one to another to form a first polyether crown; and
a second [c2] daisy chain macromer according to claim 1, comprising a second binding site, a second backbone portion and a second recognition moiety wherein the first and second polyether chains of the second recognition moiety are linked one to another to form a second polyether crown;
wherein the first [c2] daisy chain macromer and the second [c2] daisy chain macromer are interlocked and
wherein
in a contracted state of the [c2] daisy chain dimer the first recognition moiety is coordinately bound to the second binding site and the second recognition moiety is coordinately bound to the first binding site; and
in an extended state of the [c2] daisy chain dimer, coordinated interactions between the first recognition moiety and the second binding site and between the second recognition moiety and the first binding site are minimized; and
wherein
switching between the extended state and contracted state is controllable upon removal or reinstatement of coordinating interactions between the binding sites and the recognition moieties.

14. A [c2] daisy-chain polymer comprising two or more [c2] daisy-chain dimers according to claim 13, covalently linked one to the other to form a linear [c2] daisy chain polymer.

15. A composition comprising at least one of the [c2] daisy-chain macromer according to claim 1, [c2] daisy-chain dimers according to claim 13 and [c2] daisy-chain polymer according to claim 14 together with a suitable vehicle.

16. A material comprising the [c2] daisy chain polymer according to claim 14.

17. A method to provide the [c2] daisy-chain macromer of claim 1, the method comprising:
providing a linear backbone fragment comprising structurally rigid functionalities and having a first end and a second end;

providing a binding site/cap fragment comprising a binding site portion and a cap portion; and providing a recognition fragment configured to provide a recognition moiety interlocked to the binding site;

attaching the first end of the backbone fragment to the binding site portion of the binding site/cap fragment; and attaching the second end of the backbone fragment to the recognition fragment, to provide a linear [c2] daisy-chain macromer.

18. A method to actuate a [c2] daisy-chain dimer or polymer, the method comprising:

providing the [c2] daisy-chain dimer of claim 13 or the [c2] daisy-chain polymer of claim 14, the [c2] daisy-chain dimer or polymer able to assume an extended state and a contracted state and controlling the state of the [c2] daisy-chain dimer or polymer by coordinating interactions between binding sites and recognition moieties within the [c2] daisy-chain dimer or polymer.

\* \* \* \* \*